US010458990B1

United States Patent
Manautou et al.

(10) Patent No.: US 10,458,990 B1
(45) Date of Patent: Oct. 29, 2019

(54) SPORE STATE DISCRIMINATION

(71) Applicant: Scanit Technologies, Inc., Fremont, CA (US)

(72) Inventors: Pedro Manautou, Milpitas, CA (US); Joel Kent, Fremont, CA (US)

(73) Assignee: Scanit Technologies, Inc., Fremont, CA (US)

( * ) Notice: Subject to any disclaimer, the term of this patent is extended or adjusted under 35 U.S.C. 154(b) by 146 days.

(21) Appl. No.: 15/667,829

(22) Filed: Aug. 3, 2017

Related U.S. Application Data

(63) Continuation-in-part of application No. 15/178,170, filed on Jun. 9, 2016, now Pat. No. 9,933,351, which
(Continued)

(51) Int. Cl.
*G01N 33/58* (2006.01)
*A61B 5/15* (2006.01)
(Continued)

(52) U.S. Cl.
CPC ..... *G01N 33/582* (2013.01); *A61B 5/150213* (2013.01); *C12N 1/14* (2013.01);
(Continued)

(58) Field of Classification Search
CPC .. G01N 33/582; G01N 21/33; G01N 2333/37; G01N 2021/646; A61B 5/150213; C12N 1/14; C12N 3/00
(Continued)

(56) References Cited

U.S. PATENT DOCUMENTS

| 4,240,444 A | 12/1980 | Virguito et al. |
| 5,955,376 A | 9/1999 | Tovey |

(Continued)

FOREIGN PATENT DOCUMENTS

| JP | 19970239205 | 3/1999 |
| WO | WO2013182822 A1 | 12/2013 |

(Continued)

OTHER PUBLICATIONS

"Knowledge-driven Personalized Contextual mHealth Service for Asthma Management in Children", Pramod Anantharam et al., 2015 IEEE International Conference on Mobile Services, Jun. 2015, pp. 284-291.
(Continued)

*Primary Examiner* — Tri T Ton
(74) *Attorney, Agent, or Firm* — Staniford Tomita LLP

(57) ABSTRACT

A flow of air including a fungal spore is directed to a collection cartridge. The spore is trapped within the cartridge and positioned within a field of view of a camera sensor. A UV light is activated to illuminate the spore and a camera shutter is opened for a time period. The camera sensor collects light emitted from the spore during a first portion of the time period. After the first portion has elapsed, first and second bursts of white light originating from first and second positions, respectively, are directed towards the spore during a second portion of the time period. After the second portion of the time period has elapsed, the camera shutter is closed to generate an image. The image is analyzed to obtain a shape of the spore.

11 Claims, 56 Drawing Sheets
(13 of 56 Drawing Sheet(s) Filed in Color)

Related U.S. Application Data is a continuation-in-part of application No. 15/061,883, filed on Mar. 4, 2016.

(60) Provisional application No. 62/370,604, filed on Aug. 3, 2016, provisional application No. 62/173,280, filed on Jun. 9, 2015, provisional application No. 62/210,253, filed on Aug. 26, 2015, provisional application No. 62/129,571, filed on Mar. 6, 2015, provisional application No. 62/188,606, filed on Jul. 3, 2015.

(51) Int. Cl.
*C12N 1/14* (2006.01)
*G01N 21/33* (2006.01)
*C12N 3/00* (2006.01)
*G01N 21/64* (2006.01)

(52) U.S. Cl.
CPC ............... *G01N 21/33* (2013.01); *C12N 3/00* (2013.01); *G01N 2021/646* (2013.01); *G01N 2333/37* (2013.01)

(58) Field of Classification Search
USPC .................................................. 356/300–343
See application file for complete search history.

(56) References Cited

U.S. PATENT DOCUMENTS

| | | |
|---|---|---|
| 6,359,681 B1 | 3/2002 | Housand |
| 6,594,001 B1 | 7/2003 | Yabusaki |
| 6,608,682 B2 | 8/2003 | Ortyn et al. |
| 6,964,189 B2 | 11/2005 | Carlson et al. |
| 7,006,923 B1 | 2/2006 | Rubin |
| 7,207,948 B2 | 4/2007 | Coyle |
| 7,711,495 B2 | 5/2010 | Perner |
| 8,031,968 B2 | 10/2011 | Ishiga |
| 8,038,944 B1 | 10/2011 | Gordon et al. |
| 8,222,061 B2 | 7/2012 | Xu et al. |
| 8,404,198 B2 | 3/2013 | Amshey et al. |
| 8,506,686 B2 | 8/2013 | Langle et al. |
| 8,639,043 B2 | 1/2014 | Levenson et al. |
| 8,806,915 B2 | 8/2014 | White et al. |
| 8,906,673 B2 | 12/2014 | Vu et al. |
| 8,930,341 B2 | 1/2015 | Amin |
| 2002/0028519 A1* | 3/2002 | Yguerabide ......... C12Q 1/6816 436/518 |
| 2004/0227938 A1 | 11/2004 | Craig |
| 2005/0030534 A1 | 2/2005 | Oldham |
| 2005/0142608 A1 | 6/2005 | Uchida et al. |
| 2005/0261841 A1 | 11/2005 | Shepard et al. |
| 2007/0263217 A1 | 11/2007 | Otsuki |
| 2010/0255560 A1 | 10/2010 | Call et al. |
| 2013/0029408 A1 | 1/2013 | Gordon |
| 2014/0206034 A1 | 7/2014 | Gordon et al. |
| 2014/0228657 A1 | 8/2014 | Palley et al. |
| 2014/0252274 A1 | 9/2014 | Masson et al. |
| 2014/0273184 A1 | 9/2014 | Gordon |
| 2014/0288396 A1 | 9/2014 | LeBoeuf et al. |
| 2014/0298890 A1 | 10/2014 | Pruett |
| 2014/0353475 A1 | 12/2014 | Meyers |

FOREIGN PATENT DOCUMENTS

| | | |
|---|---|---|
| WO | WO2014124133 A1 | 8/2014 |
| WO | WO2014207629 | 12/2014 |

OTHER PUBLICATIONS

"Local Production of IgG, IgA, and IgE Antibodies in Grass Pollen Hay Fever", Thomas A.E. Platts-Mills, J Immunology 1979, http://www.jimmunol.org/content/122/6/2218, pp. 2218-2225.

Wikipedia, "Palynology" available at <http://en.wikipedia.org/wiki/Palynology >, retrieved May 16, 2015, pp. 1-7.

International Federation of Palynologial Societies, "PALYNOS", available at <http://www.geo.arizona.edu/palynology/plns1406.pdf>, retrieved May 6, 2015, pp. 1-23.

13th in International Palynological Congress & International Organization of Palaeobotany, Katherine Holt & Keith Bennett, IPC XIII .IOPC IX 2012 Conference session (SS18) organizers, "(SS18) Progress and future direction of automated palynology", previously available at http://www.psj3.org/ipc-%C2%AD-iopc2012/Download_files/SS18.pdf, retrieved Nov. 26, 2014, pp. 1-6.

Maureen E. Lacey and Jonathan S. West, "The Air Spora", book published by Springer in 2006, pp. 1-163.

Massey University (Computer-Aided Palynology), <http://www.classifynder.com/index.php?q=content/system_operation> retrieved Mar. 6, 2016, pp. 1-13.

Gildardo Lozano Vega et al., "Sketch of an automatic image based pollen detection system", available at <https://hal.archives-ouvertes.fr/hal-00824014/PDF/Lozano_et_al_DGPF_2012_Sketch_of_an_automatic_image_based_pollen_detection_system_pdf>, retrieved May 31, 2015, pp. 1-9.

Thomas Drugman et al., "Objective Study of Sensor Relevance for Automatic Cough Detection", Journal of LATEX Class Files, vol. 6., No. 1, Jan. 2007, pp. 1-8.

Mayo Clinic, "Hay Fever / Symptoms", available at <http://www.mayoclinic.org/diseases-conditions/hay-fever/basics/symptoms/con-20020827>, retrieved May 31, 2015, pp. 1-4.

John T. Connell, "Quantitative Intranasal Pollen Challenges" III. The priming effect in allergic rhinitis; Jan. 1969; pp. 1-12.

Phil Etheridge, "Discrimination of Pollen Taxa from Digital Image Feature Data"; Institute of Information Sciences and Technology Massey University; Oct. 18, 2005; pp. 1-20.

G.P. Allen et al., "Automatic Recognition of Light-Microscope Pollen Images"; available at <http://www.classifynder.com/sites/default/papers/ivcnz06GApollenAutoRecognition.pdf>, retrieved Mar. 6, 2016, pp. 1-6.

Ping Li et al., "Pollen texture identification using neural networks"; 1999 Scandinavian University Press. ISSN 0017-3134; Grana 38; pp. 1-6.

P. Li et al., "Towards automation of palynology 2: the use of texture measures and neural network analysis for automated identification of optical images of pollen grains"; Journal of Quaternary Science (2004) 19(8); pp. 1-8.

E.C. Stillman et al.;"The Needs and Prospects for Automation in Palynology"; Quaternary Science Reviews, vol. 15, pp. 1-5, 1996.

W. J. Treloar et al., "Towards automation of palynology 1: analysis of pollen shape and ornamentation using simple geometric measures, derived from scanning electron microscope images"; Journal of Quaternary Science (2004) 19(8) 145-754; pp. 1-10.

Michael Wachs et al.; "Observations on the pathogenesis of nasal priming"; Department of Medicine (Division of clinical Immunology) and Otolaryngology, The John Hopkins University School of Medicine, Baltimore, MD.,1989; pages 1-12.

Y. Zhang et al., "Towards automation of palynology 3: pollen pattern recongnition using Gabor transforms and digital moments"; Journal of Quaternary Science (2004) 19(8) 763-768; pp. 1-6.

Craig Alexander Holdaway, "Automation of Pollen Analysis using a Computer Microscope," 2004, pp. 1-125.

(Levetin, E) Methods for Aeroallergen Sampling. Curr Allergy Asthma Rep. Sep. 2004; vol. 4 No. 5; pp. 376-383; table 1.

(Kirmaz, C et al.) Symptoms of the Olive Pollen Allergy; Do They Really Occur Only in the Pollination Season?. J Investig Allergol Clin Immunol; 2005; vol. 15, No. 2; pp. 140-145; abstract; p. 141, col. 1, paragraph 4; p. 142; col. 1, paragraph 1.

"International Search Report and the Written Opinion of the International Searching Authority"; International Application No. PCT/US16/21058; International Filing Date: Mar. 4, 2016; pp. 1-13.

Burkard, "Personal Volumetric Air Sampler" available at <http://www.burkard.co.uk/perssamp.htm>, retrieved Jul. 3, 2016, 1 page.

Aclima, available at <https://aclima.io/what>, retrieved Jul. 3, 2016, 5 pages.

Inspirotec, available at <http://inspirotec.com>, retrieved Jul. 3, 2016, 3 pages.

(56) References Cited

OTHER PUBLICATIONS

C. Pohlker, et. al., "Autofluorescence of atmospheric bioaerosols—fluorescent biomolecules and potential interferences," Atmos. Meas. Tech., 5, 37-71, 2012, Jan. 9, 2012, pp. 37-71, Copernicus Publications.

"International Search Report and the Written Opinion of the International Searching Authority, or Declaration"; PCT Application No. PCT/US2016/036713 filed Jun. 9, 2016; Applicant: Scanit Technologies, Inc.

Accuweather Allergy Forecast, available at <http://www.accuweather.com>, accessed Jun. 14, 2017.

Berger, Uwe, et al., "Personalized Pollen-Related Symptom-Forecast Information Services for Allergic Rhinitis Patients in Europe," Allergy, European Journal of Allergy and Clinical Immunology, Jul. 2013, pp. 1-4.

Pollen.com "Sign in to Personalize Your Pollen.com Experience," available at <http://www.pollen.com>, accessed Jun. 14, 2017.

Polleninfo.org "Welcome to the Pollen Diary," available at <http://www.polleninfo.org>, accessed Jun. 14, 2017.

International Preliminary Report on Patentability, PCT/US2016/021058, International Filing Date Mar. 4, 2016, Applicant: Scanit Technologies, Inc.

\* cited by examiner

2172

Particle Detected: Powdery Mildew

Date and Time of Capture: July 4, 2017

Determined State: Virulent

Particle Detected: Powdery Mildew

Date and Time of Capture: July 6, 2017

Determined State: Sterile

Figure 21D

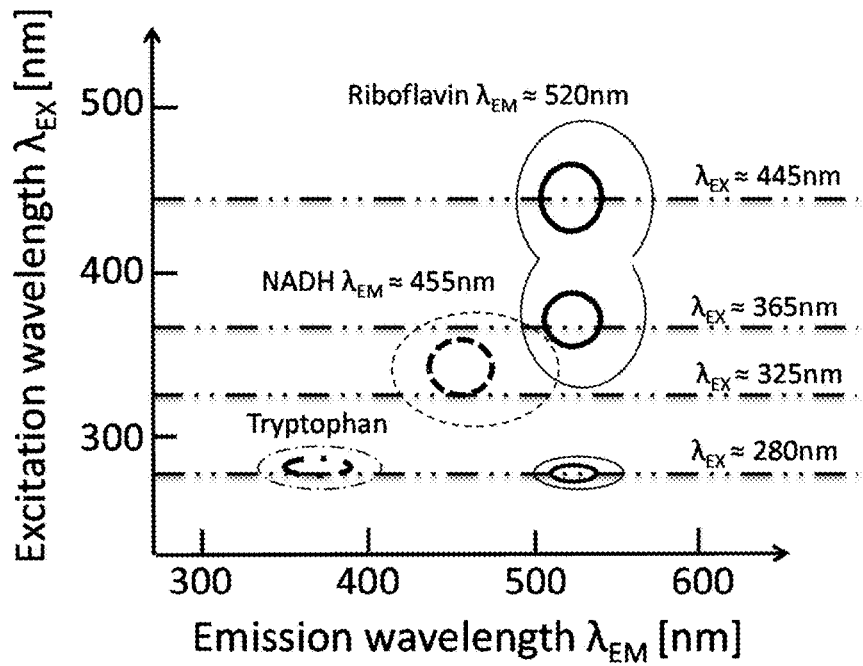

Figure 28S (a) $\lambda_{EX}$ = 445nm (blue) → riboflavin → $\lambda_{EM}$ = 520nm (green)

(b) $\lambda_{EX}$ = 365nm (UV) → riboflavin → $\lambda_{EM}$ = 520nm (green)
(c) $\lambda_{EX}$ = 365nm (UV) → NADH → $\lambda_{EM}$ = 455nm (blue)

(d) $\lambda_{EX}$ = 325nm (UV) → riboflavin → $\lambda_{EM}$ = 520nm (green)
(e) $\lambda_{EX}$ = 325nm (UV) → NADH → $\lambda_{EM}$ = 455nm (blue)

(f) $\lambda_{EX}$ = 280nm (UV) → riboflavin → $\lambda_{EM}$ = 520nm (green)
(g) $\lambda_{EX}$ = 280nm (UV) → tryptophan → $\lambda_{EM}$ < ~400nm (violet & UV)

Figure 29

$$RGB_i^{\lambda_{EX}}(x,y) = \sum_j p_i(\lambda_{EM}) \cdot F_j^{\lambda_{EX} \to \lambda_{EM}} \cdot C_j(x,y)$$

i = RED, GREEN or BLUE j = RIBOFLAVIN, NADH or TRYPTOPHAN $\lambda_{EM}$ = 520nm (riboflavin), 455nm (NADH) or <~400nm (tryptophan)

$\lambda_{EX}$ = 445nm, 365nm, 325nm, or 280nm

Figure 30

$RGB_{RED}^{445nm}(x,y) = p_{RED}(520nm) \cdot F_{RIBOFLAVIN}^{445nm \to 520nm} \cdot C_{RIBOFLAVIN}(x,y)$ $RGB_{RED}^{365nm}(x,y) = p_{RED}(520nm) \cdot F_{RIBOFLAVIN}^{365nm \to 520nm} \cdot C_{RIBOFLAVIN}(x,y) + p_{RED}(455nm) \cdot F_{NADH}^{365nm \to 455nm} \cdot C_{NADH}(x,y)$ $RGB_{GREEN}^{365nm}(x,y) = p_{GREEN}(520nm) \cdot F_{RIBOFLAVIN}^{365nm \to 520nm} \cdot C_{RIBOFLAVIN}(x,y) + p_{GREEN}(455nm) \cdot F_{NADH}^{365nm \to 455nm} \cdot C_{NADH}(x,y)$ $RGB_{BLUE}^{365nm}(x,y) = p_{BLUE}(520nm) \cdot F_{RIBOFLAVIN}^{365nm \to 520nm} \cdot C_{RIBOFLAVIN}(x,y) + p_{BLUE}(455nm) \cdot F_{NADH}^{365nm \to 455nm} \cdot C_{NADH}(x,y)$ $RGB_{RED}^{325nm}(x,y) = p_{RED}(520nm) \cdot F_{RIBOFLAVIN}^{325nm \to 520nm} \cdot C_{RIBOFLAVIN}(x,y) + p_{RED}(455nm) \cdot F_{NADH}^{325nm \to 455nm} \cdot C_{NADH}(x,y)$ $RGB_{GREEN}^{325nm}(x,y) = p_{GREEN}(520nm) \cdot F_{RIBOFLAVIN}^{325nm \to 520nm} \cdot C_{RIBOFLAVIN}(x,y) + p_{GREEN}(455nm) \cdot F_{NADH}^{325nm \to 455nm} \cdot C_{NADH}(x,y)$ $RGB_{BLUE}^{325nm}(x,y) = p_{BLUE}(520nm) \cdot F_{RIBOFLAVIN}^{325nm \to 520nm} \cdot C_{RIBOFLAVIN}(x,y) + p_{BLUE}(455nm) \cdot F_{NADH}^{325nm \to 455nm} \cdot C_{NADH}(x,y)$ $RGB_{RED}^{280nm}(x,y) = p_{RED}(520nm) \cdot F_{RIBOFLAVIN}^{280nm \to 520nm} \cdot C_{RIBOFLAVIN}(x,y) + p_{RED}(400nm) \cdot F_{TRYPTOPHAN}^{280nm \to 400nm} \cdot C_{TRYPTOPHAN}(x,y)$ $RGB_{GREEN}^{280nm}(x,y) = p_{GREEN}(520nm) \cdot F_{RIBOFLAVIN}^{280nm \to 520nm} \cdot C_{RIBOFLAVIN}(x,y) + p_{GREEN}(400nm) \cdot F_{TRYPTOPHAN}^{280nm \to 400nm} \cdot C_{TRYPTOPHAN}(x,y)$ $RGB_{BLUE}^{280nm}(x,y) = p_{BLUE}(520nm) \cdot F_{RIBOFLAVIN}^{280nm \to 520nm} \cdot C_{RIBOFLAVIN}(x,y) + p_{BLUE}(400nm) \cdot F_{TRYPTOPHAN}^{280nm \to 400nm} \cdot C_{TRYPTOPHAN}(x,y)$

Figure 31

3400 Particle Information Packet Contents

| | | | |
|---|---|---|---|
| 3410 | Packet header | 3412 | Particle ID number |
| | | 3414 | Pointers to packet information |
| | | | |
| 3420 | Particle ID block | 3421 | Time stamp |
| | | 3422 | Particle collection device serial number |
| | | 3423 | Device GPS coordinates |
| | | 3424 | Adhesive-coated tape reel # |
| | | 3425 | X coordinate of particle (along length of tape) |
| | | 3426 | Y coordinate of particle (perpendicular to length of tape) |
| | | | |
| 3430 | Objectives block | 3432 | Application type |
| | | 3434 | Definition of particles of interest |
| | | | |
| 3440 | Status block | 3442 | Completed-measurement status bit-coded status flag |
| | | 3444 | Completed-analysis status bit-coated status flag |
| | | 3446 | Work-in-progress particle classification |
| | | 3448 | Definitive particle classification |
| | | | |
| 3460 | Relationship block | 3462 | Sequence numbers of related particles |
| | | 3464 | Nature of relationship of related particles |
| | | | |
| 3480 | Data block | 3481 | In-situ – Camera sensor data |
| | | 3482 | In-situ – Alternate focus camera sensor data |
| | | 3483 | In-situ – Alternate illumination camera sensor data |
| | | 3484 | In-situ – Alternate tape location camera sensor data |
| | | 3485 | Cloud-data – local weather conditions |
| | | 3486 | Cloud-data – known seasonal pathogens |
| | | 3487 | Remote-viewing – Expert technician notes |
| | | 3488 | Remote viewing – Expert scientist notes |
| | | 3489 | Archive – Microscope image data |
| | | 3490 | Archive – Bio-assay data |
| | | 3491 | Archive – Expert technician notes |
| | | 3492 | Archive – Expert scientist notes |

Figure 34

A particle information packet history

| | |
|---|---|
| 3505 | Create particle information packet |
| 3510 | Store camera sensor data 3481 |
| 3515 | Analyze size |
| 3520 | Analyze shape |
| 3525 | Analyze color |
| 3530 | Transmit packet to cloud software |
| 3535 | Confirm conditions favorable for powdery mildew |
| 3540 | Request alternate focus scan |
| 3545 | Store alternate focus data 3482 |
| 3550 | Refine shape analysis |
| 3555 | Request alternate illumination |
| 3560 | Store alternate illumination data 3483 |
| 3565 | Analyze for new color data |
| 3570 | Cloud software requests human review |
| 3575 | Store technician notes 3487 |
| 3580 | Store & respond to scientist confirmation 3488 |
| 3585 | Inform user of powdery mildew detection |
| 3590 | Archive reel of adhesive coated tape |
| 3595 | Bio-assay of powdery mildew confirmed |

Figure 35

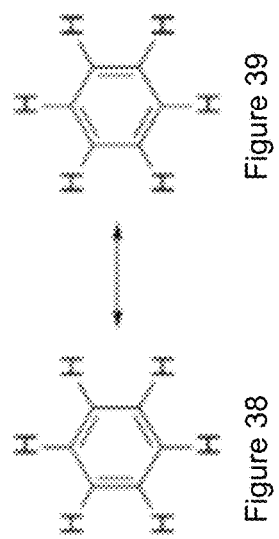
Figure 38 / Figure 39
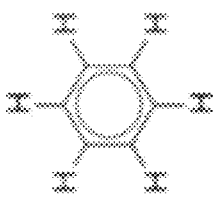
Figure 40
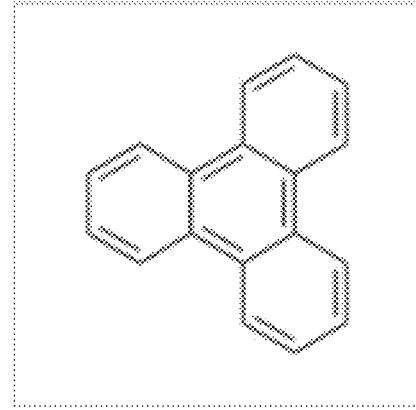
Anthracene
Figure 41
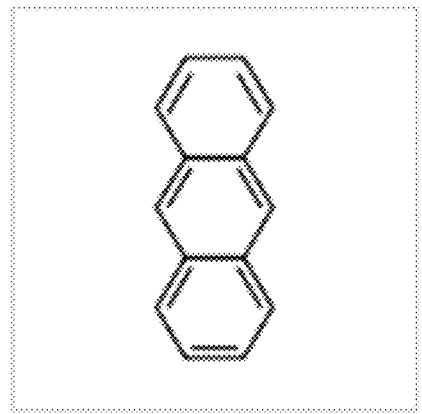
Triphenylene
Figure 42
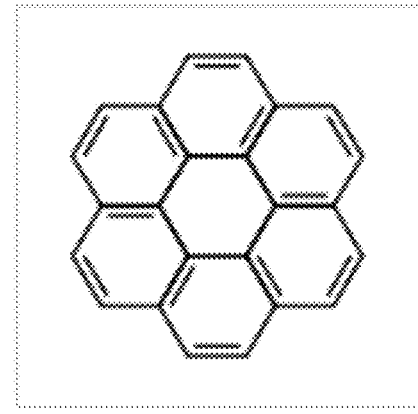
Coronene
Figure 43

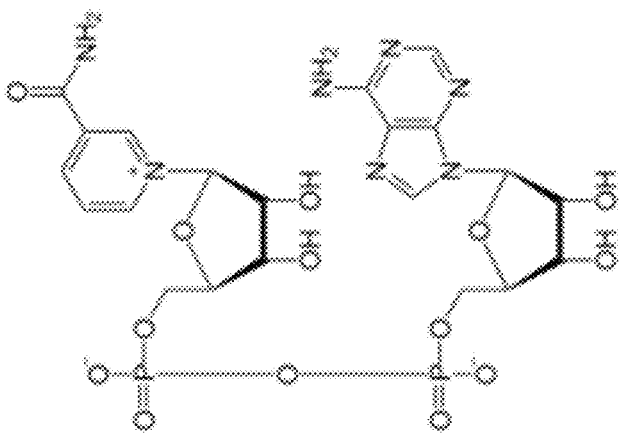
Figure 47 — Nicotinamide adenine dinucleotide
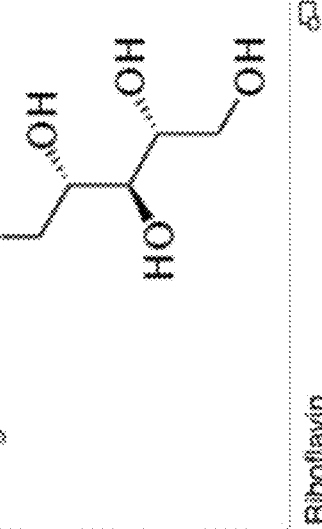
Figure 46 — Riboflavin
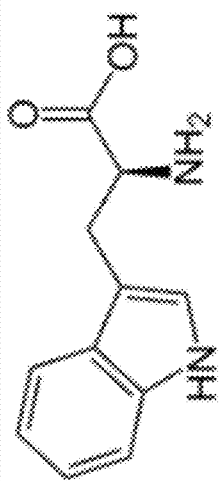
Figure 48 — L-Tryptophan

ID
SPORE STATE DISCRIMINATION

CROSS-REFERENCE TO RELATED APPLICATIONS

This patent application claims the benefit of U.S. provisional patent application 62/370,604, filed Aug. 3, 2016, and is a continuation-in-part of U.S. patent application Ser. No. 15/178,170, filed Jun. 9, 2016, which claims the benefit of U.S. provisional patent applications 62/173,280, filed Jun. 9, 2015, and 62/210,253, filed Aug. 26, 2015, and which is a continuation-in-part of U.S. patent application Ser. No. 15/061,883, filed Mar. 4, 2016, which claims the benefit of U.S. provisional patent applications 62/129,571, filed Mar. 6, 2015, and 62/188,606, filed Jul. 3, 2015, all of which are incorporated by reference along with all other references cited in this application.

BACKGROUND

Minimizing damage from fungal pathogens, such as molds, is of considerable importance to agriculture. There is a need for better methods to promptly detect outbreaks of fungal infections, to monitor the spread of fungal infections, and to track the success of counter measures such as the application of fungicides.

For example, farms and vineyards can suffer from certain types of mold—which is a type of fungus—as winds can carry mold spores for many miles. Depending on climatic conditions, losses for vineyards may range from about 15 percent to about 40 percent or more of the harvest. The loss in harvest results in lost revenue, profit, and jobs. There is a need to cost-effectively and rapidly detect damaging mold spores so that control and mitigation measures can be quickly developed and deployed to save a harvest.

Agriculture has developed various countermeasures to fungal infections of crops, including fungicides. There is interest both in detecting the presence of a fungal infection as well as monitoring the progress of anti-fungal countermeasures.

Identifying the state of a fungal spore, such as whether the spore is virulent or sterile, is important in measuring the success of fungicides. There is, however, a lack of real-time systems and techniques to identify whether or not a fungal spore is virulent or sterile. Further, existing systems and techniques involve very expensive equipment and are thus out-of-reach for many farmers and vintners. For example, techniques using scanning electron microscopy (SEM) or atomic-force microscopy (AFM) are far too time consuming and expensive. When using an optical microscope to view a transparent fungal spore such as *Erysiphe Necator* (aka. Powdery mildew) or *Botrytis* (aka. Gray mold) a user will typically apply a staining dye to enhance the outline of the spore in order to determine the shape (morphology) of the spore; preparing stained spore samples adds undesired cost and delays. Techniques involving the use of fluorescent dyes are also not amenable to automated real-time field measurements. There is a need for improved systems and techniques to quickly and cost-effectively determine the state of a fungal or mold spore.

BRIEF SUMMARY OF THE INVENTION

In an embodiment, there is a method of determining a state of a fungal spore. A flow of air including a fungal spore is directed to a collection cartridge. The fungal spore is trapped within the collection cartridge. The fungal spore is illuminated with visible light and a first image of the fungal spore is captured while the fungal spore is illuminated with the visible light. The first image is analyzed to identify an outline of the fungal spore. The fungal spore is illuminated with ultraviolet (UV) light and a second image of the fungal spore is captured while the fungal spore is illuminated with the UV light. A measurement is made of a degree of fluorescence within the outline of the fungal spore. A state of the fungal spore is determined based on the degree of fluorescence.

In another embodiment, an airborne biological particle monitoring device collects particles floating in air. The monitor includes a camera sensor, illumination source, and distinguishes between different states, such as states of virulence of biological particles including agricultural pathogens. The camera sensor forms part of a highly integrated camera sensor chip package including a pixel sensor array, analog drive and readout circuitry, analog-to-digital conversion circuitry, digital image processing circuitry, and digital communications circuitry.

In another embodiment, a method includes directing a flow of air including a fungal spore to a collection cartridge; trapping the fungal spore on a tape medium of the collection cartridge; positioning the fungal spore within a field of view of a camera sensor while the fungal spore remains trapped on the tape medium of the collection cartridge; activating an ultraviolet (UV) light source to illuminate the trapped fungal spore with UV light; opening a camera shutter associated with the camera sensor for a time period; while the trapped fungal spore is illuminated with the UV light, allowing the camera sensor to collect light emitted from the trapped fungal during a first portion of the time period; after the first portion of the time period has elapsed, directing, during a second portion of the time period after the first portion of the time period, a first burst of white light, originating from a first position, towards the trapped fungal spore; directing, during the second portion of the time period, a second burst of white light, originating from a second position, different from the first position, towards the trapped fungal spore; after the second portion of the time period has elapsed, closing the camera shutter to generate an image; and analyzing the image to obtain a shape of the trapped fungal spore.

BRIEF DESCRIPTION OF THE FIGURES

The patent or application file contains at least one drawing executed in color. Copies of this patent or patent application with color drawing(s) will be provided by the Office upon request and payment of the necessary fee.

FIG. 21C shows an example of state determination results that may be output according to a specific embodiment.

FIG. 21D shows another example of state determination results that may be output according to a specific embodiment.

FIG. 28S shows a graph of fluorescence color characteristics for riboflavin, NADH, and tryptophan.

FIG. 29 shows corresponding biomolecule fluorescence wavelength conversions for the color characteristics shown in FIG. 28S.

FIG. 30 shows a formula for relating measured pixel values "$RGB_i(x,y)$" to the biomolecule distributions "$C_j(x, y)$."

FIG. 31 shows the application of the formula shown in FIG. 30 to the biomolecule fluorescences of FIG. 29.

FIG. 34 shows a block diagram of a particle information packet according to an embodiment.

FIG. 35 shows a block diagram of history for the particle information packet according to an embodiment.

FIG. 38 shows a first representation of planar benzene molecule $C_6H_6$.

FIG. 39 shows a second representation of planar benzene molecule $C_6H_6$.

FIG. 40 shows a third representation of planar benzene molecule $C_6H_6$.

FIG. 41 shows a molecular structure of anthracene.

FIG. 42 shows a molecular structure of triphenylene.

FIG. 43 shows a molecular structure of coronene.

FIG. 46 shows a molecular structure of riboflavin.

FIG. 47 shows a molecular structure of nicotinamide adenine dinucleotide.

FIG. 48 shows a molecular structure of tryptophan.

DETAILED DESCRIPTION

Figure 1:
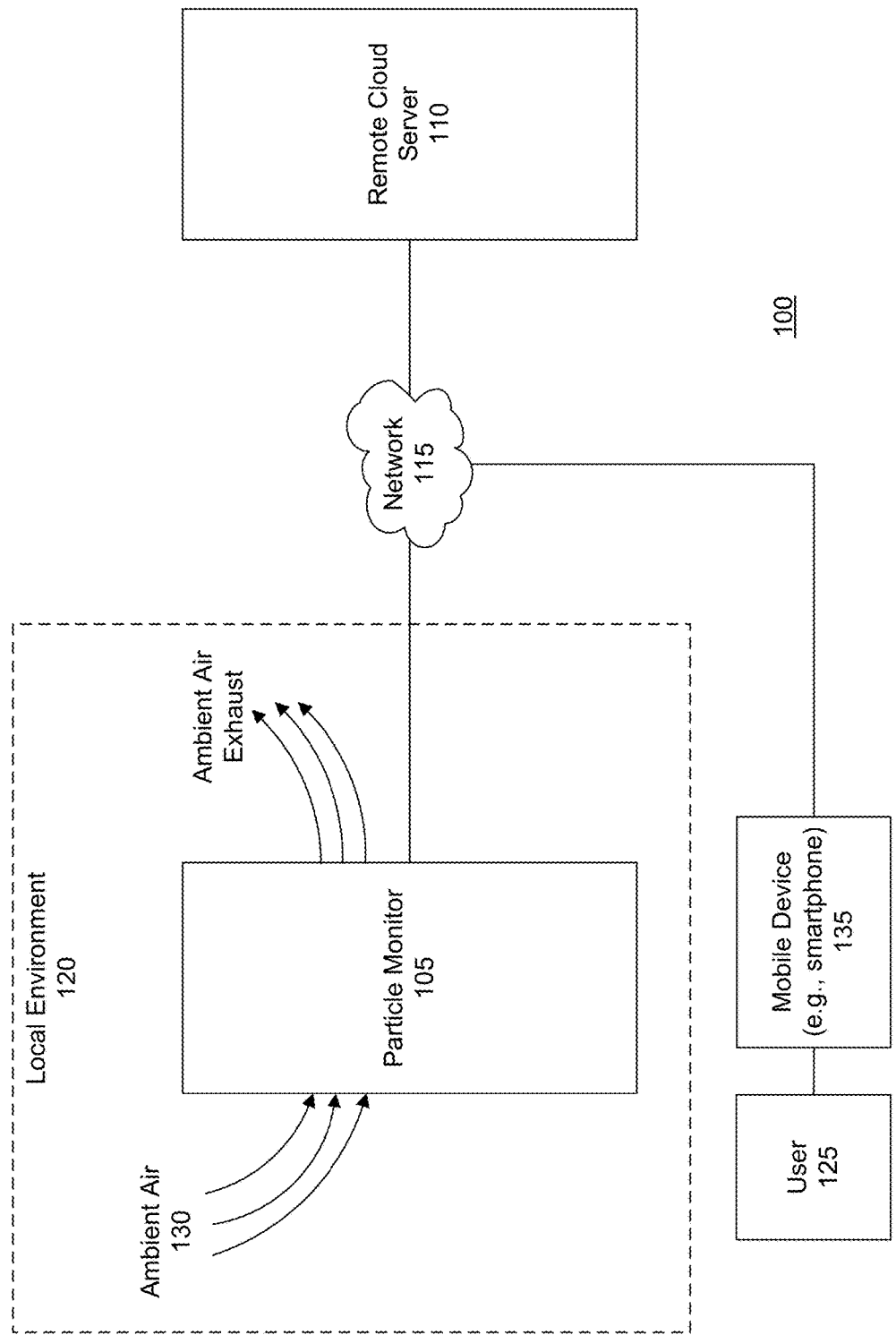
FIG. 1 shows a block diagram of an airborne particle monitoring system according to an embodiment.

FIG. 1 is a block diagram of an airborne particle collection, detection and recognition system 100 according to a specific embodiment. This system addresses unmet needs of the agricultural industry including vineyards for customized and actionable information regarding their crops' exposure to airborne particles such as mold spores, or other airborne particles. An airborne particle monitoring system as illustrated in FIG. 1 addresses needs related to monitoring of air quality as well as monitoring of airborne agricultural pathogens. The latter application is of particular interest to vineyards, farms, and the agricultural industry.

In the example shown in FIG. 1, the system includes an airborne particle monitoring device 105 and a remote cloud server 110 that is connected to the monitoring device via a communication network 115. The particle-monitoring device may be referred to as a particle detector, spore detector, pollen detector, particle collector, spore monitor, pollen monitor, spore collection machine, pollen collection machine, or airborne biological particle monitoring device.

The monitoring device is a device or appliance that is designed to be placed in a local environment 120 where monitoring is desired. In a specific embodiment, the monitoring device is contained within a cylindrical housing having a diameter of about 100 millimeters (mm) and a height of about 150 mm. The device may be placed outdoors in agricultural fields, in vineyards, or other locations where it is of interest to monitor the presence and state of agricultural pathogens such as fungal spores.

Information including alerts and notifications can be sent from the particle monitor, cloud server, or both to a client (e.g., mobile) device 135 of a user 125. The user may be, for example, an agricultural disease management consultant or the owner or manager of a vineyard or farm. In an embodiment, the user can use their mobile device to send instructions or commands to the particle monitor, receive notifications and alerts from the particle monitor, or both. In an embodiment, the particle monitor is a network-enabled device. The user (and their mobile device) can be remote from the particle monitor. For example, the particle monitor may be placed in a vineyard in Napa, Calif. and the user may be in New York, N.Y. The particle monitor can send notifications, alerts, and exchange communications with the mobile device via the network.

An agricultural operation may be susceptible to known pathogens such as powdery mildew. The system shown in FIG. 1 can be used to help identify the specific types of airborne particles such as powdery mildew spores. With this information, a plan for countermeasures can be developed to reduce or eliminate crop infection from agricultural pathogens such as a plan for the targeted application of selected fungicides. In a specific embodiment, the monitoring device samples ambient air 130 and collects or traps airborne particles that may be present or floating in the ambient air.

The monitoring device can use a combination of techniques to analyze, discriminate, and identify the collected particles. In a specific embodiment, the analysis includes capturing images (e.g., pictures, photographs, or snapshots) of the particles under various lighting conditions and examining the captured images. Particles, including different types of spores and pollen, can be identified or discriminated based on their morphology (e.g., shape, surface texture, apertures, or size), color, fluorescence characteristics, or combinations of these as may be captured by a camera sensor of the particle monitor.

In another specific embodiment, the analysis further includes combining the image analysis with context information that is obtained from the remote cloud server. The context information may include, for example, information regarding weather, wind conditions, humidity levels, the types of spores and pollen currently propagating at the geographical location of the collected particles, vegetation known to be present at the geographical location of the collected particles, other context information, or combinations of these.

For example, in a specific embodiment, a particle monitoring device generates a set of candidate particle identifications for a particular particle that has been captured based on analyzing a set of images taken of the captured particle. After the set of candidate identifications have been generated, the particle monitoring device issues a request to the cloud server for context information. The request can include a geographical location of the particle monitoring device, time and date of particle capture, or both. The cloud server receives the request and uses the geographical location of the monitoring device, time and date of capture, or both to retrieve appropriate or relevant context information to transmit to the monitoring device.

The monitoring device receives the appropriate context information and further analyzes the context information in conjunction with the set of candidate particle identifications. Consider, as an example, that particles are identified as powdery mildew spores, but by itself the monitoring device cannot identify which of several species of powdery mildew has been detected. If, however, the context information received by the particle monitor from the cloud server indicates that only one of the many species of powdery mildew is currently propagating in agricultural fields at the geographical location of the monitoring device, the analysis may conclude that the species detected is the species known to be propagating in the geographical area.

The images of the particles captured by the monitoring device may be transmitted or sent to the remote cloud server for further analysis. The analysis may include a review of the images by a human technician. For example, in some cases, an automated image analysis and context information analysis may not lead to a satisfactory identification. In these cases, the analysis may be escalated to a human technician. In particular, the images, associated metadata, or both can be transmitted to the cloud server for review by a human technician. The associated metadata can include the geographical location of the particle monitor, time and date of particle capture, or both.

In a specific embodiment, the particle monitoring device traps the airborne particles on a piece of media or medium that can be removed by the user from the particle monitoring device. The media, with trapped airborne particles, may additionally be transported to a lab for an in-depth analysis. Consider, as an example, that the human technician is unable to identify with reasonable certainty the particle from the images. The technician can escalate the analysis to an analysis of the actual collected particle. In particular, the technician can notify the user that the collection media should be removed from the particle monitoring device and delivered to a laboratory for an analysis of the actual collected physical particles. For example, the technician may transmit through the system a notification to an app executing on the user's mobile device. The app may display the message, "Please remove particle collection media from your particle monitor and deliver it to our laboratory for analysis."

This technique of escalation is an example of what may be referred to as tiered particle analysis. Such an analysis helps to ensure judicious use of resources including computing resources (e.g., network bandwidth, storage) and human labor. Activities such as accessing a network, sending image files over the network, human review, delivering the physical particles, and so forth consume resources. For example, an image file may be several megabytes in size. It can be desirable to refrain from transmitting the image file over a network unless the transmission is deemed necessary.

In a specific embodiment, there is a first attempt to identify the collected particles where the first attempt is performed locally (e.g., at the particle monitor). If the first attempt fails to result in a satisfactory identification, a second attempt includes accessing a remote cloud server to obtain over a network context information. If the second attempt fails to result in the satisfactory identification, a third attempt includes transmitting over the network the image files to the remote cloud server for human review. If the third attempt fails to result in the satisfactory identification, a fourth attempt includes instructing the user to mail the removable media with collected particles to a laboratory.

In a specific embodiment, the particle monitoring device is paired with one or more mobile devices 135 associated with or belonging to the user such as an agricultural disease management consultant. The pairing allows the particle monitoring device and mobile device to exchange information, instructions, data, commands, or other communications.

Mobile devices include, for example, smartphones, tablet computers, and wearable computers (e.g., Apple Watch, Google Glass). Mobile devices 135 are not limited to consumer products and also may include airborne drones and automated land-based vehicles. For example, a number of particle monitoring devices may be located at various positions within a cultivated field. An airborne drone may do a survey of the cultivated field and detect a possible issue in the vicinity of one of the particle monitoring devices. The drone may then fly in close proximity to that specific particle monitoring device and wirelessly collect data that has accumulated in the particle monitoring device.

Conversely, a particle monitoring device may detect a pathogen of concern and activate a beacon signal that causes a drone to fly by to collect data accumulated in the particle-monitoring device as well as to survey the portion of the cultivated field in proximity to the particle-monitor device for possible signs of crop damage. Similarly, particle monitoring devices may interact with automated land-based vehicles. Both airborne drones and autonomous land-based vehicles may be equipped with sprayers and may be programmed to spray fungicides in the vicinity of particle-monitoring devices that have detected a level of pathogenic spores exceeding some preprogrammed threshold. Mobile devices 135 may be any generalized to any interacting set of mobile devices, fixed devices, or both that are in communication with one or more particle monitoring devices.

In a specific embodiment, a method includes sending data to airborne drones, automated land-based vehicles, or both. There can be a drone that does a survey of land and detects possible issues and wants to get a read of particle readings, or vice versa. That is, the particle monitoring device may detect continuous high particulate in the vicinity and may send data to a drone that will then perform a survey of a larger area.

Similarly, data could be sent to an autonomous land-based sprayer that may decide to come in a spray based on some preprogrammed thresholds of particles over time. In one embodiment, a method includes deploying one or more particle monitors to monitor a cultivated field, configuring for a particle monitor a threshold including a number pathogen detections over a period of time, detecting, at the particle monitor, a set of pathogens of concern over the period of time, and if a number of the set of pathogens of concern exceeds the threshold, activating, at the particle monitor, a beacon signal, where the beacon signal is to be received by an autonomous vehicle.

The autonomous vehicle may include a tank holding a pesticide, and a sprayer to spray at least a portion of the cultivated field with the pesticide upon receipt of the beacon signal by the autonomous vehicle. The autonomous vehicle may include an airborne drone configured to survey at least a portion of the cultivated field upon receipt of the beacon signal by the autonomous vehicle. The autonomous vehicle may include an airborne drone. The autonomous vehicle may include a land vehicle.

In another specific embodiment, a method includes deploying one or more particle monitors to monitor a cultivated field, receiving at a particle monitor a command from an autonomous vehicle, and upon receipt of the command from the autonomous vehicle, sampling by the particle monitor ambient air.

Figure 2:
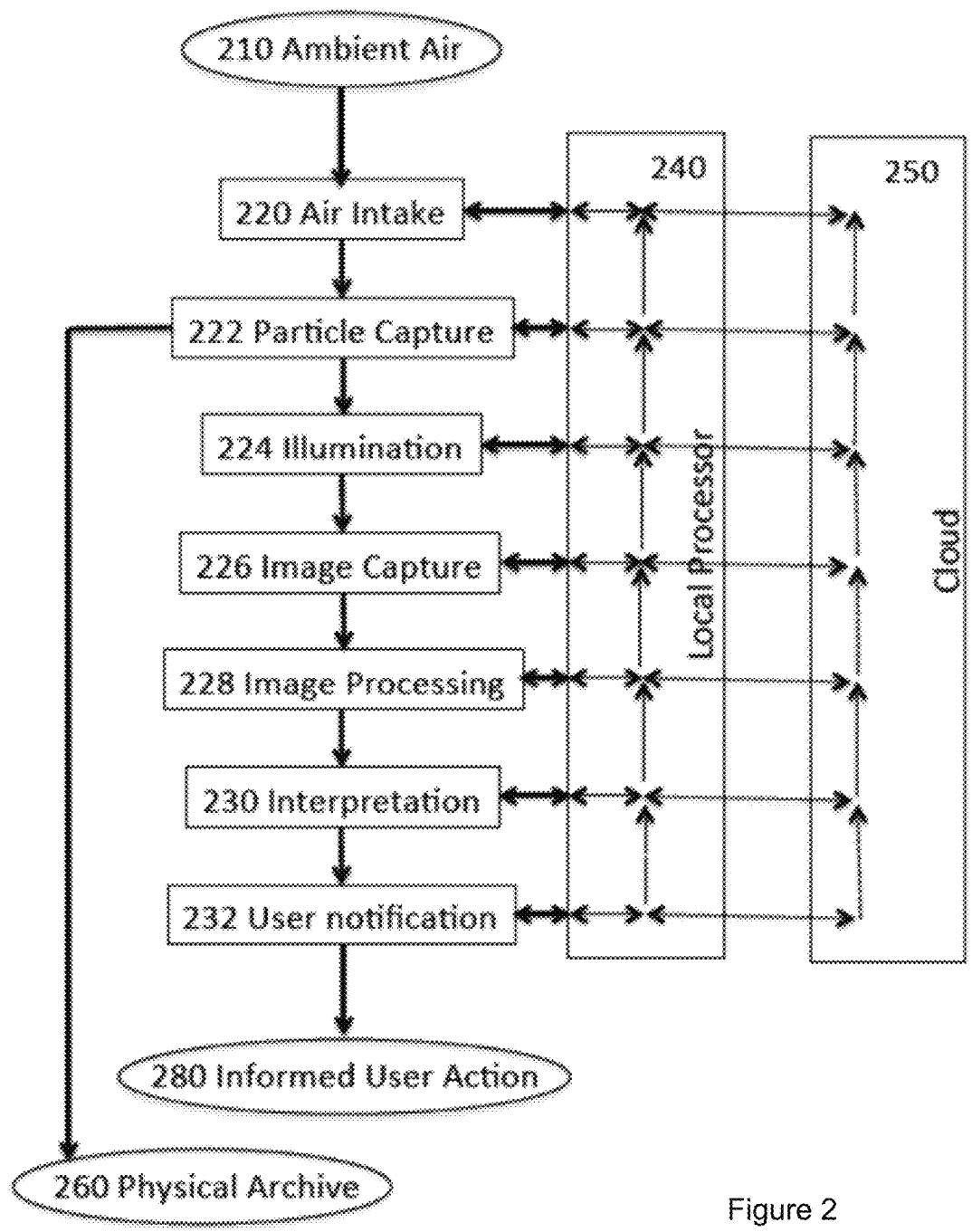
FIG. 2 shows another block diagram of an airborne particle monitoring system according to an embodiment.

FIG. 2 is a block diagram showing some elements and processes of an airborne particle collection, detection, and recognition system 200 according to a specific embodiment. Airborne particle monitoring system 200 includes air intake hardware 220 to sample ambient air 210, particle-capture hardware 222 with which particles removed from ambient are collected and transported for microscopic analysis. The microscope system includes illumination hardware 224 that shines visible, ultraviolet (UV), or infrared (IR) light, or combinations of these on captured particles, and image-capture hardware 226 that may include a lens assembly as well as a camera sensor. The light may include light emitted from quantum dots. Capturing various images of the particles when illuminated under different conditions provides for additional dimensions of analysis to help identify, classify, or discriminate between the collected particles.

Image processing software and hardware 228 processes image data from the image-capture hardware 226. The types of the observed particles are then decided by interpretation software 230. Finally, user-notification software 232 outputs the interpretation results in a form that can be understood by the user. For example, the output may include displaying on an electronic screen a message specifying the airborne particles that have been collected and identified. The value of airborne particle monitoring system 200 can be realized when it beneficially guides the user to take an informed user action 280.

In some embodiments, particle-capture hardware 222 provides for a medium that can be removed with captured particles and archived for possible future laboratory inspection, thus providing a physical archive 260 of captured particles.

The actions and data processing of airborne particle monitoring system 200 is orchestrated through a local processor 240. Local processor 240 is preferably supported by other computing and data resources via digital communication networks that may concisely be referred to as the "cloud"; see, e.g., cloud server of FIG. 1.

Local processor 240 and cloud 250 may support numerous feedback loops. Here is one example. Interpretation software 230 (which may be code executed in a dedicated processor, or by the local processor, or on the cloud) may be unable to reach a definitive result and the system may respond by requesting ultraviolet light illumination from the illumination hardware 224 in order to generate additional fluorescence spectral information.

In an embodiment, the image capture hardware 226 is based on an imaging sensor designed for use in color cameras. The mass market for digital cameras, including those in smartphones, has resulted in very capable color camera sensors at relatively low prices. Such color camera sensors, such as the SON-IMX028 CMOS image sensor by Sony, provides at low cost rich data for particle detection and discrimination. Furthermore, the spectral richness of data collected with a color camera sensor may be extended by enhancing the capabilities of the illumination hardware 224; more details are given further below. The use of color camera sensors in combination with enhanced illumination hardware is advantageous for the goal of providing a capable airborne particle monitoring system 200 in a competitive price.

It is of interest to note that the low-cost of such color camera sensors is not just a matter of high manufacturing volumes, but also the high degree of integration of the products. One example of a highly integrated and low-cost color camera sensor suitable for use with the particle monitor is SONY's SON-IMX028 CMOS image sensor as provided by Sony Corporation of Tokyo, Japan. Such highly-integrated RGB camera sensors include within their chip package not only the RGB pixel sensor itself, but also associated analog drive and readout circuitry, analog-to-digital conversion circuitry, digital circuitry for image capture and processing as well as digital electronics sufficient to output images in a digital format to an external main processor.

Figure 3:
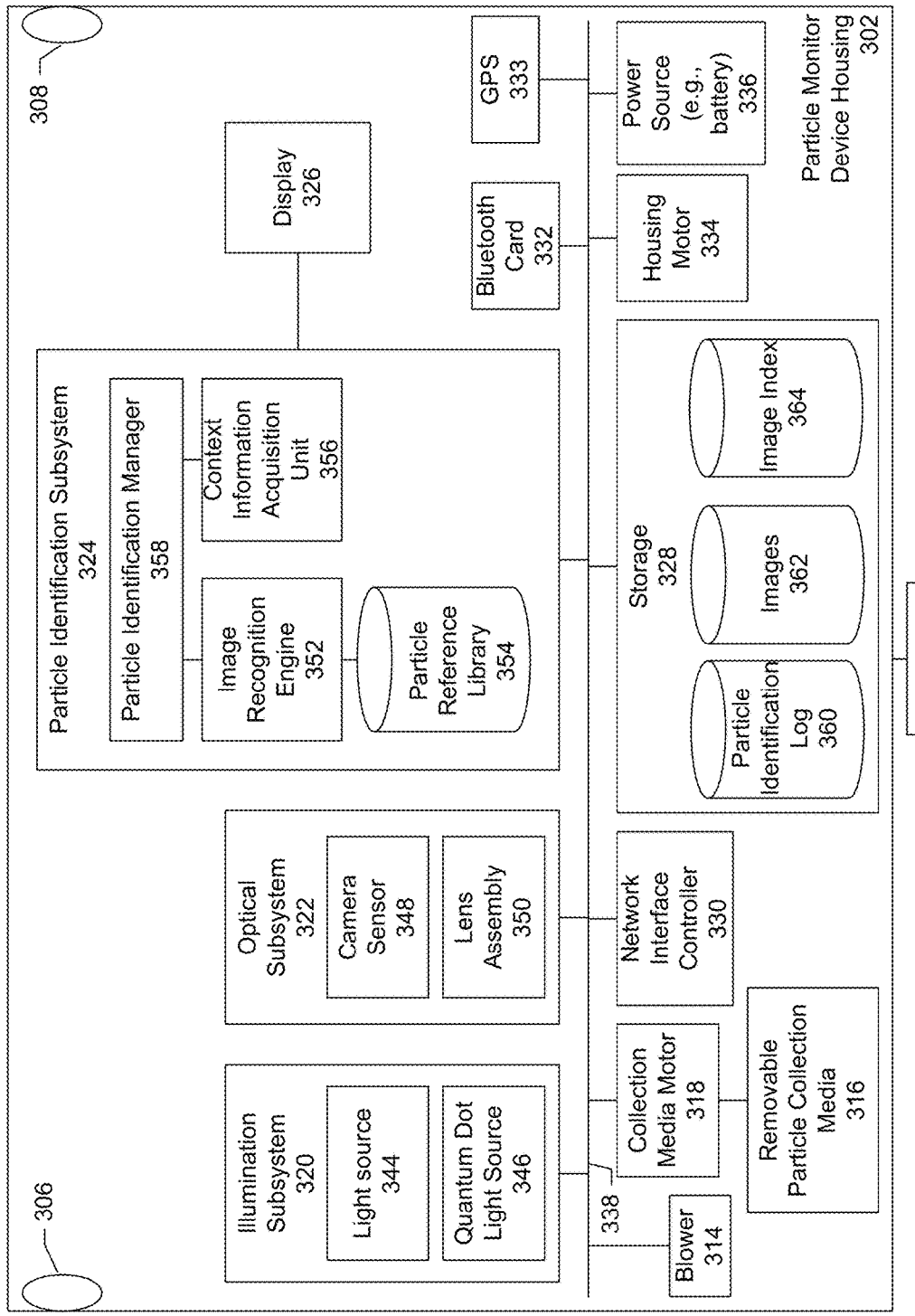
FIG. 3 shows a block diagram of an airborne particle monitor according to one embodiment.

FIG. 3 shows a block diagram of particle monitoring device 105 according to one embodiment. The block diagram shows a number of subsystems, processing modules, and components that can be included in the particle monitoring device. In an embodiment, the particle monitoring device includes quantum dots. The quantum dots are configured emit light having spectral characteristics corresponding to a particle of interest. Particles collected by the monitoring device are illuminated under the light emitted by the quantum dots and a color image (e.g., picture, photograph, or snapshot) is taken while the particles are illuminated by the quantum dots. The image can be analyzed to determine whether the image includes the particle of interest.

The particle monitoring device shown in FIG. 3 includes a device housing or enclosure 302 and a base 304, connected to the housing. The housing includes an air intake opening 306 and an air exhaust opening 308. Contained within or inside the housing is a blower 314, removable particle collection media 316, collection media motor 318, illumination subsystem 320, optical subsystem 322, particle identification subsystem 324, display 326 connected to the particle identification subsystem, storage 328, network interface controller 330, Bluetooth communication card 332, global positioning system (GPS) sensor 333, housing motor 334, and power source (e.g., battery) 336. There can be a user-operable power switch so that the device can be turned on, turned off, placed in a standby state, or combinations of these.

The subsystems, processing modules, components and so forth are connected by a bus system 338. The power source provides electrical power to the subsystems, processing modules, and components. The power can be DC power such as that provided by a battery. Using a battery to supply power facilitates a particle monitor that may be placed in an outdoor environment such as an agricultural field. A particle monitor may include a set of solar cells for recharging the battery. In another specific embodiment, the power can be AC power.

The blower is responsible for moving ambient air outside the monitor device housing, through the air intake opening, into the monitor device housing, towards the collection media, and then out through the air exhaust opening. The blower may be referred to a fan.

The removable particle collection media provides a medium for trapping particles that are airborne or floating in the ambient air. In a specific embodiment, the collection media includes an adhesive tape. The tape is flexible so that it can be mounted on or wound upon on a reel or spool. The adhesive tape includes a backing material and an adhesive that is applied to a side of the backing material. The backing material can be made of paper, plastic, plastic film, fabric, polyester, Teflon, nylon, cloth, metal foil, or any other competent material. The adhesive can be any type of adhesive that can trap particles floating in the ambient air. The adhesive may include glue, paste, mastic, rubber cement, or other sticky or tacky substance. The blower directs the flow of air towards or over the collection media. Particles within the air are then trapped by the adhesive-coated side of the tape.

In a specific embodiment, the tape is 3M polyester film tape 850 as provided by 3M Corporation Maplewood, Minn. Applicants have discovered that this particular tape includes features desirable for a particle monitor. In particular, the polyester film includes a wide temperature range resistance (e.g., −50 degrees Celsius to 177 degrees Celsius) which helps to reduce failure caused by film shrinkage or embrittlement. The wide temperature range resistance is desirable because in some embodiments, the monitor device is used outdoors and thus must survive wide temperature fluctuations throughout the day and times of the year. For example, temperatures typically drop during the night and rise during the day. Applicants have discovered that for applications of particle monitoring the tape shows desirable, long lasting resistance to cyclic fatigue. This means the tape can be pulled off and coiled again multiple times to re-examine trapped particles again and again and the tape still retains very good adhesion.

In a specific embodiment, the adhesive on the tape includes an acrylic adhesive. This is advantageous because it is not water-based and thus can better survive outdoor environments. For example, outdoor environments can be more subject to moisture as compared to indoor environments. An acrylic adhesive can tolerate moisture better than a water-based adhesive. In a specific embodiment, the tape includes a polyester film. Properties desirable in the polyester film—including its wide temperature range—is that it can be made very thin, possesses very high strength, has high moisture resistance, and is resistant to chemicals and solvents (e.g., will not decompose easily if chemicals or solvents floating in the air should fall on the tape).

It should be appreciated that 3M polyester film tape 850 is merely one example of a tape suitable for use with the particle monitor and in other embodiments, other tapes with properties desirable for the particle monitor may instead be used. For example, 3M film tape 850 includes an adhesion to steel specification according to ASTM test method D-3330 of 31.5 N/100 mm. The collection media motor is designed with sufficient power to advance and uncoil the tape. Applicants have found that a lower adhesion to steel value can be desirable (e.g., about 15.7 N/100 mm) because less power is required to advance and uncoil the tape.

In a specific embodiment, a color of the tape is black or a dark color. An advantage of using black or a dark color is that light is less likely to reflect or bounce off the tape as compared to lighter colors (e.g., white). For example, a technique of the system includes capturing images of the particles under different specified illumination conditions. Light (e.g., white light) bouncing off the tape and into the camera sensor may skew the images and, in particular, the colors captured in the images. In another specific embodiment, the tape is transparent or at least partially transparent. A transparent tape allows for backside illumination (e.g., illuminating from below the tape).

In a specific embodiment, a removable cartridge is provided which houses the adhesive coated tape. The cartridge houses a supply reel, an uptake reel, and the adhesive coated tape. An end of the tape is connected to the supply reel. An opposite end of the tape is connected to the uptake reel. The adhesive coated tape is wound upon the supply reel and spent portions of the tape upon which particles have been trapped are wound onto the uptake reel. The cartridge may further include an identification tag such as a radio frequency identification tag (RFID) tag, machine-readable code (e.g., barcode, quick response (QR) code), or other label. Depending upon the type of tag, the tag may be attached to a body of the cartridge (e.g., via glue), or printed onto the body of the cartridge. The particle monitor may include a corresponding reader. The identification tag allows the particle monitor to uniquely identify the cartridge.

In another specific embodiment, the collection media includes a rigid disc. A side of the disc is coated with an adhesive to trap the airborne particles that enter the monitoring device. The disc exposes different regions around an annulus so that particles are trapped within a particular region. The disc may be made of plastic, nylon, metal, or any other rigid material. In another specific embodiment, the collection media includes adhesive-coated glass slides. In each embodiment, the adhesive coated tape (or other particle collection media such as adhesive-coated glass slides or adhesive-coated disc) may be removed from the particle collection device and fresh media inserted into the particle collection device. Anywhere a glass slide may be used, a plastic slide is likely to be an equally viable option. Removed media containing captured particles may be subjected to laboratory inspection and testing, archived for possible future laboratory inspection and testing, or both.

The collection media motor is responsible for advancing the collection media. For example, in an embodiment, the collection media includes a cartridge having a supply reel, an uptake reel, and an adhesive coated tape wound about the supply reel and connected to the uptake reel. Upon collecting some airborne particles on a portion of the adhesive coated tape, the media motor can advance the tape so that new particles can be trapped on another portion of the adhesive coated tape. The portion having the previously trapped airborne particles can be advanced to the particle identification subsystem for imaging and examination.

The collection media motor may include a counter that tracks a position of the tape. The position of the tape can be associated with the image. Storing the position information allows the tape to be later advanced (or unwound) to the same position at which the image was taken and additional analyses to be performed. The counter may count a number of units between a reference point on the tape (e.g., a beginning of the tape or an ending of the tape) and a location of the tape at which the image was taken. The units may be distance-based. For example, the location of the tape may be a distance as measured from the beginning of the tape.

The illumination subsystem includes various optical elements for generating and emitting light or radiation (e.g., visible light, ultraviolet light, infrared, or combinations of these) into the particles that have collected on the collection media. The illumination subsystem includes one or more light sources (e.g., two light sources). Each light source includes one or more light emitting elements.

In a specific embodiment, a lighting element includes a light emitting diode (LED). A light source may include a cluster of light emitting elements such as a cluster of LEDs (e.g., two or more LEDs). A cluster may include any number of light emitting elements such as LEDs. For example, a cluster may include one, two, three, four, five, six, seven, eight, or more than eight LEDs. In another specific embodiment, a lighting element includes a laser diode. There can be a combination of different types of light emitting elements such as a combination of LEDs and lasers.

The illumination subsystem may include lenses, filters, diffusers, or combinations of these for directing or modifying the light as desired. For example, a diffuser may be used to spread out the light from a lighting element and provide a soft light. A diffuser can help to ensure that the area around the collected particles is illuminated. In a specific embodiment, the illumination system includes optical fiber. The optical fiber can be used to collect light emitted by a light source and direct the light onto the collected particles. Optionally, the illumination system may also include polarizers or light sources that are inherently polarized.

In an embodiment, the illumination subsystem includes a first light source 344, and a second light source 346. In an embodiment, at least one of the first or second light sources is an ultraviolet light source (e.g., radiation wavelengths ranging from about 10 nm to about 380 nm). For example, an ultraviolet light source may include an LED with a characteristic emission wavelength of 365 nm. This is a relatively long ultraviolet wavelength with sufficient photon energy to excite fluorescence in flavin molecules but few other biomolecules. Additional ultraviolet light sources of shorter wavelengths and higher photon energies may be provided that induce fluorescence in additional biomolecules.

The optical subsystem includes various optical elements for capturing one or more images of the collected particles while the collected particles are being illuminated or radiated by the illumination subsystem. In an embodiment, the optical subsystem includes a microscope including a camera sensor 348 and lens assembly 350. A microscope is an optical instrument having a magnifying lens or a combination of lenses for inspecting objects too small to be seen or too small to be seen distinctly and in detail by the unaided eye. The lens assembly includes a set of lenses for bringing the collected particles into focus, magnifying the collected particles, or both. The camera sensor collects light scattered or reflected, or fluorescently re-emitted, back from the particles to capture images or photographs. Optionally the optical subsystem may include one or more polarizers so that images may be captured for light of known polarization.

The particle identification subsystem includes an image recognition engine 352, particle reference library 354, and context information acquisition unit 356. A particle identification manager 358 manages the particle identification or discrimination process.

The particle reference library stores reference information identifying different types of airborne particles. In a specific embodiment, the reference information includes particle-discrimination algorithm parameters. Optionally, these particle-discrimination algorithm parameters are determined by machine learning algorithms and a learning set of reference files that includes images including color photographs, fluorescence images, or both of different types of known particles. The machine learning algorithms that determine the particle-discrimination algorithm parameters may run locally, on the cloud, or both. Running the algorithms in the cloud helps to reduce the cost of computing hardware in the local device. Being able to run the algorithms locally at the particle monitor can be advantageous in environments where there is limited network connectivity. The set of learning files may include reference images of mold spores, pollen, and other particles of interest. Table A below shows an example of a data structure that may be used to store the reference information.

TABLE A

| Filename | Description |
| --- | --- |
| powdery_mildew_spores.jpg | Picture of powdery mildew spores. |
| Botrytis_spores.jpg | Picture botrytis spores. |
| ... | ... |

A first column of the table is labeled filename and lists the various files stored in the particle reference library. A second column of the table includes metadata (e.g., a description) that identifies the object in the corresponding file.

In an embodiment, the image recognition engine receives the image of the collected particles taken by the optical subsystem and analyzes the image using particle-discrimination algorithm parameters it previously received from the cloud. For example, particle-discrimination algorithms running in the particle identification subsystem may identify the collected particle as a spore of the pathological vineyard mold spore *botrytis*.

Some examples of parameters that may be considered in a particle-discrimination algorithm include autofluorescence properties (e.g., intensity of autofluorescence), size, shape, length of polar axes, length of equatorial axes (or diameter), ratio of polar axis to equatorial axis (P/E ratio), number of apertures, type of apertures, shape of apertures, position of apertures, lack of apertures, color characteristics, geometrical features, type of symmetry (e.g., radial symmetry or bilateral symmetry), lack of symmetry, other parameters, weights, or combinations of these. One or more of these parameters may be derived or extracted from optical system measurements, specified as a threshold, and then used as a discrimination algorithm parameter to discriminate particles.

The image recognition engine may use any competent technique or combination of techniques for recognizing the particles imaged by the optical subsystem. Some examples of image recognition techniques include edge detection, edge matching, changes in color, changes in size, changes in shape, divide-and-conquer searches, greyscale matching, gradient matching, histograms of receptive field responses, large model bases, interpretation trees, hypothesize and test, post consistency, pose clustering, invariance, geometric hashing, scale-invariant feature transform (SIFT), and speeded up robust features (SURF), among others.

The context information acquisition unit is responsible for obtaining context information associated with the particles that have been collected by the monitoring device. The context information may be based on a geographical location of the collected particles, a time and date of the collection, or both. In an embodiment, the context information includes known agricultural pathogens recently detected in one or more various particular geographical areas. For example, if a short list of species of powdery mildew is known to infect vineyards in Napa Valley, then a particle monitor located in a vineyard in Napa Valley may be provided with this list. The context information may include weather conditions, temperature, wind speed, wind patterns, and so forth.

The context information may include a listing of particle types that have been identified by other nearby particle monitors, mobile drones, or both. For example, nearby particle monitors may include particle monitors that are within a specified radius of the requesting particle monitor. The radius may be, for example, 50, 100, 500, 1000, 2000, or more than 2000 meters. The radius may be less than 50 meters. The radius may be configurable such as by a user or administrative user. The radius may be determined dynamically. For example, the radius may vary proportionally to current wind speed as high winds can increase the likelihood of particles being carried into the local environment from remote areas.

The context information is used by the particle identification subsystem to help narrow the list of candidate particle types. Results of the particle identification subsystem may be outputted to the display, recorded in a log, or both.

The storage may include a particle identification log 360, images repository 362, and image index 364. The particle identification log records identifications of particles as determined by the particle identification subsystem. Table B below shows an example of information that may be recorded in the log.

TABLE B

| Image File | Context Info File | Particles Present | Timestamp | Location |
| --- | --- | --- | --- | --- |
| 001.jpg | Context1.txt | Grass pollen | Apr. 10, 2016, 11:34 AM | 45 Appleseed Drive, Santa Rosa, CA 94555 |

TABLE B-continued

| Image File | Context Info File | Particles Present | Timestamp | Location |
|---|---|---|---|---|
| 002.jpg | Context2.txt | Grass pollen | Apr. 10, 2016, 1:36 PM | 45 Appleseed Drive, Santa Rosa, CA 94555 |
| 003.jpg | Context3.txt | Botrytis spores | Apr. 11, 2016, 2:00 PM | 45 Appleseed Drive, Santa Rosa, CA 94555 |

In the example shown in table B above, a first column of the table lists the name of the file containing the image of the collected particles. A second column lists the name of the file containing the context information that may be associated with a geographical location of the collected particles, time and date of the collected particles, or both. The context information may be formatted as a text file, Extensible Markup Language (XML) formatted file, or in any other file format as desired. A third column identifies type(s) of particle(s) of interest. A fourth column of the table stores a timestamp indicating a time and date that the particles were collected. A fifth column of the table stores a location of the particle collection.

It should be appreciated that the data shown in table B above is merely an example of some of the metadata information associated with particle identification that may be stored in the database. In a specific embodiment, a particle information packet and particle information packet history is stored. Further details are provided below.

The images repository stores the image files generated by the optical subsystem. The files store digital images of the particles that have been captured. The files may include raw image files (e.g., digital negatives), raster images, bitmapped images, or combinations of these. The files may be formatted using any type of image file format (e.g., jpeg, exif, tiff, gif, bmp, png, and so forth).

The image index database stores metadata associated with the image files. The metadata may include, for example, image filenames, time and date that the image was taken, geographical location data, optical settings, and so forth. The metadata may include a description or specification of the lighting conditions, as provided by the illumination subsystem, under which the images were made. For example, the metadata may indicate that a first image was taken while particles were illuminated by white light, a second image was taken while the particles were illuminated by red light emitted from quantum dots, a third image was taken while the particles were illuminated by ultraviolet light, a fourth image was taken while the particles were illuminated by infrared light, and so forth. The index can be accessed and searched.

In a specific embodiment, the particle identification log, particle image files, image index, or combinations of these are transmitted from the particle monitor to the cloud server for further review, archival storage, backup. For example, the particle image files may be transmitted to the cloud server periodically or in batch such as nightly, weekly, or at any other frequency or time as desired. Once the image files have been transmitted to the cloud server, the image files may be deleted from the particle monitoring device. Deleting the images from the particle monitoring device frees up storage space for new images.

The GPS sensor provides geographical location information. The geographical location information allows the images of the collected particles to be tagged with the location of collection. As discussed, the location information is used to obtain context information such as fungal species currently propagating at the geographical location of collection, weather conditions, identify other nearby particle monitors, or combinations of these.

The Bluetooth communication card or chip allows for a wireless pairing of the particle monitor and a user's mobile device. Bluetooth includes a communication protocol that allows for communicating over short distances (e.g., about 10 meters). The wireless pairing allows the particle monitor device and mobile device to exchange communication and other information. For example, in a specific embodiment, the particle monitor transmits to the mobile device a message including an identification of a particle that was collected. It should be appreciated that Bluetooth is merely one example of a standard for wireless communication. Other embodiments may include other communication standards in addition to or instead of Bluetooth such as WiFi. The particle monitor may include a radio transmitter and antenna for long distance communication.

A power subsystem of the particle monitor may include a low-battery indicator unit. When the available battery power drops below a threshold (e.g., 20 percent battery remaining), the low-battery indicator unit can transmit a notification such as text message notification to the user's mobile device to notify the user that the particle monitor should be recharged.

The housing motor turns or rotates the particle device housing about the base. The turning allows the air intake opening to pull in ambient air from different directions so that there is a good or representative sampling of air. The housing motor can be used to ensure that the air intake openings are aligned with a direction of wind so that airborne particles in the wind will enter through the air intake opening.

In a specific embodiment, the power source includes one or more batteries. The battery may be a rechargeable battery. Examples of rechargeable batteries include nickel cadmium (NiCd) batteries, nickel metal hydride (NiMH) batters, lithium ion (Li-ion) batteries, and others. When the rechargeable battery within the particle monitor is depleted, the batteries may be recharged by an AC adapter and cord that may be connected to the particle monitor. Alternatively, batteries may be recharged with energy from solar panels. In other words, in an embodiment, the particle monitor does not necessarily require AC power to recharge. In this embodiment, the particle monitor device may be powered in the field using solar panels and a rechargeable lead-acid battery. In this specific embodiment, there can be a controller that regulates the solar panels load into the battery and into the device.

Instead or additionally, the particle monitor may include a universal serial bus (USB) port. The USB port allows the particle monitor to be connected to a computer such as a desktop computer for charging. The port may also be used to configure the particle monitor via the desktop computer, transfer data from the particle monitor to the desktop computer, transfer data from the desktop computer to the particle monitor, or combinations of these. In another specific embodiment, the power source includes one or more disposable batteries.

The network interface controller provides the gateway to communicate with the mobile device, server, or both. In an embodiment, the network interface is connected to the Internet. The network interface controller may include an antenna for wireless communication, an Ethernet port to connect to a network via a cable, or both.

The housing may be made from a material such as plastic, nylon, metal, wood, or combinations of these. In a specific embodiment, the housing is made of plastic. A non-conductive material such as plastic is desirable because a plastic housing allows for the passage of radio waves so that the particle monitor can communicate wirelessly. For example, an antenna located inside a plastic housing will be able to receive and transmit wireless signals through the plastic housing. Plastic is also relatively inexpensive to form and manufacture. In other cases, however, a metal housing may be desired. Metal can be less likely to crack as compared to plastic and users may prefer the aesthetic appearance of metal. In embodiments where the housing is made of metal, the antenna may be located or embedded on an outside surface of the housing.

Figure 4:
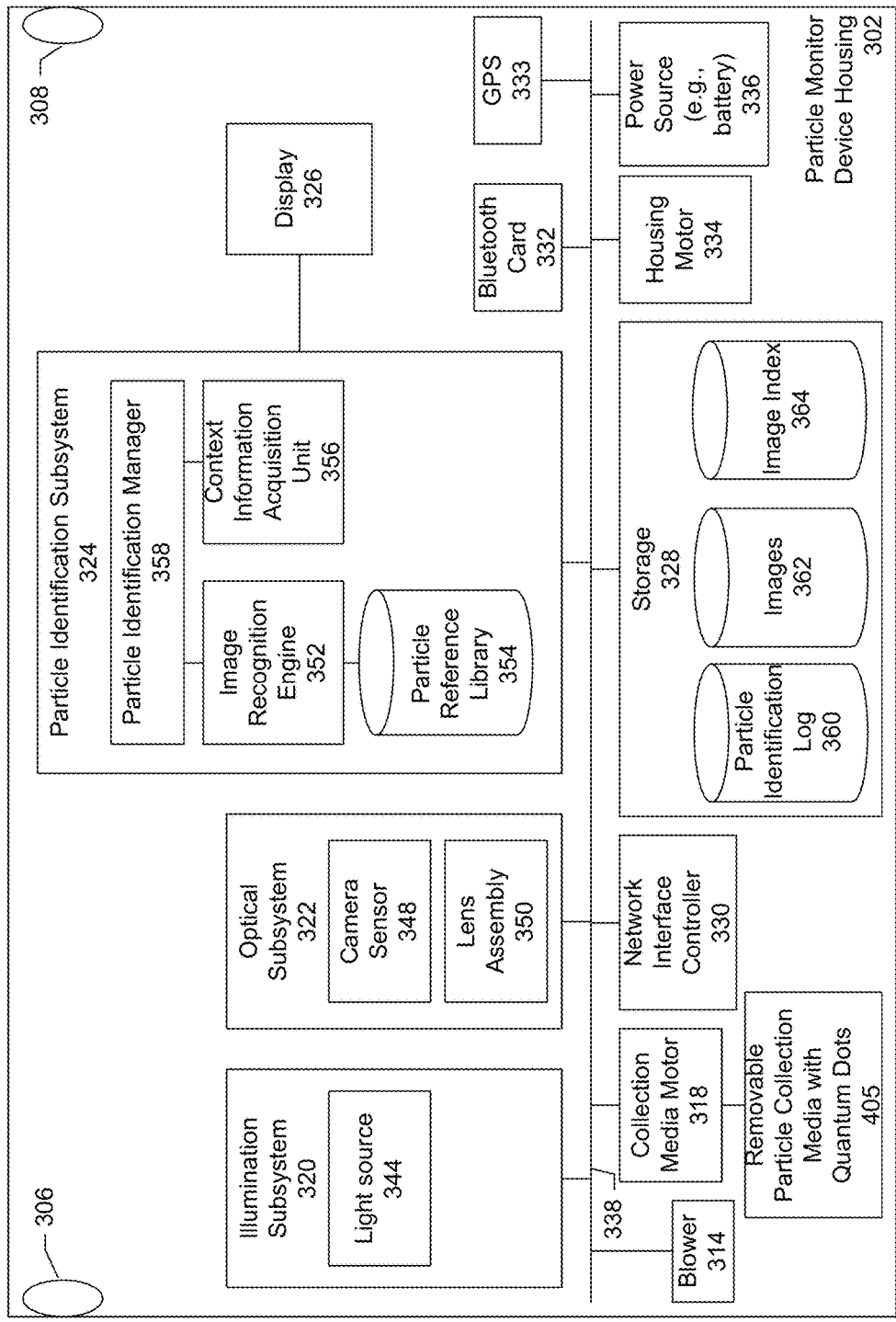
FIG. 4 shows a block diagram of an airborne particle monitor according to another embodiment.

FIG. 4 shows another specific embodiment of particle monitor 105. The particle monitor shown in FIG. 4 is similar to the particle monitor shown in FIG. 3. The particle monitor shown in FIG. 4, however, includes a removable particle collection media with quantum dots 405. In a specific embodiment, the collection media is contained within a cartridge. The cartridge includes a pair of spools and a tape wound about the pair of spools. The tape includes an adhesive and a backing material where the adhesive has been applied to a side of the backing material. Further detail is provided below.

Figure 5:
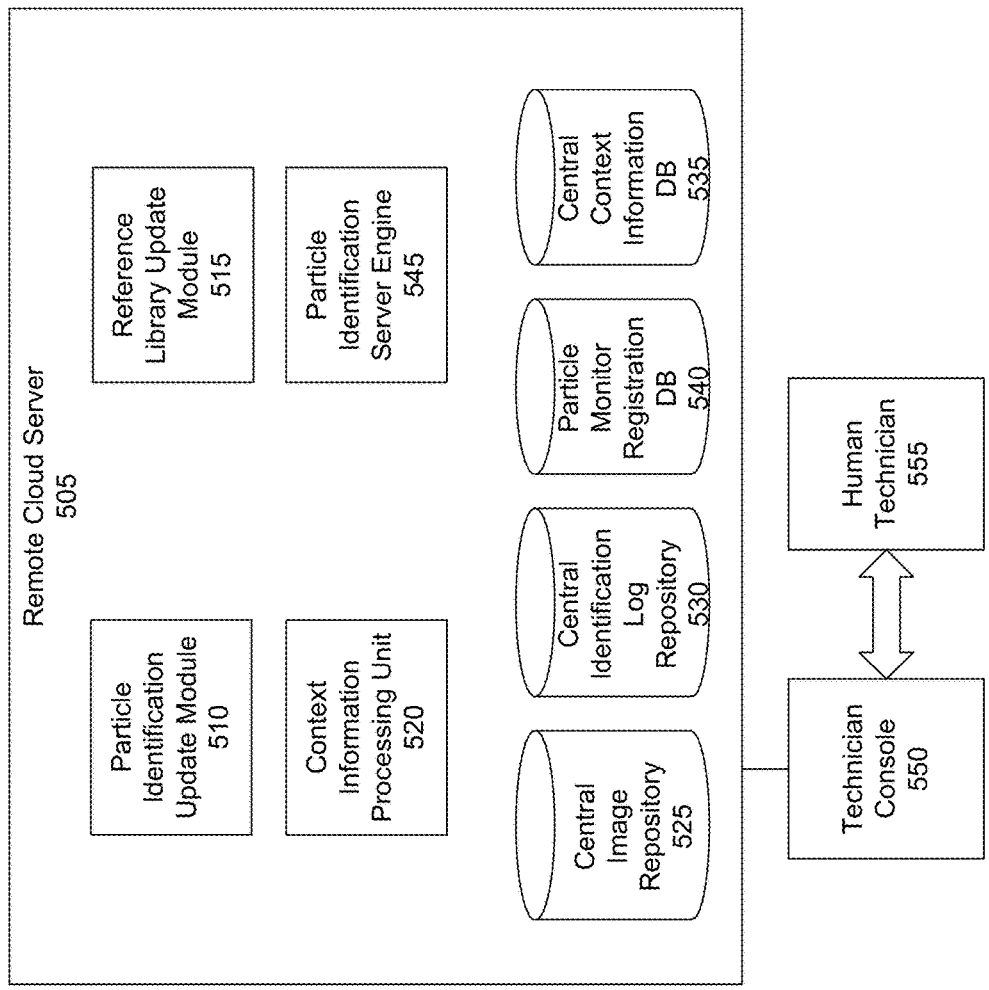
FIG. 5 shows a block diagram of a cloud server according to an embodiment.

FIG. 5 shows a block diagram of a remote cloud server 505 according to a specific embodiment. The server includes a particle identification update module 510, reference library update module 515, context information processing unit 520, central particle image repository 525, central particle identification log repository 530, context information database 535, database 540 storing information about various registered particle monitors that have been deployed, and particle identification server engine 545. A technician console 550 is connected to the server.

The particle identification update module is responsible for sending code updates to the various particle monitors that have been deployed throughout the world. The code updates may include firmware updates. The updates help to ensure that each monitor is equipped with the most recent versions of the algorithms for particle identifications.

The reference library update module is responsible for sending new or updated reference images of particles. For example, as new reference images of particles are made, these reference images can be distributed to each of the various particle monitors. Alternatively, or in addition, the reference library information includes particle-discrimination algorithm parameters that may be distributed to each of the various particle monitors. Storing particle discrimination algorithm parameters can require less storage space than the reference images.

The context information database stores context information such as climatic conditions associated with different types of pathogenic fungal spores, blooming periods of various plants and flowers, geographic location data for the various plants and flowers, weather conditions, and so forth. The context processing unit can receive from a particle monitor a request for context information where the request specifies a geographical location of the particle monitor, time of particle collection, or both. The context processing unit can access the context information database to retrieve a subset of relevant context information corresponding to the geographical location, time, or both and transmit the subset of relevant context information to the requesting particle monitor.

The central particle image repository stores images of particles that have been taken by the various particle monitors and transmitted to the cloud server. The images can be accessed and viewed via the technician console by a human technician 555. The central image repository (or other central repository) may further store the analysis results from the various particle monitors. This allows the technician to perform manual spot checks of the analysis to help ensure that the particle identifications made by the particle monitors are accurate. The image repository further allows the technician make a manual identification of particles by reviewing images where the local particle monitor is unable to make a satisfactory identification.

The central particle log repository stores particle identification logs generated by the various particle monitors and transmitted to the cloud server. As discussed, the particle identification logs can include listings of particle types that have been identified and associated metadata such as a time and date of particle capture, location of particle capture, and so forth.

The deployed monitors database stores information about the various particle monitors that have been deployed throughout the world. The database may be referred to as a particle monitor registration database. The information may include, for example, a geographical location of a particle monitor, particle identification logs containing information about particles captured by the particle monitor, images or an index to images taken by the particle monitor, user information (e.g., company name, name of primary contact, email address, or mailing address) date particle monitor was purchased, device serial number, firmware version, and other information. Table C below shows an example of information that may be stored in the deployed monitor database.

TABLE C

| Monitor ID | Location | Particle ID Log | Images Captured |
| --- | --- | --- | --- |
| 312945 | 45 Appleseed Drive, Santa Rosa, CA 94555 | 2016-05-12_31245_log.txt | 2016-05-12_31245_image.jpg |
| | | . . . | . . . |
| 987431 | 32 Pear Lane, Philadelphia, PA 19042 | 2016-05-12_987431_log.txt | 2016-05-12_987431_image1.jpg |
| | | . . . | . . . |

A first column of the table lists an identifier that uniquely identifies a particle monitor. A second column of the table lists a location where the particle monitor is located. In this example, the location includes a street address. The location may instead or additionally include longitude and latitude coordinates, or any other value or set of values that identifies a geographic location of the particle monitor. A third column of the table lists particle identification logs received from the particle monitor. A fourth column of the table lists particle images received from the particle monitor.

The particle identification server engine is responsible for performing a server-side analysis of the imaged particles. For example, the cloud server may have access to computing resources not available locally at the particle monitor. The particle monitor is designed to be a relatively compact and inexpensive device. The server, however, may include processors more powerful than those at the particle monitor, be able to execute more complex particle identification algorithms than the particle monitor, and so forth.

In an embodiment, when the particle monitor is unable to identify a captured particle, the particle monitor notifies the server. The server can coordinate with the particle monitor in making an identification. For example, the server may use a different set of algorithms to analyze the particle images transmitted from the particle monitor to the server. Based on the analysis, the server may issue instructions to the particle monitor for additional images or other data. The instructions may include a request to capture additional images of the particles. The request may include a specification of the conditions or parameters under which the particles should be imaged. For example, the request may specify a focal depth at which an image should be taken, illumination under which the image should be taken, and so forth.

It should be appreciated that the cloud server is merely representative of an embodiment. There can be multiple cloud server and storage systems. Context information or portions of context information may be provided by one or more third parties. For example, weather conditions may be obtained from a third party that offers weather provider services (e.g., AccuWeather).

Figure 6:
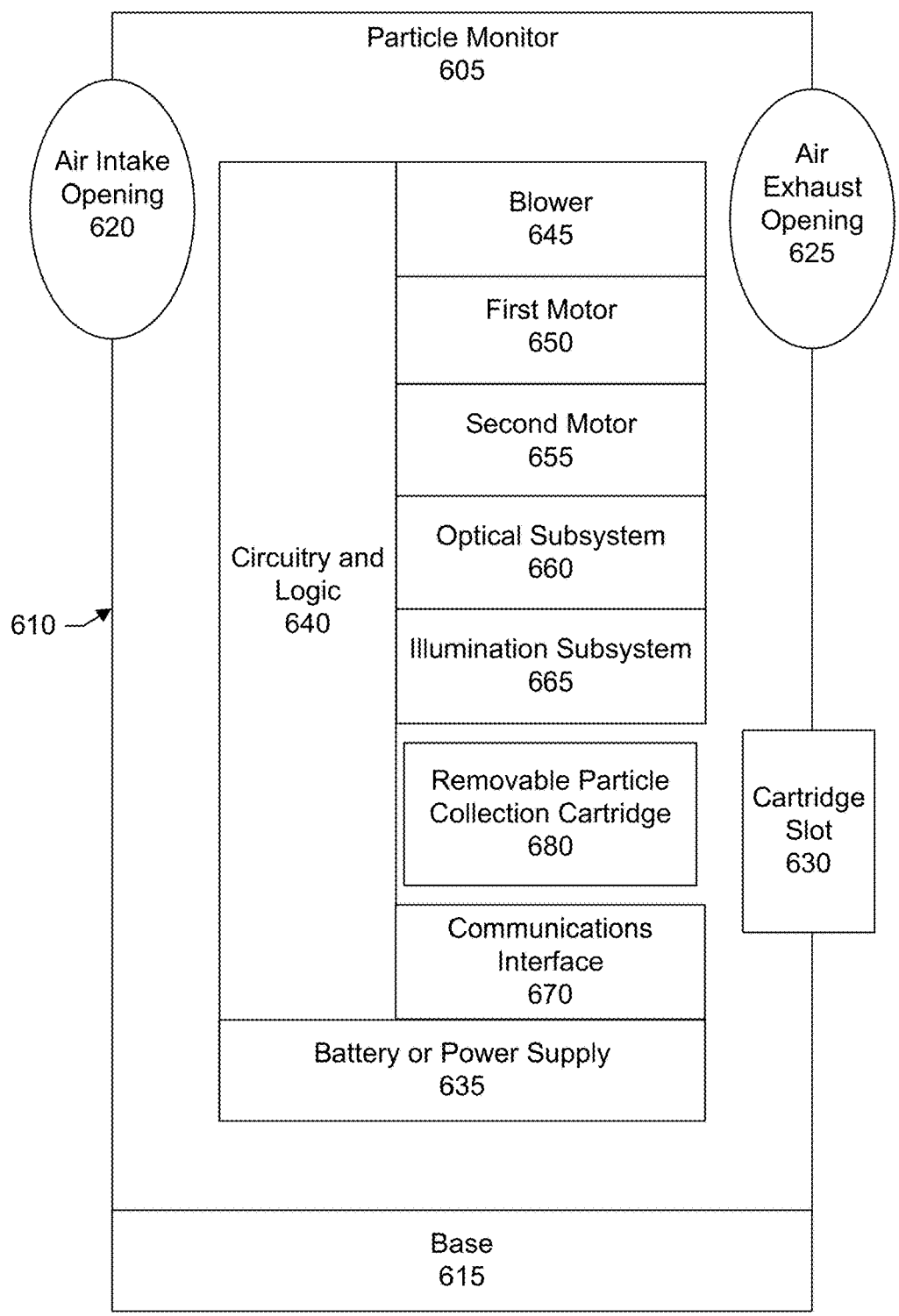
FIG. 6 shows a block diagram of an airborne particle monitor according to another embodiment.

FIG. 6 shows another block diagram of particle monitor 105 according to one embodiment. In the example shown in FIG. 6, a particle monitor 605 includes a housing 610 mounted to a base 615. The housing includes an air intake opening 620, an air exhaust opening 625, and a cartridge slot opening 630. There can be a door connected to the cartridge slot opening via a hinge. The door can open into the cartridge slot. Shown inside the housing are a battery or power supply 635 which is connected to circuitry and logic 640 which in turn is connected to a blower 645, first motor 650, second motor 655, optical subsystem 660, illumination subsystem 665, and communications interface 670.

Further shown in FIG. 6 is a removable particle collection cartridge 680. The particle collection cartridge includes a reel of tape media. The tape media is wound about the reel and includes an adhesive to collect airborne particles (e.g., pollen or mold spores). The collection cartridge is removable from the collection device. That is, a user can remove the cartridge from the collection device without breaking or destroying the device. There can be an eject button that the user can press to eject the cartridge from the particle collection device. For example, when the collection cartridge is full (or as desired), the user can remove the collection cartridge from the collection device through the cartridge slot opening. The user can then install a new collection cartridge by inserting the new collection cartridge into the collection device through the cartridge slot opening. The user can then mail the removed collection cartridge—which contains the collected airborne particles—to a laboratory for a further in-depth analysis.

The design of the particle monitor and cartridge allows for a very flexible approach for collecting and analyzing particles. In particular, in another specific embodiment, the cartridge is used for surface particle sampling. Surface particle sampling may be instead of or in addition to airborne pollen or particle sampling. The cartridge facilitates a collection system or mechanism that is handheld and easily portable. A user can hold a body of the cartridge in their hand, position an opening or slot of the cartridge through which a portion of the tape is exposed, and press the slot against a surface of an object. Particles on the surface may then be transferred from the surface of the object to the exposed portion of the tape. The user can then insert the cartridge into the particle monitor for analysis of the particles that have been collected on the tape.

In a specific embodiment, a handheld portable particle monitor with removable collection cartridge is provided. In this specific embodiment, the monitor is a relatively small, lightweight, inexpensive, and compact device. The monitor is powered by a battery. This allows the monitor to be easily portable and mobile because the monitor does not have to be connected to an electrical outlet to operate. A user can take the monitor and cartridge to an environment where there might not be any electrical outlets such as to a vineyard, farm, plantation, ranch, forest, or other field environment to collect and analyze airborne particles, surface-borne particles, or both.

Particles that may be associated with diseases including agricultural diseases, plant diseases, animal diseases, and so forth can be easily collected, analyzed, and identified in the field before widespread damage occurs. The handheld particle monitor may include a handle connected to a body of the monitor so that the monitor can be carried. Instead or additionally, at a least a portion of an outside surface of the monitor body may be textured or knurled to facilitate carrying. Further, because the monitor may be used in outdoor environments, as well as indoor environments, the monitor may include seals to provide a weather-resistance or weather-proof construction. Examples of seals include O-rings, gaskets, all-weather glue, and others.

The particle collection device may include an electronic screen to display a status associated with operations of the particle collection device (e.g., "collection cartridge tape 80 percent full," "analyzing particles," "device error," "transmitting data to remote cloud server," "firmware update in progress, please wait," and so forth). There can be status lights such as LED status indicators. The particle collection device may include an input device such as a keypad through which the user can power the device on or off, configure various settings and parameters such as collection frequency (e.g., sample air every 5 minutes, every 10 minutes, every 20 minutes, or every 30 minutes), other settings, and so forth. Instead or additionally, at least some settings may be configured remotely such as via a mobile device having a mobile application paired with the particle monitor.

The blower may include a fan and is responsible for creating a vacuum in which air is sucked into the collection device through the air intake opening. A flow path of air is directed to the particle collection cartridge. Particles that may be floating or suspended in the air are trapped by the adhesive tape of the particle collection cartridge. The air then exits the collection device through the air exhaust opening.

The first motor operates to rotate the housing of the collection device about the base. The collection device may include an airflow sensor or airflow direction sensing unit that detects a direction of the flow of the ambient air. Based on the direction of the airflow, the first motor can rotate the collection device to orient or align the air intake opening with a direction of the flow of the ambient air. Instead or additionally, the first motor may be configured to continuously or periodically rotate to obtain good representative samples of the ambient air.

The second motor engages the reel of the tape media to unwind the adhesive coated tape media. For example, as airborne particles such as pollen become trapped in a portion of the adhesive coated tape, the second motor can unwind the reel to expose a new portion of the adhesive coated tape upon which new airborne particles can be collected.

The second motor is further responsible for advancing the tape containing the trapped particles to the optical and illumination subsystems. One or more lighting sources of the illumination subsystem illuminate the trapped particles while a camera sensor of the optical system captures images (e.g., pictures) of the trapped particles for analysis and identification.

The communications interface is responsible for communications with, for example, the mobile device, remote cloud server, or both. The communications interface may include an antenna for wireless communication.

Figure 7:
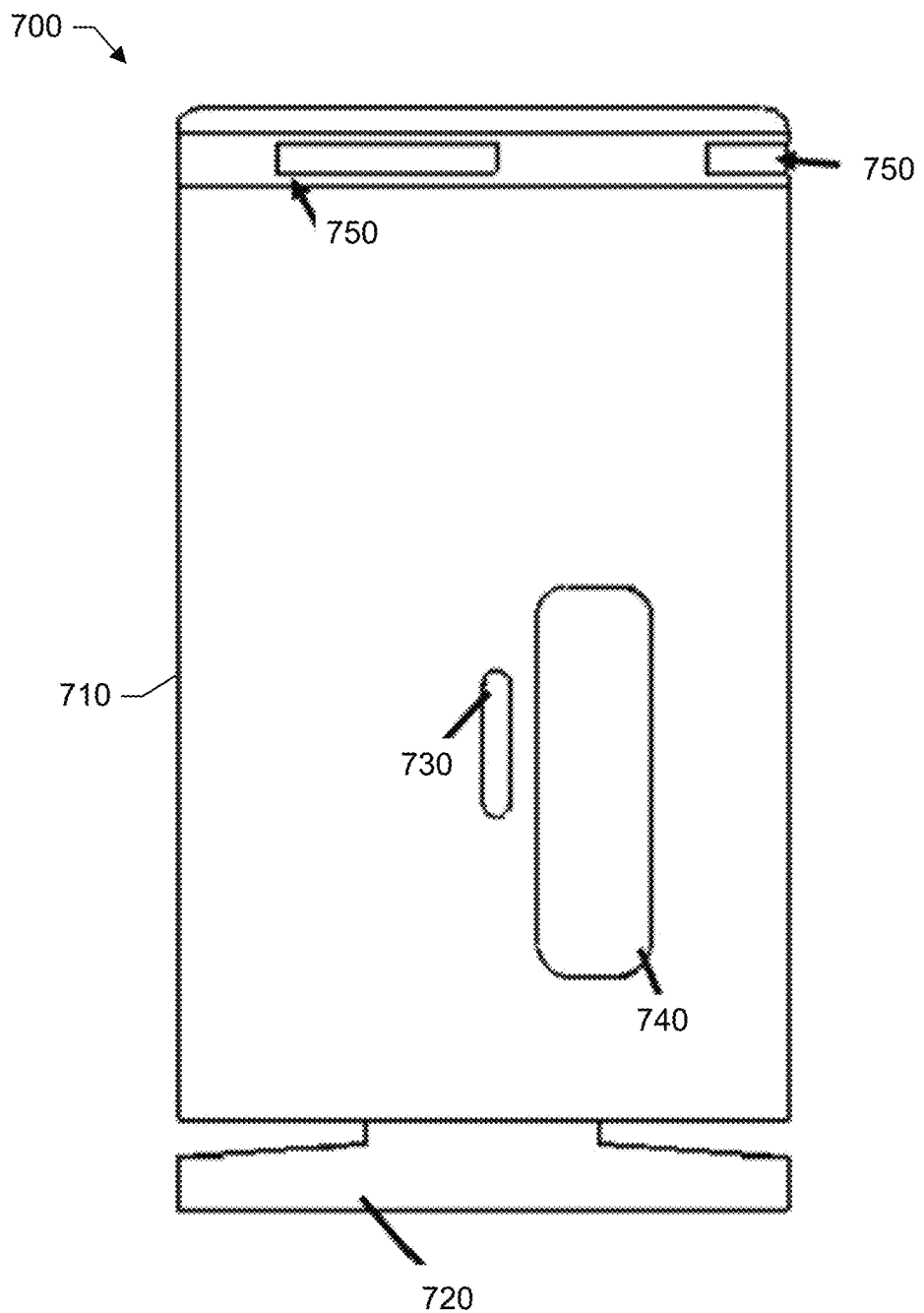
FIG. 7 shows an exterior view of an airborne particle monitor according to a specific embodiment.

FIGS. 7-18 show various views of particle monitor device 105 (and particle collection cartridge) according to an embodiment. FIGS. 7 through 18 illustrate in more mechanical design detail a specific embodiment of an airborne particle monitoring device. FIG. 7 shows an exterior view of a particle monitoring device 700 including a cylindrical housing 710 that contains most of the device components as well as a base 720. Cylindrical housing 710 contains an air-intake slot 730 that may be a few centimeters in length and a width that varies from about 3 millimeters (mm) to about 1 mm in funnel-like fashion as it penetrates the thickness of the cylindrical housing 710. The length of the air-intake slot may range from about 3 centimeters (cm) to about 10 centimeters. This includes, for example, 4, 5, 6, 7, 8, 9, or more than 10 centimeters. The length may be less than 3 centimeters.

Figure 8:
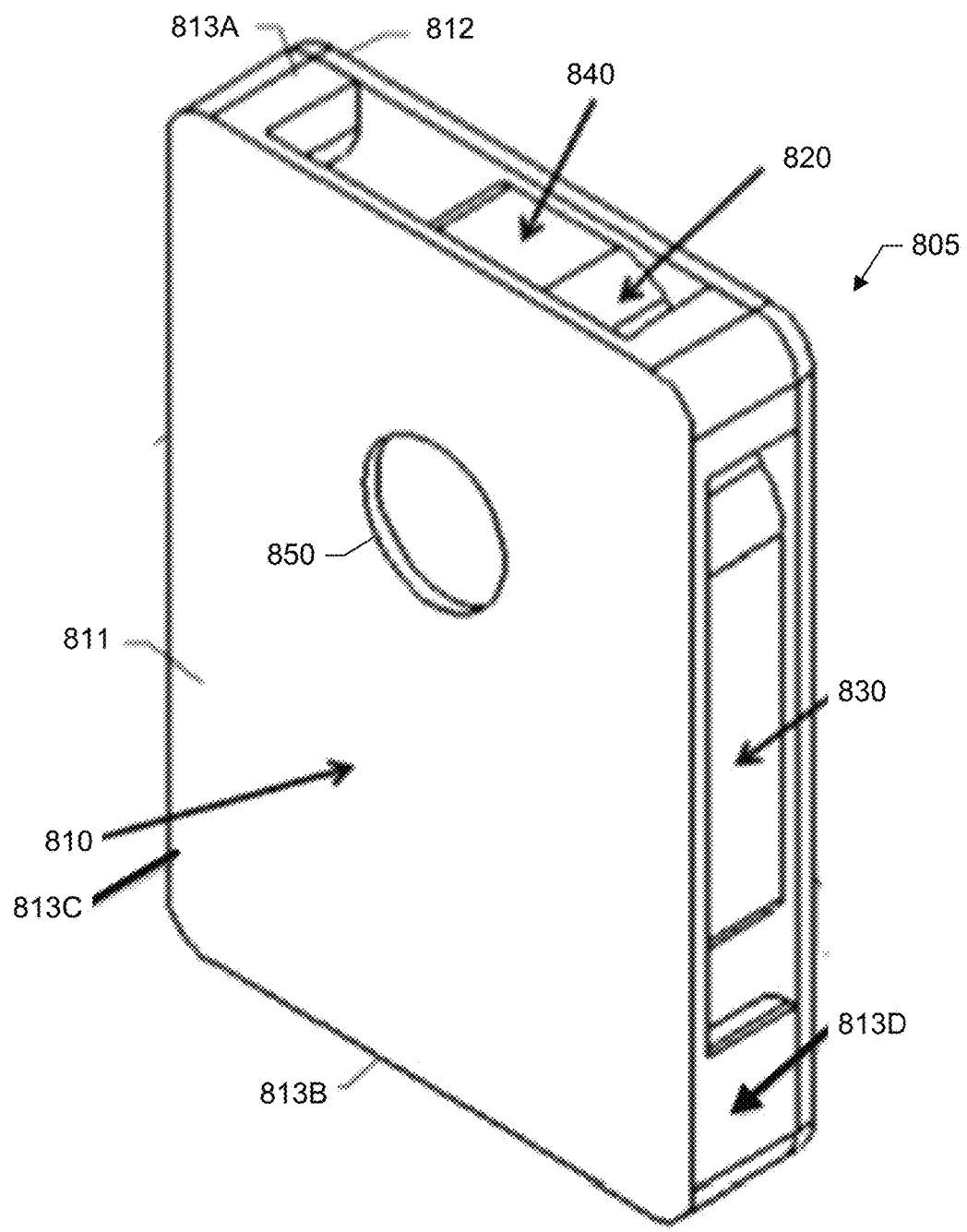
FIG. 8 shows an isometric view of a particle media cartridge that may be used with the particle monitor shown in FIG. 7.

The cylindrical housing 710 also contains a particle-media-cartridge door 740 that may be opened in order to insert or remove particle media cartridges such as shown in FIG. 8 and discussed below. The air-intake slot is adjacent or next to the cartridge door. A shape of the cartridge door includes a rectangle, perhaps with rounded corners. The cartridge door is oriented vertically with respect to a central axis passing through the particle collection device. The door may be positioned closer to the base of the monitor than the top of the monitor.

As shown in the example of FIG. 7, in an embodiment, the cartridge door includes a top door edge, a bottom door edge, opposite the top door edge, and left and right door edges extending between the top and bottom door edges. The bottom door edge is closer to the base than the top door edge and the bottom and top door edges are parallel to each other. The left and right door edges are opposite and parallel to each other.

The air-intake slot includes a top intake edge, a bottom intake edge, opposite the top intake edge, and left and right intake edges extending between the top and bottom intake edges. The bottom intake edge is closer to the base than the top intake edge and the bottom and top intake edges are parallel to each other. The left and right intake edges are opposite and parallel to each other.

In an embodiment, the air-intake slot is located relatively close to the cartridge door. This helps to allow particles in the air entering through the air-intake slot to be collected on the media cartridge. For example, an arc length as measured clockwise (when viewed from above in plan-view) along the outside surface or circumference of the cylindrical housing from the left door edge to the right intake edge may be A1 (if viewed from below, it would have been counter-clockwise). An arc length as measured clockwise along the outside surface or circumference of the cylindrical housing from the right intake edge to the left door edge may be A2. Arc A1 may be less than arc A2. A ratio of A1 to A2 may be about 1:80. The ratio, however, may vary greatly and in other embodiments may be about 1:40, 1:45, 1:50, 1:55, 1:60, 1:65, 1:70, 1:75, 1:85, 1:90, 1:95, 1:100, 1:105, 1:110, 1:115, or 1:120. In an embodiment, the air-intake slot is between a first line or arc about the housing extending from the top door edge and a second line or arc extending from the bottom door edge, the first and second lines being parallel to each other. The air-intake slot may be shaped as a rectangle, oval, obround, circle, or any other shape as desired. There can be multiple air-intake slots (e.g., two, three, four, five, or more than five air-intake slots).

The cylindrical housing 710 and its contents may rotate about its cylindrical axis with respect to the base in order to orient the air-intake slot 730 in a desired direction. In some cases, it may be desired to systematically vary the orientation of the air-intake slot 730 in order to average over all directions. Alternatively, the particle collection device 700 may orient itself so that the air-intake slot 730 faces upwind to any breeze or other flow of ambient air. In this latter case, it is advantageous for the particle collection device 700 to include wind or airflow sensors. Visible in FIG. 7 are two of four wind-detector recesses 750 in which may be mounted airflow sensors in such a way that they are both exposed to ambient airflow and mechanically protected from accidental impact or contact. In a specific embodiment, a wind-detector recess includes a cantilever deflection detector. Wind detectors of many types, including hot-wire airflow detectors, cantilever deflection detectors, or both may be placed in the wind-detector recesses 750.

The generally cylindrical elongated shape of the housing helps to reduce interference with other external objects (e.g., grape-vine branches) when the collection device rotates to sample airborne particles such as pollen, mold spores, or both from different directions. In this specific embodiment, a cross-sectional shape of the housing includes a circle. In other specific embodiments, a cross-sectional shape of the housing may include a square, rectangle, oval, triangle, or any other shape.

Figure 9:
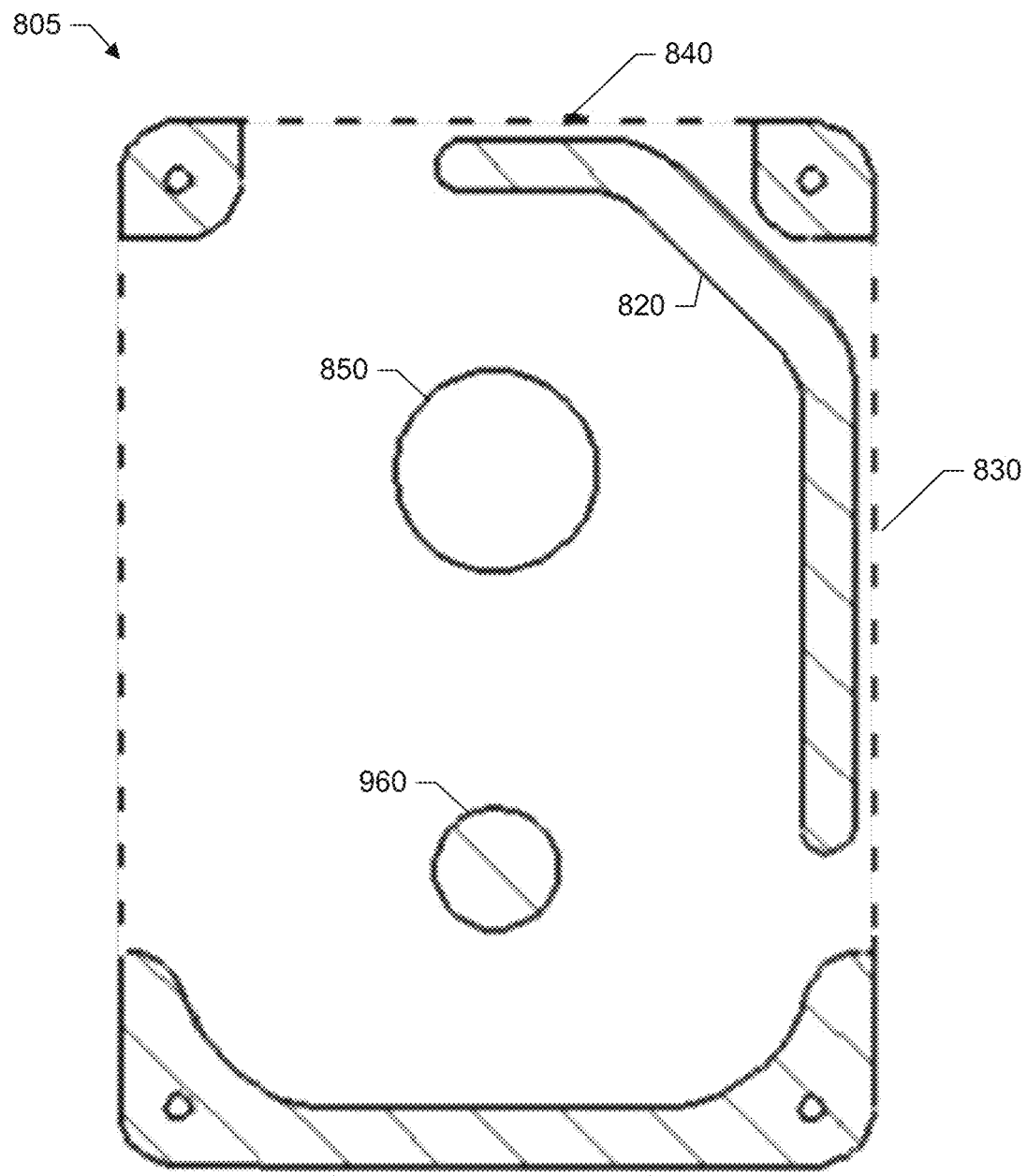
FIG. 9 shows a plan view of a cross section of the cartridge shown in FIG. 8.
Figure 10:
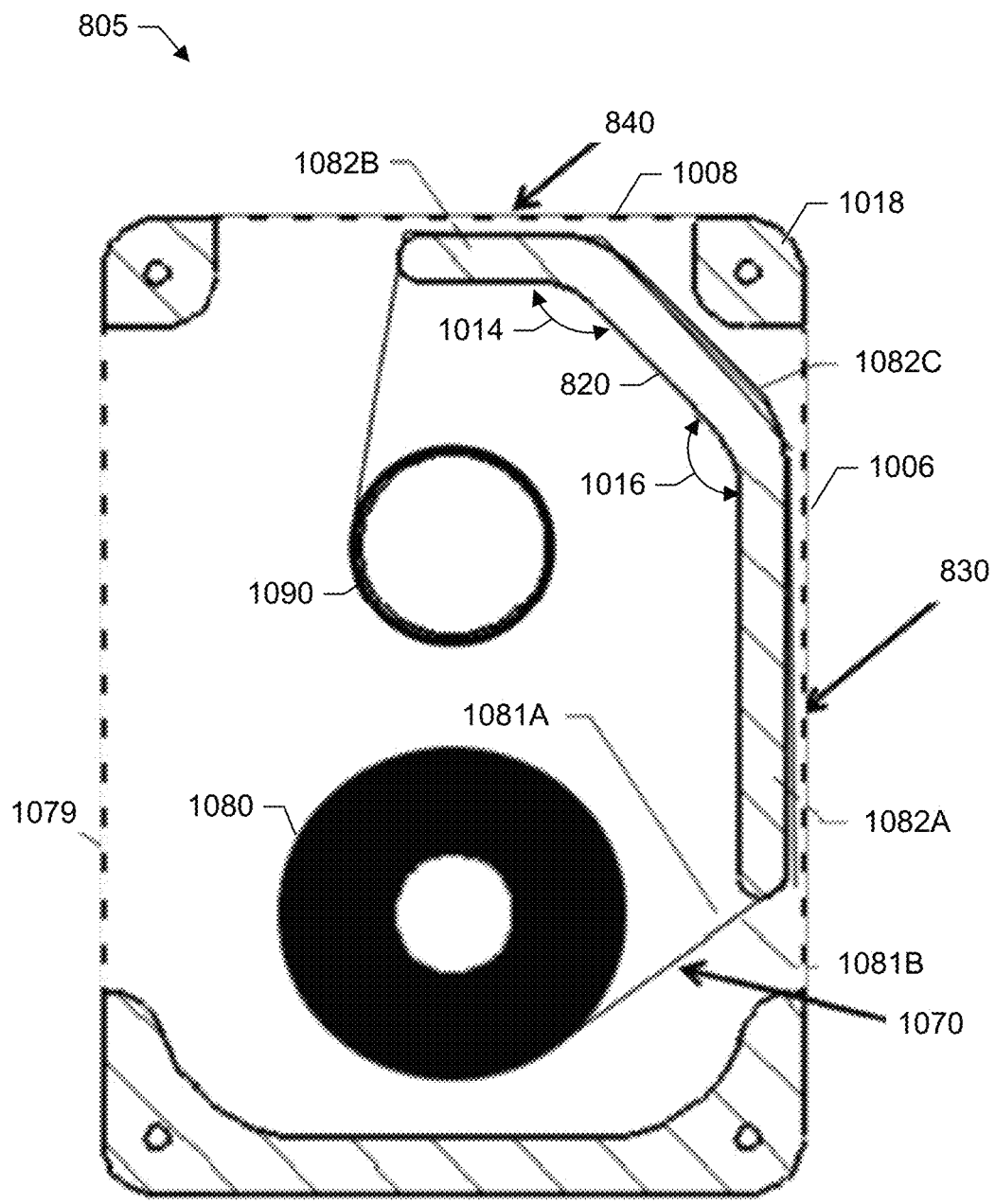
FIG. 10 shows a plan view of a cross section of the particle media cartridge including media of the cartridge shown in FIG. 8.

FIGS. 8-10 illustrate a particle media cartridge 805 that may be loaded or removed from the particle collection device 700 via the particle-media-cartridge door 740. The cartridge includes a media for capturing particles as well as a cartridge body 810. In this specific embodiment the media includes an adhesive coated tape, however, in other embodiments a different media may be used such as adhesive coated slides. The cartridge body 810 includes a tape guide structure or wall 820 that includes portions including an air-intake zone 830 and a particle inspection zone 840. The cartridge body 810 includes a gear-shaft hole 850 that will be discussed further below. In alternate embodiments, particularly in cases where it is desired to be able to rewind as well as advance the tape, there may be a second gear-shaft hole (not shown).

FIGS. 9 and 10 show a cross-section of the cartridge body with the media (FIG. 10) and without the media (FIG. 9). The cross-section is for a plane parallel to, in the middle of, planes corresponding to front panel 811 (FIG. 8) and back panel 812 (FIG. 8). The dashed lines in FIGS. 9 and 10 represent portions of the plan-view edges of front panel 811 and back panel 812 shown in FIG. 8.

Referring now to FIG. 10, a supply reel 1080 of adhesive coated tape 1070 is mounted to supply-reel post 960 (FIG. 9). In the air-intake zone 830, the tape guide structure 820 fixes the location of the adhesive coated tape 1070 where it collects particles in the face of air pressure from air entering the cylindrical housing 710 (FIG. 7) via the air-intake slot 730 (FIG. 7). The adhesive coated tape 1070 then passes the particle inspection zone 840 and is finally collected at the uptake reel 1090. Optionally, after use within the particle collection device 700, the particle-media cartridge may be removed from device 700 and sent to a laboratory where particles captured by media can be further studied optically or with bio-assays. Such a particle-media cartridge physically containing captured airborne particles is one embodiment of physical archive 260 of FIG. 2.

Referring now to FIG. 8, in a specific embodiment, a user-removable or replaceable particle media cartridge is provided. The cartridge includes a front panel 811, a back panel 812, opposite the front panel. Side panels including a top side panel 813A, a bottom side panel 813B, a left side panel 813C, and a right side panel 813D extend between the front and back panels. The top and bottom side panels are opposite to each other. The left and right side panels are opposite to each other. The top and bottom side panels are orthogonal to the right and left side panels. As shown for left, top and right sides, side "panels" may cover only a small portion of their respective side. The cartridge has a shape of a rectangle.

Referring now to FIG. 10, the right side panel includes a first opening or slot that may be referred to as air intake zone 830. The top side panel includes a second opening or slot that may be referred to as particle inspection zone 840. The left side panel includes a third opening or slot that may be referred to as an exhaust port 1079. A length of the cartridge between the top and bottom side panels is L1, a width of the cartridge between the left and right side panels is W1, a length of the air intake zone opening is L2, a length of the particle inspection zone opening is L3, and a length of the exhaust opening is L4. In an embodiment, a ratio of L2 to L1 may be about 1:1.5, but may vary greatly such as 1:1.3, 1:1.4, 1:1.6, or 1:1.7. A ratio of L3 to W1 may be about 1:1.4, but may vary greatly such as 1:1.2, 1:1.3, 1:1.5, or 1:1.6. A ratio of L4 to L1 may be about 1:1.5, but may vary greatly such as 1:1.3, 1:1.4, 1:1.6, or 1:1.7.

A thickness of the cartridge between the front and back panels is T1. A width of the air intake zone opening is W2. A width of the particle inspection zone opening is W3. A width of the exhaust opening is W4. In an embodiment, the width of the openings W2, W3, and W4 are equal. In another embodiment, a width may be different from another width. In an embodiment, a ratio of at least one of W2, W3, or W4 to T1 is about 1:1.4, but may vary greatly such as 1:1.2, 1:1.3, 1:1.5, or 1:1.6. A shape of the intake zone, particle inspection zone, and exhaust openings may be a rectangle or other shape (e.g., oval, round, obround, or circle).

Inside the cartridge is supply reel 1080, uptake reel 1090, and tape guide structure 820. The supply reel includes the roll of tape. The tape includes an inside or bottom surface 1081A and an outside or top surface 1081B, opposite the inside surface. The tape is wound so that the inside surface faces towards a center of the roll, and the outside surface faces away from the center of the roll. The outside surface of the tape includes an adhesive. The tape may be made of a thin flexible material such as narrow strip of plastic. In an embodiment, the tape is non-magnetic or not magnetic or does not include a magnetizable coating. The tape includes an adhesive coating on the outside surface of the tape to trap particles. In some embodiments, tape may be clear, translucent, transparent, or at least partially transparent to facilitate illumination of trapped particles. That is, the tape may be made of a material that allows at least some light to pass through.

The inside surface of the tape may not include the adhesive and preferably moves with minimal or low friction against tape guide 820. The inside surface may be treated with a coating that allows the inside surface of the tape to glide freely across the tape guide. For example, in an embodiment there is a roll of tape including an inside surface and an outside surface. A coating or treatment is applied to the inside surface such that a coefficient of friction of the inside surface after the treatment is less than a coefficient of friction of the inside surface before the treatment. In another specific embodiment, the tape or portions of the tape may include a magnetizable coating. Such a magnetizable coating may be used to mark and read locations along the length of the tape of interesting particles that may merit later laboratory testing such as bio-assays.

The tape guide structure is sandwiched between the first and second panels of the cartridge. The tape guide includes a first segment 1082A, a second segment 1082B, orthogonal to the first segment, and a third segment 1082C extending between ends of the first and second segment. The first segment extends in a direction parallel to the right side panel. The first segment extends along at least a portion of the length of the front and back panels. The first segment includes a surface that faces the first opening (e.g., air intake zone) of the cartridge.

The second segment extends in a direction parallel to the top side surface. The second segment extends along at least a portion of the width of the front and back panels. The second segment includes a surface that faces the second opening (e.g., particle inspection zone). A length of the first segment may be greater than a length of the second segment. A length of the first segment may be less than a length of the second segment. A length of the first segment may be the same as a length of the second segment.

The tape extends from the supply reel, across the top surfaces of the first, second, and third segments of the tape guide structure, and terminates at the uptake reel. The uptake reel is closer to the top side of the cartridge than the supply reel. The supply reel is closer to the bottom side of the cartridge than the uptake reel. The tape is configured so that the inside surface contacts the top surfaces of the first, second, and third segments of the tape guide structure while the outside surface of the tape, which includes the adhesive, is exposed at the air intake and particle inspection zones. Thus, particles entering the air intake zone can be trapped by the adhesive and then inspected at the particle inspection zone. The air can pass from the air intake zone and out the exhaust port of the cartridge. The inside surface of the tape may be smooth or without the adhesive so that the tape can glide across the tape guide structure.

The first segment of the guide is positioned so that it is slightly recessed within the opening of air intake zone 830. That is, right side edges 1006 of the front and back panels of the cartridge extend slightly past the first segment. A distance from the right side edges of the panels to the first segment may be at least a thickness of the tape. The recessing of the first segment helps to protect the tape from unintended contact with other objects.

Similarly, the second segment of the guide is positioned so that it is slightly recessed within the opening of particle inspection zone 840. That is, top side edges 1008 of the front and back panels of the cartridge extend slightly past the second segment. A distance from the top side edges of the panels to the second segment may be at least a thickness of the tape. The recessing of the second segment helps to protect the tape from unintended contact with other objects.

In the example of the cartridge shown in FIG. 10, the first and second segments of the tape guide are on adjacent sides of the cartridge. That is the first segment is on the right side of the cartridge and the second segment is on the top side of the cartridge. The position of the tape guide segments corresponds to the design of the particle monitor. For example, when the cartridge is inserted into the particle monitor, the second segment of the tape guide will be located directly below the optical subsystem or microscope including camera sensor and lens assembly. It should be appreciated, however, that the tape guide segments may be positioned at other locations depending upon the design of the particle monitor.

An angle 1014 is between the second and third segments. An angle 1016 is between the first and third segments. In an embodiment, the angles are obtuse, i.e., the angles are more than 90 degrees but less than 180 degrees. The angles and positioning of the tape guide segments help to prevent creases in the tape as the tape transitions from the supply reel, to the intake zone, below and past an upper right corner 1018 of the cartridge, to the inspection zone, and to the uptake reel. The ends and corners of the tape guide may be rounded as shown in the figure to help ensure that the tape glides smoothly over the tape guide and does not snag.

The cartridge, including the tape guide structure, may be made of plastic, nylon, metal, or other material, or combination of materials. The tape guide structure may be formed or molded as a single unit with one of the front or back panels of the cartridge. Alternatively, the tape guide structure may be formed as a unit separate from the front and back panels. When the tape guide structure is formed as a separate unit, the tape guide structure may be attached to at least one of the front or back panels using any number of a variety of techniques. Such techniques may include snap-fits, fasteners (e.g., screws), glues, and others.

Likewise, the front and back panels may be fastened together using any number of a variety of techniques. For example, the front and back panels may be snap-fitted together. The front and back panels may be glued together. In an embodiment, the front and back panels are connected using screws. In this embodiment, each corner of one of the front or back panel may include a screw boss. The boss provides a mounting structure to receive a screw. The screw passes through a hole in a corner of one of the front or back panels and is received by a screw boss located in a corresponding corner of another of the front or back panels.

Figure 11:
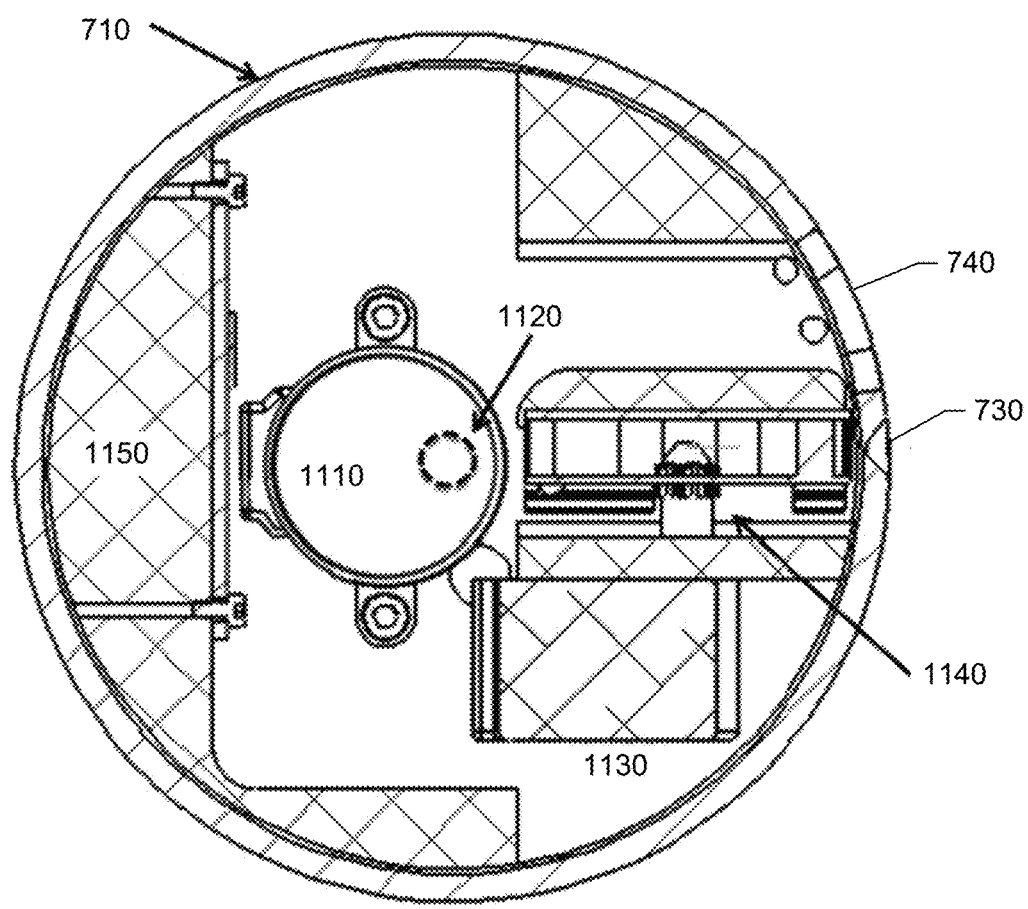
FIG. 11 shows a plan-view of the particle monitor shown in FIG. 7 including motors.

FIG. 11 shows a plan-view of selected items of the particle collection device 700 shown in FIG. 7. The device includes two electric motors. Orientation motor 1110 rotates the cylindrical housing 710 and its contents about its vertical axis and relative to the base 720 (FIG. 7). While the orientation motor 1110 is not centered with respect to the axis of the cylindrical housing 710, the orientation motor's gear shaft 1120 is centered. The intake-reel gear shaft 1140 of the cartridge-reel motor 1130 extends horizontally and controls the rotation of the uptake-reel 1090 (FIG. 10) of the cartridge. The gear shaft hole 850 (FIG. 9) allows the intake-reel gear shaft 1140 to enter the particle-media cartridge body 810 (FIG. 8). Many of the contents contained within the cylindrical housing 710, including motors 1110 and 1130, are mechanically supported by the internal mounting structure 1150. For example, internal components of the monitoring device such a printed circuit board, motors, and so forth may be attached to the internal mounting structure using various fasteners, welding, adhesives, or combinations of these. Examples of fasteners include nuts, bolts, screws, and washers. Adhesives include epoxy or glue. Examples of welding include plastic welding. The internal mounting structure 1150 may be formed of a sculpted volume of plastic. The mounting structure may be formed using injection molding.

Figure 12:
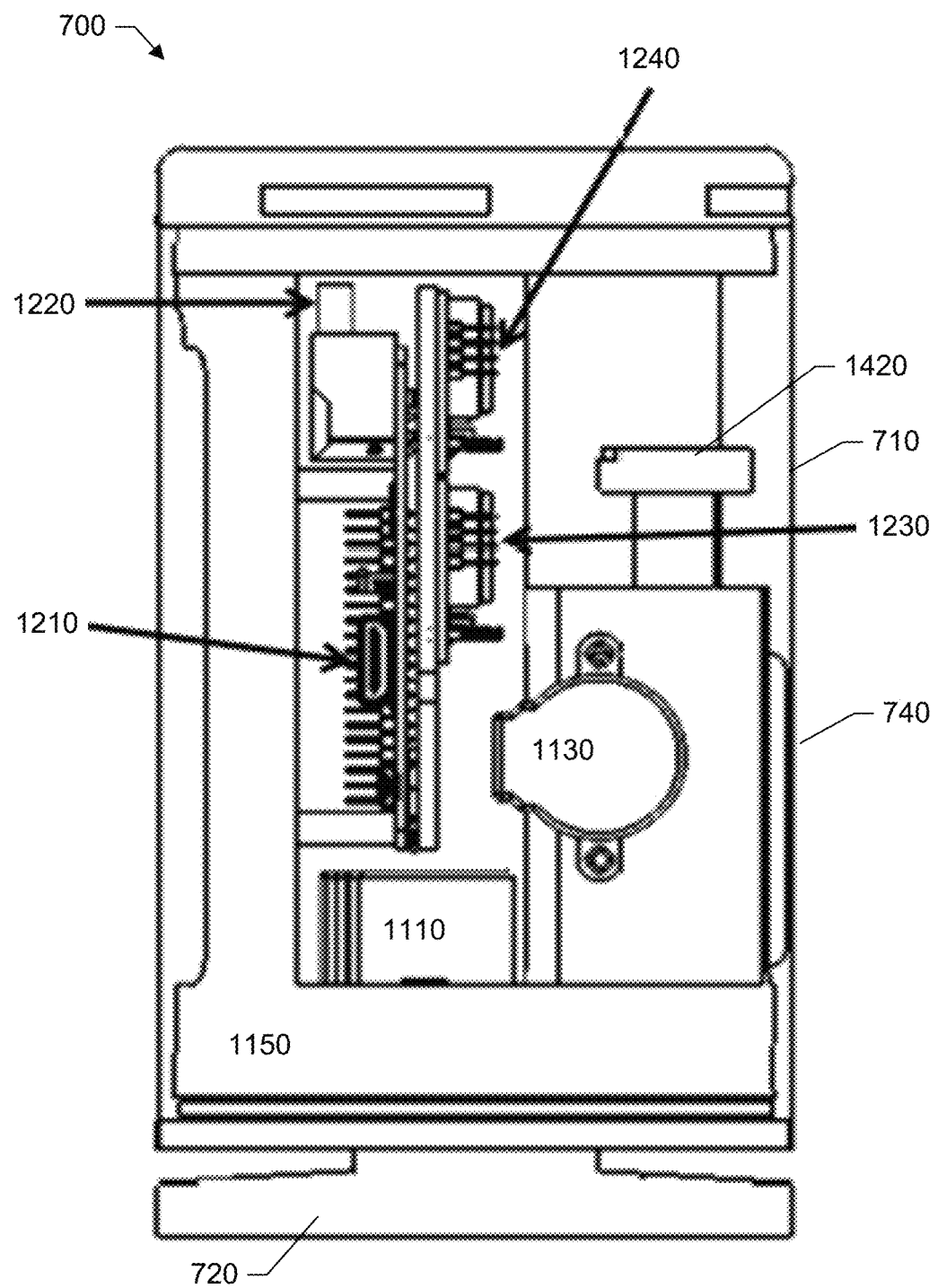
FIG. 12 shows a vertical cross-section of the particle monitor shown in FIG. 7 illustrating the placement of electronic boards.

FIG. 12 shows a vertical cross section of particle monitor device 105 according to a specific embodiment. In this specific embodiment, the particle collection device includes three electronic boards. There is a motherboard 1210, an orientation-motor circuit board 1230, and a cartridge reel motor circuit board 1240.

Motherboard 1210 contains many electronic components including a microprocessor (e.g., Raspberry Pi) and a wifi antenna 1220. Alternatively Bluetooth or any other wireless protocol may instead or additionally be used. For effective wireless communication, it is preferable that cylindrical housing 710 be constructed from a non-conductive material such as plastic rather than a metal.

Additional circuit boards (not shown) may be included. Also not shown in FIG. 12 for purposes of clarity are numerous wires interconnecting various components such as wires between the motors and their corresponding circuit boards. Motherboard 1210 may contain the hardware of local processor 240 of FIG. 2.

The motors are located closer to a bottom of the particle monitor than a top of the particle monitor. In an embodiment, orientation motor 1110 is located near the bottom so as to be close to base 720. Cartridge reel motor 1130 also is located nearer to the bottom than the top of the particle monitor as the particle-media cartridge is placed below the optical system. While the motors may be light weight, in the case that the motors are relatively heavy, locating the motors towards the bottom of the particle monitor helps to lower the center of gravity and provide stability so that the monitor is unlikely to tip over. Likewise, a power supply such as a battery may be located closer to the bottom of the monitor than the top of the monitor.

In an embodiment, the motors are light weight. For example, a motor may weigh about 113-142 grams (or 4-5 ounces) only. In this embodiment, one benefit of placing the motors on the bottom is because the base of the system may be on a surface and when coupled with a ball bearing it enables for easy rotation. The battery is likely to add more weight near the bottom which would be advantageous.

Specifically, with respect to a vertical positioning, the orientation motor is between the bottom of the monitor and the motherboard. The cartridge reel motor is between the orientation motor and the camera sensor. The camera sensor, being relatively light, is positioned closer to the top of the monitor than the bottom of the monitor. The camera sensor is between the cartridge reel motor and the top of the particle monitor. With respect to a horizontal positioning, the cartridge reel motor is between the motherboard and the cartridge door.

Figure 13:
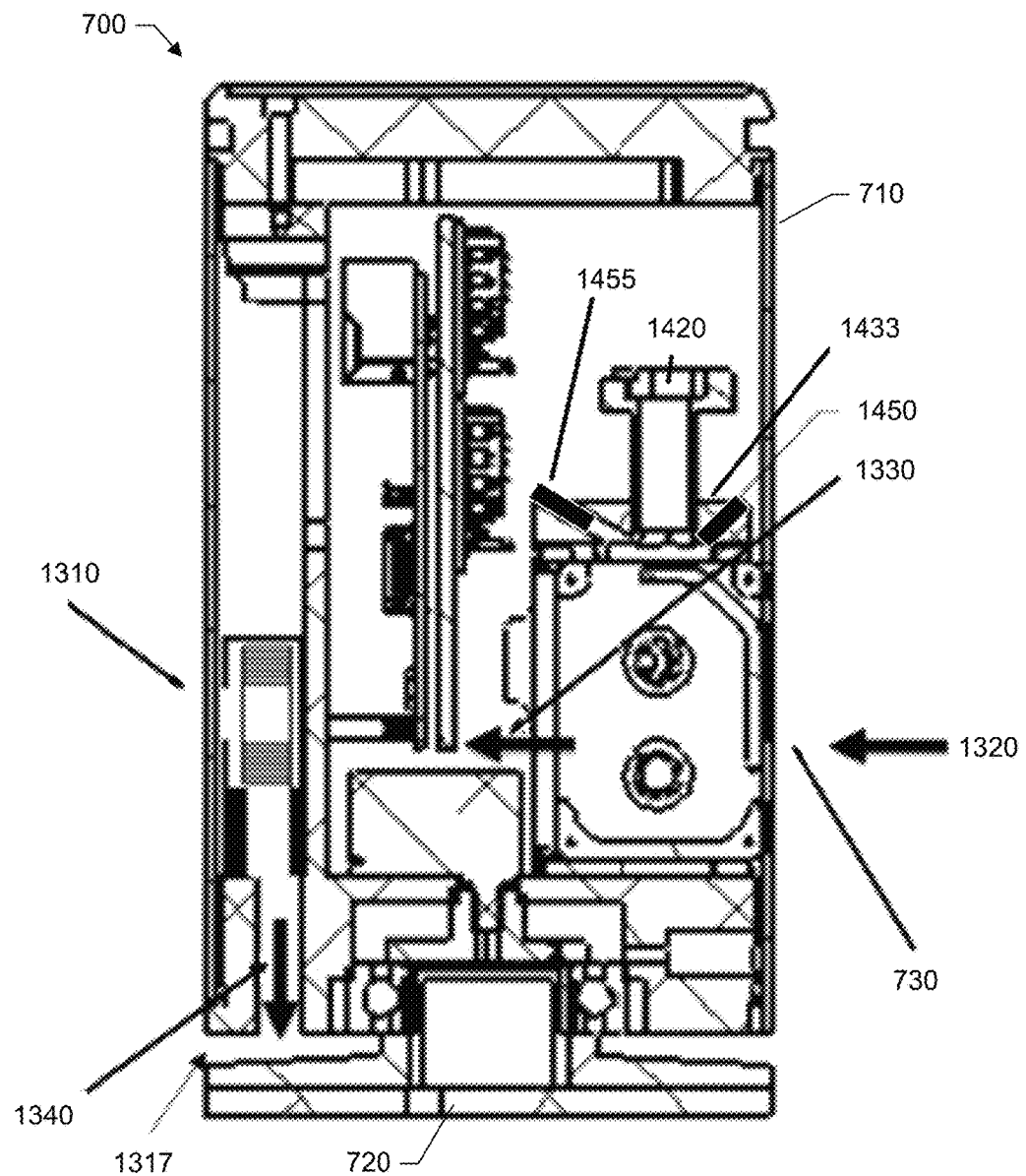
FIG. 13 shows some detail of the particle monitor shown in FIG. 7 with optics and particle media cartridge, as well as illustration of air flow.

FIG. 13 illustrates how sampled ambient air flows through the monitor device 700. Sampled ambient air 1320 enters through the air-intake slot 730 and immediately encounters the air-intake zone 830 (FIG. 10) of the particle-media cartridge. Here the adhesive-coated tape 1070 (FIG. 10) captures many of the particles within the sampled ambient air 1320. Device-interior air 1330 then exits out the backside of the particle-media cartridge body 810 (FIG. 8); for this purpose and as seen in FIG. 10, the back side of the cartridge is open rather than closed. Finally exhaust air 1340 (FIG. 13) leaves the device. This airflow is driven by blower 1310 which pushes out exhaust air 1340 and sucks in sampled ambient air 1320. The blower is opposite the air intake slot and above the exhaust. A gap 1317 between a bottom of the housing and a top of the base allows the exhaust air to escape. The mechanisms for ambient air sampling illustrated in FIG. 13 represents one embodiment of air intake hardware 220 of FIG. 2.

Air intake slot 730 is opposite the blower and is configured to direct a flow path of ambient air created by the blower towards or over the first opening of the cartridge or air intake zone. For example, there can be channel, duct, conduit, tube, or passageway that directs the flow path of the air from the air intake zone. Particles, such as mold spores, pollen, or both, in the air are trapped by the adhesive on the tape. Preferably, the airflow in the air intake zone is turbulent in order to maximize or increase the chances that particles in the sampled air will be separated from the air and adhered to the capturing medium. When desired, cartridge reel motor 1130 (FIG. 11) advances the tape containing the trapped particles to the second opening of the cartridge or inspection zone. The camera sensor can then capture images of the particles trapped within the adhesive tape.

Figure 14A:
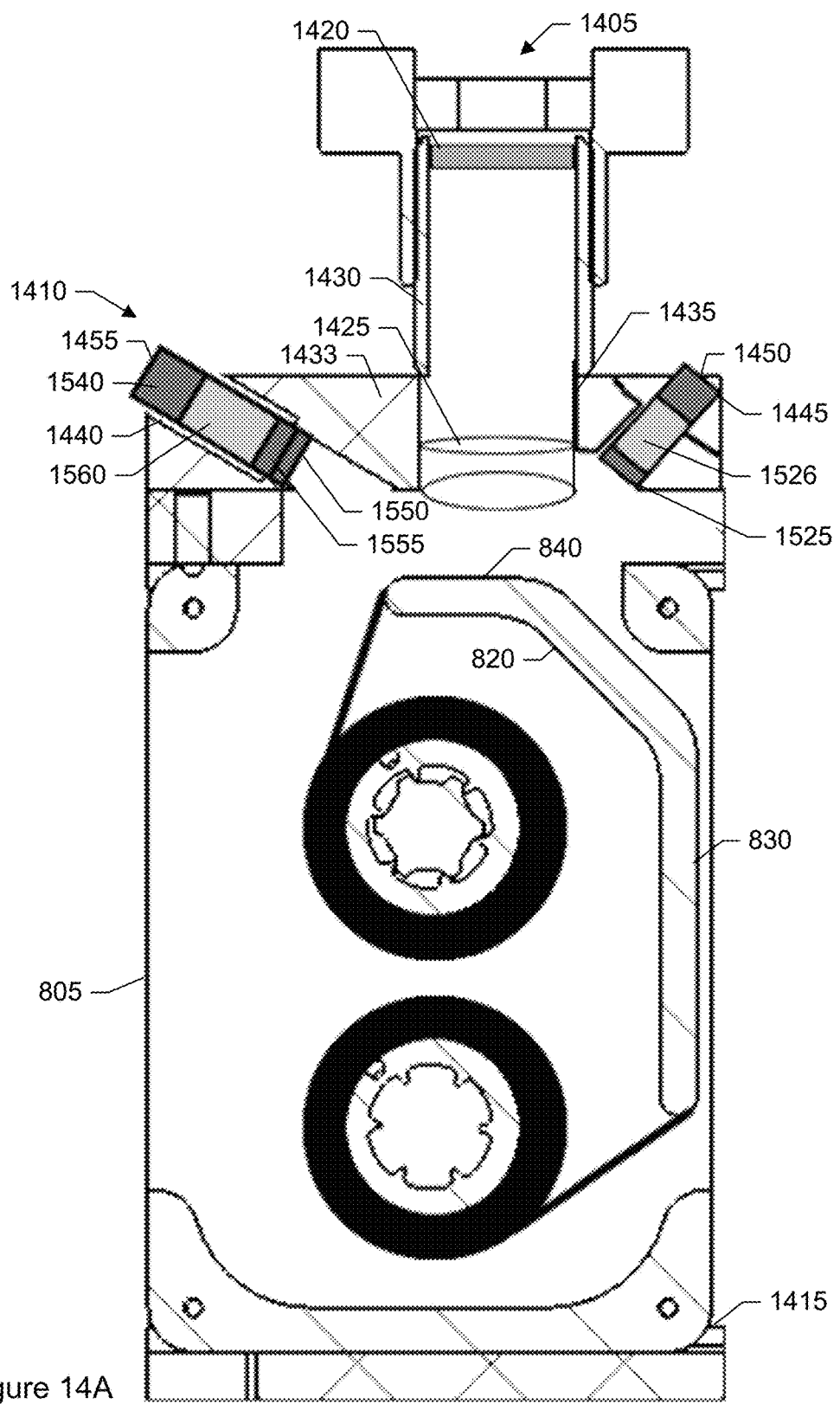
FIG. 14A shows a side view of an inside portion of the particle monitor shown in FIG. 7.
Figure 15:
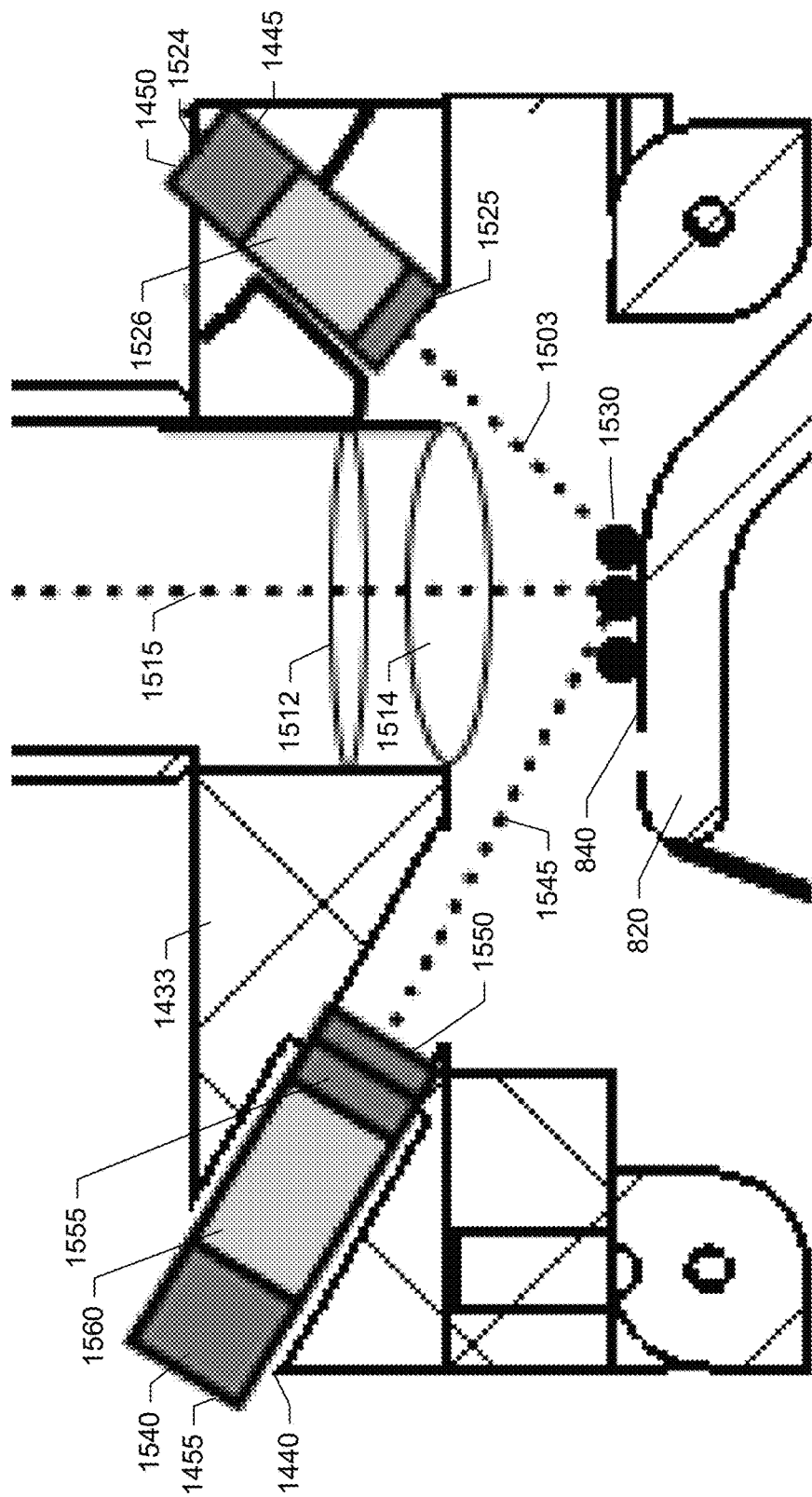
FIG. 15 shows an enlarged side-view cross-section of the particle monitor shown in FIG. 7 showing further details of the optical and illumination system according to a specific embodiment.

FIG. 14A shows a side view of an inside portion of monitor device 700. The monitor device includes an optical subsystem 1405, illumination subsystem 1410, cartridge well 1415, platform 1433, and particle-media cartridge 805. FIG. 14A illustrates a loaded particle-media cartridge in the cartridge well along with an optical subsystem for particle inspection. FIG. 15 provides more detail on the optical and illumination subsystems. During a collection period, particles entering the monitor are trapped within air intake zone 830 by the adhesive of the tape. The tape or, more specifically, a portion of the tape having the trapped particles, is then advanced to particle inspection zone 840 for inspection. The duration of the collection period can be configured by a user or administrative user. For example, the collection period may be configured to be 5, 10, 15, 20, 30, 60, 90, 120, or more than 120 seconds (e.g., 3, 4, 5, 6, 7, 8, 9, 10, 15, 30, 45, or more than 45 minutes; 1, 2, 3, 4, 5, or more than 5 hours). The collection period may be less than 5 seconds.

The optical subsystem includes a camera sensor 1420, lens assembly 1425, and tube 1430. The lens assembly is positioned at a bottom end of the tube and the camera sensor is positioned at a top end of the tube, opposite the bottom end of the tube. The cartridge well receives and holds the particle-media cartridge in a vertical position.

Contributing to the cost-effectiveness of particle-monitoring device 700 is the use of a camera sensor 1420 contained within a mass-produced and highly-integrated camera sensor chip package such as the SONY IMX line of camera sensors and the Omnivision OV line of camera sensors as provided by Sony Corporation of Tokyo, Japan and OmniVision Technologies Inc. of Santa Clara, Calif., respectively. Such highly integrated packages avoid the cost and mechanical bulk of many associated electronic circuits.

Figure 14B:
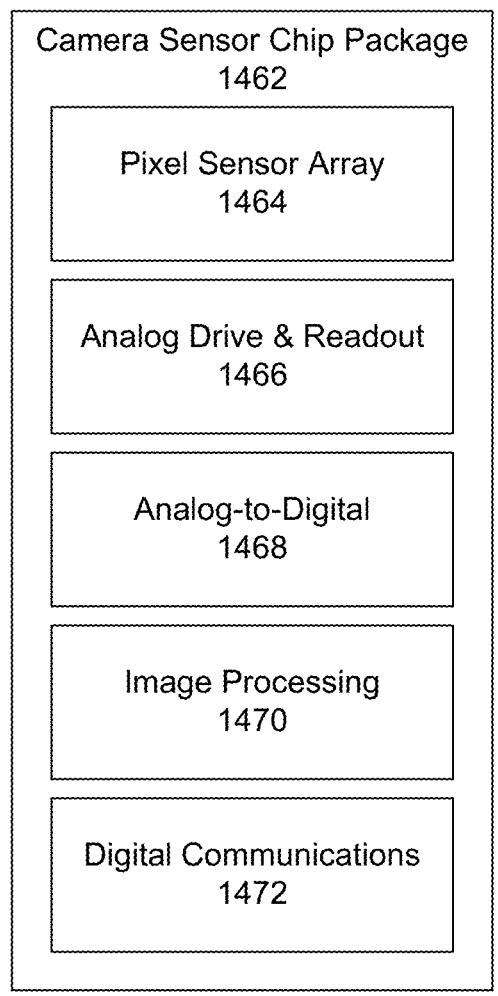
FIG. 14B shows a block diagram of a highly integrated camera sensor chip package.

As illustrated by the block diagram of FIG. 14B, a highly integrated camera sensor package 1462 includes within a single chip package not only the light-sensing pixel sensor array 1464, but also analog drive and readout circuitry 1466, analog-to-digital conversion circuitry 1468, digital image processing circuitry 1470, digital communications circuitry 1472 to transfer digital images to a host processor, as well as many other circuits not shown in FIG. 14B such as power regulation circuitry, timing circuits, and so forth. With all these supporting circuits contained with the highly integrated camera sensor package 1462, the number of electronic components in the bill of materials for a particle-monitoring device 700 is significantly reduced, thus reducing cost and enabling a more compact mechanical design.

Platform 1433 is positioned above the cartridge well. The platform can be between the cartridge well and illumination and optical subsystems. The platform includes a first hole 1435, a second hole 1445, and a third hole 1440. The bottom end of the tube of the optical subsystem extends into the first hole which opens to face particle inspection zone 840 of the particle media-cartridge. In other words, when the particle media-cartridge is inserted into the particle monitor, the particle inspection zone of the cartridge aligns with the first hole. The camera sensor is directly above the lens assembly which is directly above the particle inspection zone. The arrangement allows the camera sensor to capture images of particles that have been trapped by the adhesive coated tape.

In other words, in the example shown in FIG. 14A, the platform is above the cartridge well that receives the collection cartridge. The camera sensor is positioned within the particle monitor device to be above or over the second opening or particle inspection zone of the cartridge. The camera sensor is closer to a top of the particle monitor than the cartridge.

Positioning the camera sensor above the particle inspection zone helps to reduce the probability of particles falling onto the camera lens and obscuring the images. For example, in some cases, particles remaining in the sampled air and not adhering to the tape may settle on the lens, the bond between the adhesive coated tape and collected airborne particles may be weak, the adhesive coated tape may include a large collection or mound of particles and particles at the top of the mound may not be secured to the adhesive coated tape, and so forth. The collection cartridge and camera sensor may be aligned such that a line passing through the supply and uptake reels passes through or near the particle inspection zone and lens to the camera sensor. In another embodiment, the tape is transparent and the image capture is from the backside of the tape (the non-adhesive side). This prevents particles from entering the lens as well since they hit the tape surface and the camera optics and imaging system is located behind the tape surface.

In a specific embodiment, the cartridge well is rotatable about a vertical axis parallel to the central axis passing longitudinally through the housing. For example, at least one of the top, bottom, or side of the cartridge well may be connected to a pin (e.g., rod, spindle, shaft, or axle). The pin may sit or revolve within a hole, bushing, or ball bearing connected to the housing. In this specific embodiment, when the media cartridge is loaded through the cartridge door and into the monitor, the cartridge well can pivot so that the air-intake slot of the housing aligns with or faces the air intake zone of the cartridge. This helps to facilitate airflow towards the air intake zone of the cartridge.

In an embodiment, the cartridge well pivots through a distance at least a thickness of the cartridge. The cartridge well may pivot through any number of degrees (e.g., 1, 2, 3, 4, 5, 10, 15, 20, 30, 60, 90, 120, or 180 degrees). The ability of the cartridge well to pivot allows the air-intake slot to be located anywhere on the housing. For example, the air-intake slot may be located on an opposite side of the cartridge door. In other words, a distance between the air-intake slot and the cartridge door may be equal to a diameter of the housing or half the circumference of the housing.

Rotating the cartridge away from the cartridge door helps to ensure that ambient or outside light that may enter or leak through the cartridge door and into the interior space of the monitor does not enter the particle inspection zone when the trapped particles are being illuminated by the illumination subsystem. Reducing or minimizing the amount of ambient or outside light entering the particle inspection zone helps to ensure accurate measurements.

In a specific embodiment, the illumination and optical subsystems remain stationary or are fixed-in-place while the cartridge well pivots. This helps to ensure consistent measurements. In another specific embodiment, one or more of the illumination or optical subsystems may pivot with or with respect to the cartridge well.

The cartridge well may pivot through any number of positions. For example, there can be a first position in which the cartridge well faces the cartridge door so that the cartridge can be loaded into the well. The cartridge well may then pivot from the first position to a second position where the air intake zone of the cartridge faces the air intake slot of the housing. The cartridge well may remain in the second position while the collected particles are illuminated and particle images captured. The cartridge well can then pivot from the second position back to the first position so that the cartridge can be removed and another cartridge inserted.

In another specific embodiment, there can be a first position in which the cartridge well faces the cartridge door so that the cartridge can be loaded into the well. The cartridge well may then pivot from the first position to a second position where the air intake zone of the cartridge faces the air intake slot of the housing. Once a collection period has ended, the cartridge well may pivot from the second position to a third position, away from the air intake slot, where the collected particles are illuminated and particle images captured. The cartridge well can then pivot from the third position back to the second position for another particle collection session, or pivot back to the first position so that the cartridge can be removed and another cartridge inserted.

In other embodiments, the cartridge well may be designed to translate. For example, in another specific embodiment, a particle monitor may include a tray that slides out of the particle monitor. The tray receives the cartridge and slides back into the particle monitor. In the example shown in FIG. 7, the cartridge door is shown as being on a side of the particle monitor between the top and bottom of the monitor. The side entry helps to facilitate a short overall height and small diameter of the monitor.

In other embodiments, however, the cartridge door may be located on the bottom of the monitor and the cartridge may be inserted through the bottom of the monitor. Locating the cartridge door on the bottom helps to reduce the probability of unwanted water (e.g., rain) or other debris entering into the monitor. The cartridge door may be located on the top of the monitor and the cartridge may be inserted through the top of the monitor. Locating the cartridge door at the top can allow a cartridge to be loaded and removed without having to pick-up the monitor.

As shown in FIG. 14A, the optical subsystem is slightly offset towards a right side of the platform. The optical subsystem is closer to the right side of the platform than a left side of the platform, opposite the right side. The optical subsystem may be closer to a side of the cylindrical housing than a central axis passing longitudinally through the cylindrical housing. This offsetting or arrangement of the optical system helps to facilitate the compact design of the particle monitor device as other internal components may be located to the left of the optical tube. Also, to better approximate real-time monitoring, such an offset also has the benefit of reducing the distance between the particle capture at air intake zone 830 and particle inspection zone 840. In another specific embodiment, the optical axis may be symmetric with respect to the light sources.

The second hole 1445 houses a first illumination or light source 1450. Light from a first light emitting element 1524 (FIG. 15) is directed within a guide 1526 to a diffuser 1525. The third hole 1440 houses a second illumination or light source 1455. The illumination sources illuminate the particle inspection zone so that the camera sensor can capture images of the trapped particles when illuminated by the illumination sources.

For example, FIG. 15 shows an enlarged view of a portion of the section view shown in FIG. 14A. Particles 1530 collected on the tape have been moved to particle inspection zone 840. First light source 1450 illuminates 1503 the particle inspection zone with first light. Camera sensor 1420 (FIG. 14A) captures images of particles in particle inspection zone 840 (or a scene) within a field view of the camera sensor to generate a first image. That is, the first image is generated while the particles are illuminated with the first light. Second light source 1455 illuminates the particle inspection zone with second light, different from the first light. The camera sensor captures particles in the particle inspection zone within the field view of the camera sensor to generate a second image. That is, the second image is generated while the particles are illuminated with the second light. The first light source may be deactivated when capturing the second image.

In an embodiment, it is desirable that the area around the particle inspection zone be dark. This helps to provide a controlled lighting environment for illuminating the particles under different specified lighting conditions and image capture. Thus, components within the area around the particle inspection zone may be black, colored black (e.g., painted black or a dark color), non-reflective, processed so that the resulting surface finish is darker as compared to the surface before the processing, and so forth.

The first and second lights have different spectral characteristics. For example, the first light may include white light (e.g., light having a broad range of wavelengths and is perceived by the human eye as being colorless) and the second light may include light corresponding to an absorption spectrum of a particle of interest, or the second light may provide ultraviolet light illumination capable of exciting fluorescence of biomolecules. In an embodiment, the first and second images are analyzed to identify or discriminate the particles. For example, the first and second images may be compared to each other to detect changes or differences in the appearance of the particles in the images based on the different lighting conditions under which the particles were photographed.

Detecting such changes (or the lack of changes) can provide an indication of what a particle might be (or not be) because different types of particles can have different light absorption characteristics. These differences in light absorption characteristics can be exploited in order to identify or discriminate the particles. Capturing various images of the same particles but under various different lighting conditions can be used to "probe" and identify or discriminate the particles.

As discussed, lens assembly 1425 images the particles within particle inspection zone 840 on camera sensor 1420 (FIG. 14A). The lens assembly may include one or more lenses. FIG. 15 illustrates the case where the lens assembly includes a weak (i.e., longer focal length) lens 1512 in combination with a strong (i.e., shorter focal length) lens 1514. In the example shown in FIG. 15, the strong lens is closer to the particle inspection zone than the weak lens. Optionally, the lens assembly 1425 may provide an electrically controlled focal length, for example, through a combination of a strong lens 1514 of fixed focal length and a weak lens 1512 whose focal length is electrically controlled.

Given a fixed location of camera sensor 1420 and of lens assembly 1425, increasing the net or effective focal length of the lens assembly 1425 moves the object focal plane down and decreasing the focal length moves the object focal plane up. That is by properly adjusting the focal length of the lens array 1425, one can bring into focus particles 1530. Furthermore, for larger particles or for optical arrangements with shallower depths of field, different adjustments of net focal length of the lens assembly 1425 can bring into focus different horizontal layers of a translucent particle like pollen grains. A set of images focused on different horizontal layers may provide information on the three-dimensional structure.

A lens with an electrically controlled focal length is generally more reliable than a moving mechanical mechanism. In other words, the reliability of modern electronic devices depends heavily in replacing moving mechanical mechanisms with electronic mechanisms. From this perspective, it is very attractive to be able to be able to adjust in real-time the focus of the particle monitor's optical system with no or few mechanical movements, but instead control the focal length of the lens assembly purely electronically. Available lenses with electronically controller focusing tend to be weak lenses, too weak for identifying or discriminating particles. A weak lens in combination with a strong lens, however, can provide for reliability identifying or discriminating particles. In other words, this problem can be overcome with a strongly focusing lens assembly comprising a fixed strong lens and a weak electronically controlled lens.

In any case, an optical axis 1515 of the lens array intersects the particle inspection zone 840 where particles 1530 such as mold spores, pollen grains, or both may be located. Such a lens assembly may be part of image capture hardware 226 of FIG. 2.

The camera sensor 1420 (FIG. 14A) may be a black-and-white camera sensor, but in order to generate richer spectral information it is preferable that the camera sensor 1420 be color sensitive such as providing the ability to capture RGB (red-green-blue) color images. Indeed, the large volume or scale at which color camera sensors are manufactured as compared to black-and-white camera sensors have resulted in color camera sensors being less expensive than black-and-white camera sensors.

Both black-and-white cameras and color cameras provide information on the shape and structure of imaged objects, in other words the "morphology" of imaged objects. Color cameras also provide color information. The particle monitor can analyze an image to distinguish between types of particles through morphological features (e.g., is it round or rod like?, is it smooth or spikey?, is it large or small?, and so forth).

In another specific embodiment, the camera sensor 1420 may be a light-field camera sensor. These items represent embodiments of the image capture hardware 226 of FIG. 2.

Referring back now to FIG. 15, third hole 1440 within platform 1433 houses second illumination source 1455. The second illumination source may include, as shown in FIG. 15, a second light emitting element 1540, a quantum-dot film 1555, an optional diffuser 1550, and an optical shaft 1560. Second hole 1445 within the platform houses first illumination source 1450. A diffuser can be optional as the quantum-dots themselves will randomize the directions of emitted light. Alternatively, quantum-dot film 1555 may be absent and second light emitting element 1540 may directly illuminate the particle inspection zone 840.

Second light emitting element 1540 provides light reaching the particle inspection zone 840 via light propagation approximately parallel to an illumination axis 1545. The illumination light may be visible light, UV light, or infrared light, or a combination thereof. As discussed, different types of particles can have different light absorption characteristics. For morphology analysis, visible light, or even one color of visible light can be sufficient. It is also an option to perform morphology analysis based on UV fluorescence images. In other words, UV fluorescence images may be used for morphology analysis. Thus, a UV light source may be used to identify a shape and outline of the particle and to also probe its fluorescent properties or characteristics. As a result, in an embodiment a visible or white light source may be omitted from a particle monitor.

In some cases, a morphology analysis will not be sufficient to make a conclusive identification as there can be particles of different types but which have the same or similar geometric features. Color information becomes particularly interesting when it provides even a crude level of biochemical analysis without the delays and cost of wet-laboratory techniques. The differences in light absorption characteristics of different particles can be exploited to identify particles or discriminate between particles.

For example, pollen grains tend to have a yellowish color, so color as perceived by the human eye, or an RGB camera sensor under white light illumination is of value to check if a candidate pollen grain is indeed yellowish. Illuminating with white light and capturing the resulting image provides a useful indication of the colors of the particles that have been captured. Grass pollens tend to have bio-molecule chlorophyll-a and hence a pollen grain with visible light absorption peaks of chlorophyll-a is likely to be a grass pollen.

Fluorescence under UV illumination is a marker of bio-molecules that can be used to distinguish between organic and inorganic particles. Biochemical information can be provided by UV fluorescence. Fluorescence is a property some molecules have in which they absorb light of one color and emit light of a different color (e.g., different wavelength). While UV light might not be detected by the camera sensor, the resulting fluoresced or emitted light from the particle may be detected by the camera sensor. As another example, illumination in near infra-red (near enough in wavelength to visible light to be detected by the camera sensor) may provide useful information in regards to identifying particles or discriminating between particles.

Camera sensor 1420 (FIG. 14A) may image scattered light, fluorescent light, or both. Light scattering, where photons bounce off objects in a different direction without changing their wavelength/color is the workhorse of light imaging. With rare exceptions, this is how we see objects in our daily lives when we use our eyes. Just as with our human eyes, in the particle monitor's basic object shape and color information comes from light scattering. UV fluorescence is less common (such as in "black lights") and is of interest in particle identification and discrimination because UV fluorescence indicates the presence of biological materials and may provide information about the types of biological materials.

Optionally, to provide a more uniform illumination of the particle inspection zone 840, a diffuser 1550 may be placed along the illumination axis between second light emitting element 1540 and the particle inspection zone 840. The second light emitting element 1540 and the diffuser 1550 may be mechanically connected with an optical shaft 1560 forming a rigid illumination-source sub-assembly.

Preferably, optical shaft 1560 has optical wave-guiding properties so as to more efficiently direct light from second light emitting element 1540 to particle inspection zone 840. Third hole or illumination channel 1440 may penetrate platform 1433 in order to hold the rigid illumination-source sub-assembly in place and to remove material around the illumination axis 1545.

As shown in the example of FIG. 15, there is a 55-degree angle between the optical axis 1515 and the illumination axis 1545; however other angles are also possible. This includes angles larger than 90-degrees if the adhesive-coated tape and the tape guide 820 under the particle inspection zone 840 are at least partially transparent. Larger than 90-degree illumination angles are also an option for alternate embodiments for which sampled particles are captured on transparent glass or plastic slides instead of with adhesive-coated tape. FIG. 15 illustrates just one possible azimuthal angle for an illumination axis 1545; optionally any azimuthal angle may be used. Such illumination options represent embodiments of illumination hardware 224 of FIG. 2.

Light emitting element 1540 may be an LED (light emitting diode) including possibility an OLED (organic light emitting diode), or a laser, or any other type of light generating device. Furthermore, light emitting element 1540 may be of the downstream end of an optical fiber bringing light from a light emitting element mounted elsewhere. Light emitting element 1540 may provide a wide range of wavelengths, such as with a white-LED, or provide a narrow range of wavelengths, such as with a laser. To provide more information for recognition of particle types, there can be multiple illumination sources.

The holes formed in the platform for light sources, optical shaft, or both may have a cross-sectional shape of a circle. In other embodiments, the cross-sectional shape of a hole may be an oval, square, rectangle, or other shape. In some applications it may be useful to use cross-sectional hole shape as part of a keying system that controls what type of illumination source sub-assemblies are inserted into which holes. A light source may include a light emitting element and optical fiber. The use of optical fiber allows the light emitting element to be located anywhere within the particle monitor and not necessarily within the platform. The ability to locate the light emitting element anywhere within the particle monitor helps to facilitate a compact design.

For example, the light emitting element may be located in the base of the platform. An end of an optical fiber may be connected to the light emitting element. An opposite end of the optical fiber may be connected to a hole or opening in the platform. The optical fiber transmits light from the light emitting element to the platform or particle inspection zone so that the collected particles can be illuminated for the camera sensor. There can be multiple strands of optical fiber. A cross-sectional shape of the optical fiber may be a circle or other shape.

As previously stated, image capture hardware 226 of FIG. 2 may advantageously take advantage of commercially available camera sensors. Due to mass market demand for color digital cameras including cameras built into smart phones, sophisticated RGB (red, green, blue) camera sensors are available at relatively low cost. A feature of the system allows for the use of such relatively low-cost camera sensors for an automated pollen detection systems based on optical imaging of sampled pollen. Spore and pollen color information is of interest for differentiation between types of biological particles. Now let us take a closer look at the spectral characteristics mass produced camera sensors.

Figure 16:
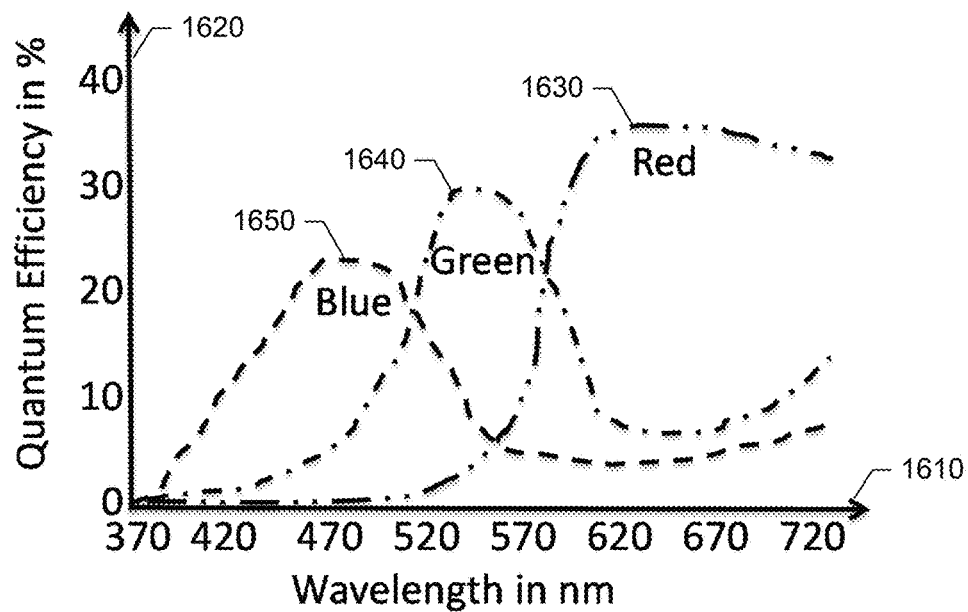
FIG. 16 is a graph showing spectral characteristics typical of an RGB camera sensor.

FIG. 16 illustrates spectral characteristics typical of an RGB camera sensor such as may be found in consumer-level digital cameras. Horizontal axis 1610 represents optical wavelengths within the visible spectrum from violet at the left to red at the right. Vertical axis 1620 represents the quantum efficiency (percentage of photons resulting in one electron of current) of a camera sensor sub-pixel. The dot-dot-dashed curve 1630 represents the spectral response of red or "R" sub-pixels of an RGB camera sensor. The dot-dashed curve 1640 represents the spectral response of green or "G" sub-pixels of an RGB camera sensor. The dashed curve 1650 represents the represents the spectral response of blue or "B" sub-pixels of an RGB camera sensor. Note that the quantum efficiency goes to zero for wavelengths shorter than about 380 nm, or stated more simply, RGB camera sensors generally to not respond to ultraviolet light.

These spectral responses are determined in large part by color filters placed in front of sub-pixels as part of the construction of the camera sensor. Often, the color filters include more green elements as compared to red or blue elements. This is because the human visual system peaks in sensitivity in the green spectral region (e.g., peaks at approximately 550 nm wavelength). Thus, the abundance of green sensor pixels in the imaging device allows for approximating the color response of the human visual system.

As can be seen, the spectral response curves are quite broad and overlapping. For conventional digital camera purposes, this has the advantage that there is no visible light wavelength for which a color digital camera is blind. However, from the perspective of quantitative spectral analysis, the broad and overlapping spectral characteristics is a disadvantage because the absorption characteristics of particles of interest (e.g., grass pollen) may be much more narrow. Thus, in some cases, it can be very difficult to distinguish and discriminate different particle types based on color using a broad and overlapping emission spectra to illuminate the particles.

A close look at the spectral profiles in FIG. 16 reveals a significant amount of what may be described as "color crosstalk." For example, even red light at a wavelength of 700 nm will not only excite red RGB pixels with a quantum efficiency of about 35 percent, but also excite "green" RBG pixels with a quantum efficiency of order 10 percent and excite "blue" RGB pixels with a quantum efficiency of order 5 percent. It is an over-simplification to say that "red" RGB pixels detect "red" light, "green" RGB pixels detect "green" light and "blue" RGB pixels detect "blue" light. For a deeper appreciation of the system discussed herein, and in particular various embodiments of the illumination hardware 224 (FIG. 2) presented further below, it is useful to keep this fact in mind.

In conventional applications of RGB camera sensors, such as in color digital cameras, color digital microscopes, and so forth, it is taken for granted that associated lens assemblies must be achromatic so that the red, green and blue sub-pixel images are all brought to an equally sharp focus. RGB camera sensors are conventionally associated with achromatic optics. The requirement that RGB camera optics be achromatic adds to the complexity of the optics, and hence its cost, particularly if a relatively large aperture is required.

Figure 17:
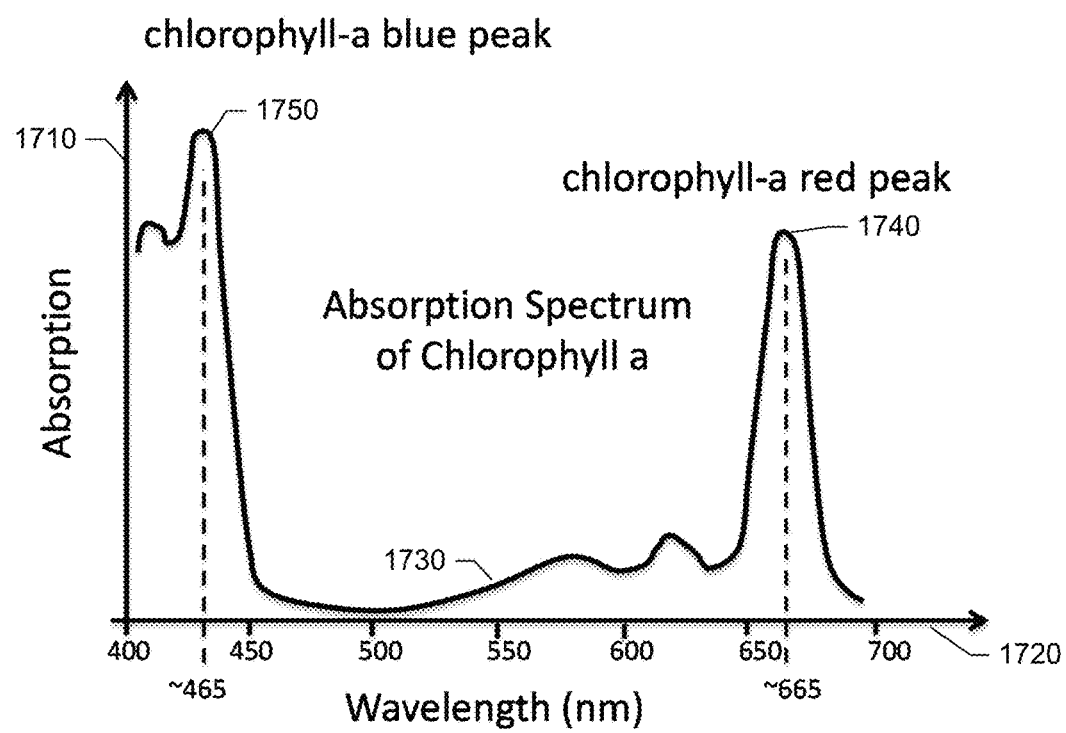
FIG. 17 is a graph showing the absorption spectrum of chlorophyll-a.

Fortuitously, the spectral widths that are possible from illumination sources using quantum dots is a good match to the spectral widths of, for example, the absorption peaks of chlorophyll-a as shown in FIG. 17. FIG. 17 shows an absorption spectrum of chlorophyll-a. With a vertical axis 1710 representing absorption strength and a horizontal axis 1720 for light wavelength, a curve 1730 shown in FIG. 17 represents the absorption spectra of chlorophyll-a.

This absorption spectrum has a pronounced "chlorophyll-a red peak" 1740 and a pronounced "chlorophyll-a blue peak" at 1750. In the plot of FIG. 17, the two absorption peaks are centered near 665 nm and 465 nm wavelengths. As one of skill in the art would recognize, the solvent solution environment of the chlorophyll-a has a significant effect on the locations of the peaks. Thus, depending upon factors such as the solvent solution environment, the location of the peaks may differ such as for chlorophyll-a on grass pollen. It should be appreciated that the principles of choosing quantum-dots based on the locations of the peaks remain the same.

The presence of chlorophyll-a distinguishes grass pollens from other pollens as well as other particles, and hence a quantum-dot illumination source tuned to an absorption peak of chlorophyll-a is of interest in the identification of allergenic grass pollens. Like plants, fungi also produce pigments with distinctive colors, such as the bright red of deadly red cap mushrooms. In an embodiment, quantum-dot illumination sources may be tuned to characteristic absorption peaks of certain fungal spores.

Figure 18:
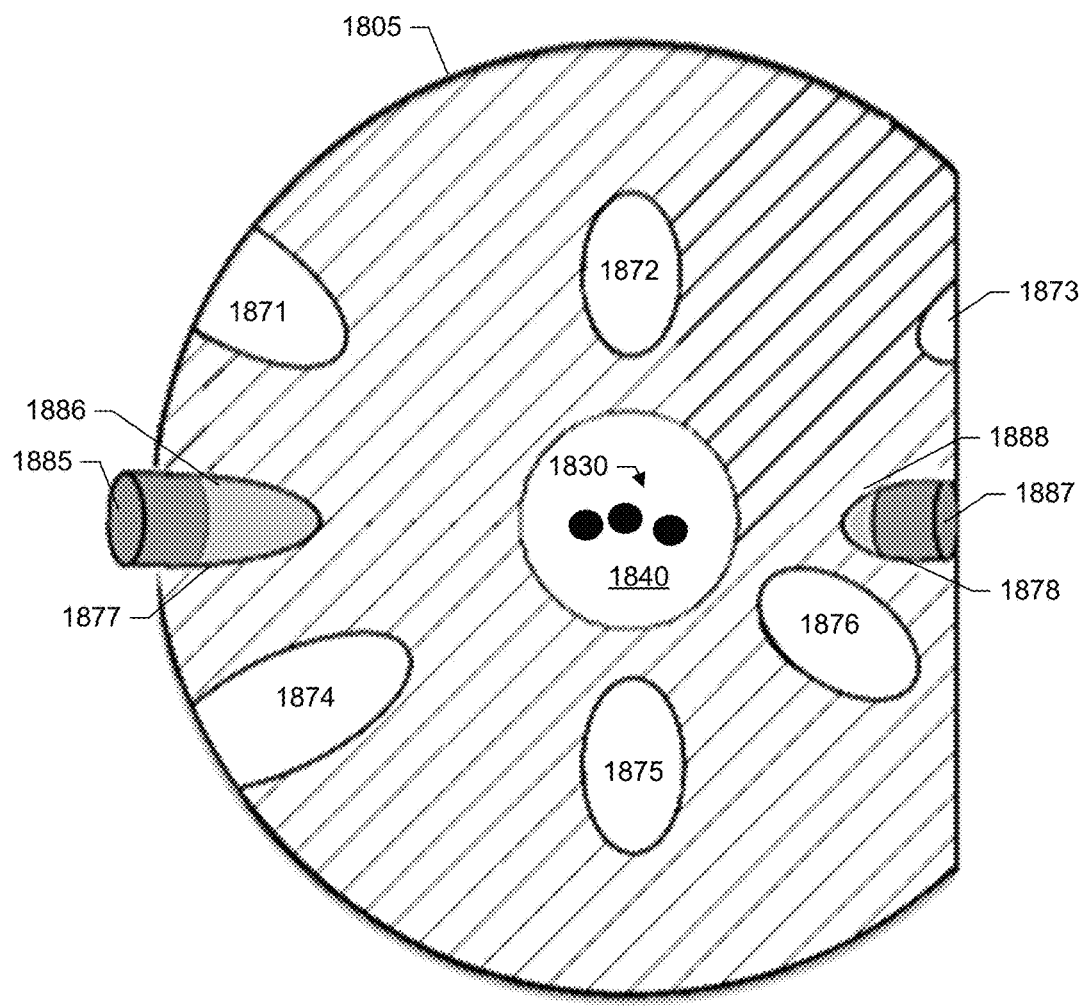
FIG. 18 shows a top view of an inspection platform of a particle monitor according to another specific embodiment.

FIG. 18 shows a top view of a platform 1805 of another specific embodiment of a particle monitor. FIG. 18 illustrates an example with eight illumination sources or channels 1871, 1872, 1873, 1874, 1875, 1876, 1877, and 1878. The illumination channels have been drawn in FIG. 18 with varying shapes to represent different azimuthal and polar angles. In FIG. 18, variations in polar angle result in variations in distances from center in plan view. For example, illumination sources 1872 and 1875 have the same polar angle but 180-degree opposite azimuthal angles.

Each illumination channel may include a light emitting element and an optical shaft. For example, illumination channel 1877 includes a light emitting element 1885 connected to an optical shaft 1886. Illumination channel 1878 includes a light emitting element 1887 connected to an optical shaft 1888. An illumination source may or may not be associated with a set of quantum dots. An illumination source may emit visible light (e.g., wavelengths ranging from about 390 nm to about 700 nm), UV light (e.g., wavelengths ranging from about 10 nm to about 380 nm), or infrared light (e.g., wavelengths ranging from about 700 nm to about 1 mm).

The light emitting elements and optical shafts for the remaining illumination channels have been omitted for clarity. In other words, additional light emitting elements (not shown) may be installed in additional illumination channels 1871-1876. Each illumination source has an illumination axis that intersects the particle inspection zone 1840. Illumination axes corresponding to different illumination sources may vary in azimuthal angle as well as angle with respect to an optical axis passing through a particle inspection zone 1840 having particles 1830, through a lens assembly, and to a camera sensor. Having many different illumination axes further provides for additional dimensions of analysis. For example, the lengths of different shadows resulting from shining light at different angles can indicate the height of a particle.

Compared to fluorescence images under UV light illumination, images from visible light scattering are more sensitive to the illumination direction. This is because while incoming directions of UV excitation photons have little influence on the outgoing directions of fluorescently emitted photons, the incoming directions of illuminating visible light photons have a strong influence on the outgoing direction of corresponding scattered photons. For example, placement of a UV light source in illumination channel 1877 results in essentially the same camera sensor fluorescent-light image as for the placement of the UV light source in illumination channel 1878.

However, placement of a white visible light source in illumination channel 1877 results in a strikingly different camera sensor image of visible scattered light as for the placement of the white visible light source in illumination channel 1878.

An everyday example of this effect is that waves on a lake sparkle very differently when the sun is near the horizon than at high noon. This analogy with light scattering off water surfaces is not far afield because fungal spores and other biological particles of interest are often transparent like water or semi-transparent under visible light. Visible light will often be scattered at the air/spore-material boundary surface much as light is scattered from air/water boundary surfaces. The nature of visible light scattered from a transparent spore is similar to the nature of light scattered from a transparent glass object.

Depending on lighting conditions, some surfaces of glass objections don't reflect light towards our eyes is not visible to us. Similarly, reflected light images of spores may give a complete picture of spore geometry. Camera sensor images of scattered visible light are strongly biased by the illumination direction of the light source, while fluorescent light images are largely independent of the illumination direction of the UV light source. The illumination direction bias of the visible light image complicates comparisons of fluorescent-light images with scattered-visible-light images.

Using multiple illumination directions may significantly reduce the illumination-direction bias of scattered-visible-light images of camera sensor 1420. For example, in one embodiment, a UV light source is placed in illumination channel 1878 while three separate white-light LEDs are placed in illumination channels 1872, 1875 and 1877. By way of example, directions of illumination channels 1875, 1877, and 1872 may be separated from each other by right angles in the plan view of FIG. 18 and vary in polar angles; other directions and other numbers of white-light LEDs may also be used. Also visible-light sources that are not white-light LEDs may also be used, such as a red laser (resulting in visible light scattering data being largely contained in red RBG camera sensor pixels while green and blue fluorescence signals are largely contained in blue and green camera sensor pixels). By combining scattered light signals corresponding to the three visible-light illumination directions, the illumination-direction bias is much reduced. Several means are available to combine the scattered light signals. White light sources in illumination channels 1872, 1875 and 1877 may be turned on simultaneously during image capture.

Alternatively, in another specific embodiment, the three white-light sources are turned on sequentially during the camera sensor exposure period. In this specific embodiment, a particle monitor includes a particle inspection zone and first, second, and third white-light sources above the particle inspection zone. The first, second, and third white-light sources may be arranged to provide illumination of the particle inspection zone at different angles. A first distance is from the particle inspection zone to the first light source. A second distance is from the particle inspection zone to the second light source. A third distance is from the particle inspection zone to the third light source. The first distance may be different from the second distance, third distance, or both. The first distance may be the same as the second distance, third distance, or both.

The first, second, and third light sources may form first, second, and third vertices of a triangle. A first side of the triangle is between the first and second vertices. A second side of the triangle is between the second and third vertices. A third side of the triangle is between the third and first vertices. Lengths of the first, second, and third sides of the triangle may be equal (e.g., equilateral triangle). A length of at least one of the first, second, or third sides may be the same as or different from a length of at least another of the first, second, or third sides.

A method may include activating the first light source and capturing a first image while the first light source is activated; activating a second light source and capturing a second image while the second light source is activated; and activating a third light source and capturing a third image while the third light source is activated. During the capturing of an image, two or more light sources may remain activated. For example, during the capturing of the second image, the first and second light sources may remain activated. Alternatively, during the capturing of the second image, the first light source may be deactivated while the second light source remains activated. During the capturing of the third image, the first, second, and third light sources may remain activated. Alternatively, during the capturing of the third image, at least one of the first or second light sources may remain deactivated.

A further option is to capture and separately digitize the visible light images corresponding to the three different illumination directions and then digitally combine the three images in software. By whatever means, combing signals for multiple white-light illumination directions provides a less biased scattered visible light image for use in determining outlines of particles and for comparing with UV fluorescent images.

The light emitting elements may vary in the nature of their emitted light. For example, illumination hardware 224 (FIG. 2) may provide local processor 240 many illumination options such as white-light illumination, UV illumination, infrared illumination, and visible light illuminations of various color characteristics. Local processor 240 may activate individual light sources one-at-a-time, or activate two or more light emitting elements simultaneously or concurrently.

Figure 19:
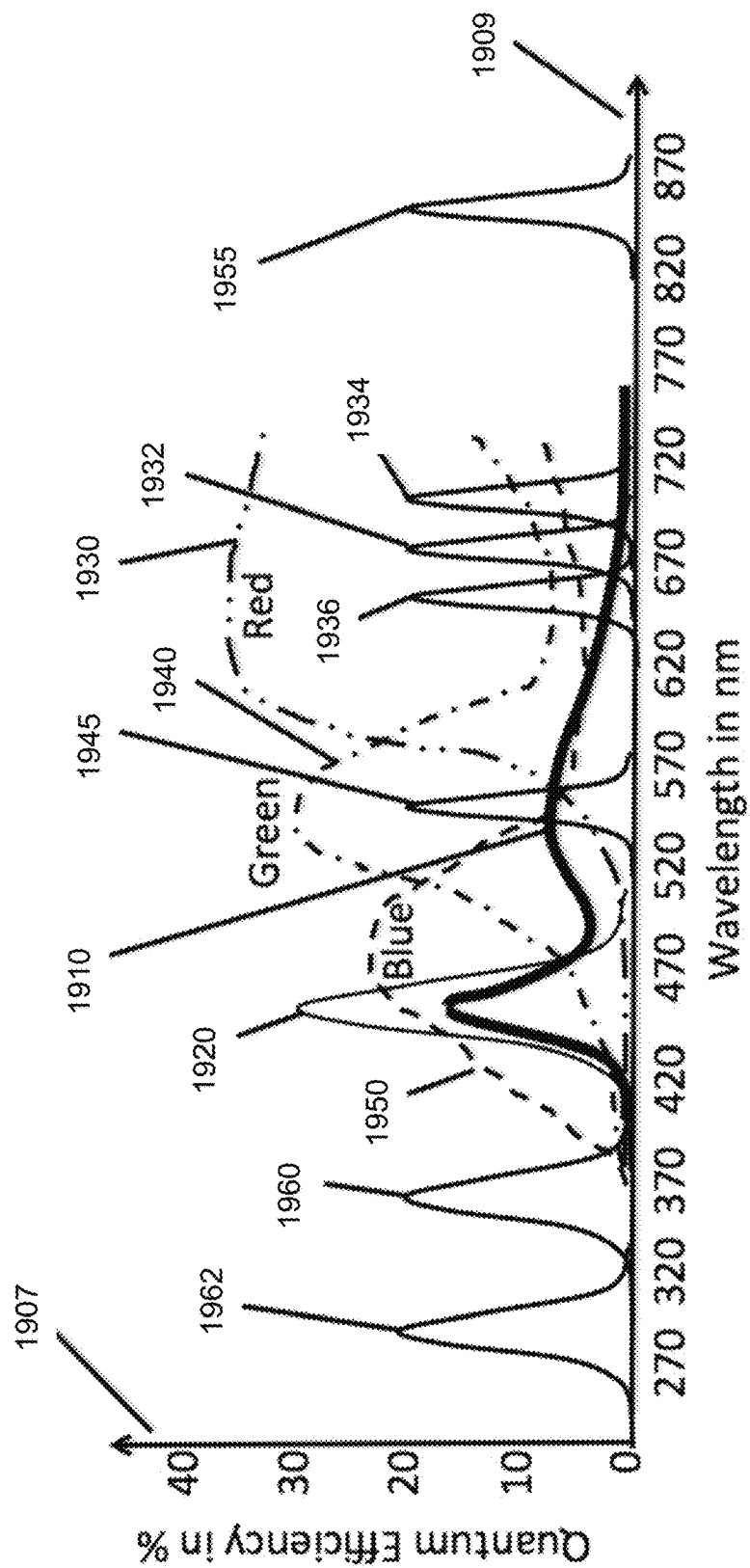
FIG. 19 shows a plot combining camera-sensor sub-pixel spectral characteristics as shown in FIG. 16 with illumination source spectral characteristics.

FIG. 19 shows a plot combining camera-sensor sub-pixel spectral characteristics as shown in FIG. 16 with illumination source spectral characteristics. Vertical axis 1907 represents the quantum efficiency (percentage of photons resulting in one electron of current) of a camera sensor sub-pixel. Horizontal axis 1909 represents optical wavelengths spanning from the near ultraviolet to the left, the visible spectrum from violet at the left to red in the middle, and near infra-red to the right. The horizontal axis of FIG. 19 is expanded relative to the horizontal axis of FIG. 16. This was done to include UV and infra-red light sources.

The dot-dot-dashed curve 1930 represents the spectral response of red or "R" sub-pixels of an RGB camera sensor. The dot-dashed curve 1940 represents the spectral response of green or "G" sub-pixels of an RGB camera sensor. The dashed curve 1950 represents the represents the spectral response of blue or "B" sub-pixels of an RGB camera sensor. FIG. 19 shows the quantum efficiency curves for red, green and blue camera sensor sub-pixels. Relative to FIG. 16, the horizontal wavelength axis has been extended in FIG. 19 to include ultraviolet (UV) light at shorter wavelength and near infrared (IR) light at longer wavelengths.

FIG. 19 adds emission spectra of value illumination sources (for which the vertical axis has arbitrary units unrelated to quantum efficiency). Heavy solid curve 1910 is representative of the emission spectra of white-light LEDs. White-light LEDs are fundamentally blue LEDS, hence the emission peak in the blue, to which phosphors have been added to convert much of the blue light into a broad spectrum of longer wavelength light, hence the broad spectral peak to the right.

In many embodiments, such a white-light LED is the primary illumination source used to produce images for particle shape (morphology) analysis as well as a basic, first pass color analysis. This first pass color analysis is largely based on color as perceived by the human eye. It is worth keeping in mind, there is much more color information that can be perceived by the human eye.

Curve 1920 represents the emission spectra of a blue LED. While a white-light LED may be used to excite fluorescence of quantum-dots, it is more efficient to do so with a blue LED.

Curve 1932 represents the emission spectrum of quantum dots tuned during manufacture to emit red light at the absorption peak of chlorophyll-a within grains of grass-pollen. This "chlorophyll-a red" emission may be fluorescently exited by, for example, light from a blue LED, or excited directly electronically. Curves 1934 and 1936 illustrate spectra of quantum-dots tuned to emit light of wavelengths just above and just below the chlorophyll-a red wavelength.

A strong signature for the presence of chlorophyll-a is strong optical absorption of red light of the spectrum of curve 1932 but not of red light of the spectrum of curves 1934 and 1936.

An approximation of full spectral analysis of objects viewed with a camera sensor is possible with a sufficient number of quantum-dot illumination sources. Consider, as an example, extending the set of spectral curves 1934, 1932 and 1936 in both directions of increasing and decreasing wavelength in order to cover the entire visible spectrum. While not providing the same fine color resolution of a scientific grade spectrometer, a device with between 10 and 100 quantum-dot illumination sources may still provide an approximation of a full spectral analysis at each camera-sensor pixel location that provides useful information at relatively low cost.

Even for analysis of shape information (morphological analysis) that does not make use of color, the narrow spectral widths of quantum-dot emission may be helpful. Consider, as an example, a lens system that is subject to chromatic aberration, either as a cost saving measure or due to the use of an electronically controlled variable lens (in combination with a stronger fixed lens). In such a scenario, illumination with the green quantum-dot spectrum of curve 1945 will largely eliminate chromatic aberration effects and produce sharper images for morphological analysis.

Useful spectral information is not limited to the visible spectrum. For example, it may be of interest to illuminate particles of interest with a near infrared LED, for example, at a wavelength of 850 nm. As illustrated by curve 1955, sufficiently "near" infrared light, that is with sufficiently short wavelengths, may still be transmitted by common lens materials and be detectable by a conventional camera-sensors. In some applications, the near infrared properties of particles may be of value.

Typically, common lens materials block ultraviolet light. This may be used to advantage when particles of interest are illuminated by UV light, resulting in fluorescent light of longer wavelengths that are detected by the camera-sensor while the illuminating UV is not. This isolates the interesting fluorescence signal from simply scattered UV light. UV fluorescence is of particular value in distinguishing between inorganic particles and particles of biological origin.

Curve 1960 is representative of common 365 nm UV LEDs. This UV wavelength is sufficiently short to fluorescently excite flavins such as riboflavin and related biomolecules, but too long to strongly excite most other biomolecules, hence a 365 nm UV LED can be used to probe flavin content of biological particles of interest.

Curve 1962 represents the emission spectra of a shorter wavelength UV LED, with the ability to fluorescently excite trytophan, an aromatic amino acid within proteins. Even shorter UV wavelengths may be used to fluorescently probe further sets of biomolecules.

By probing both flavins and protein content, a pair of UV LEDs provides a two-dimensional probe of particle biochemistry. In a like manner and for similar purposes, additional UV LEDs may be included where each UV LED (or cluster of UV LEDs) emits UV light of differing energies. While less powerful than a wet-laboratory bio-assay, such optical probing of particle biochemistry has the advantage of providing immediate, if crude, biochemical information, with which to aid in real-time particle type discrimination. Because biomolecules have varying degrees of stability, particularly those with conjugated bonds associated with fluorescence, their presence or absence may correlate with the metabolic health of a biological particle such as a fungal spore. Thus, UV fluorescence images can be analyzed by the particle monitor to not only make an identification of the species of a biological particle such as a fungal spore, but to also distinguish between different states of health of the biological particle.

FIG. 20 shows a flow chart illustrating some basic ingredients of automated particle (e.g., spore) monitoring according to a specific embodiment. This flow chart illustrates a method of spore detection. In brief, in a step 2010, a spore monitor samples ambient air such as via a blower that sucks in the ambient air. In a step 2020, mold spores, pollen, or both captured from the ambient air is transported to an illumination zone. For example, there can be a supply reel and a take-up reel to transport a sticky tape with adhesive side up past the air-inlet/blower. Fungal spore and other particles that stick to the adhesive are transported to the illumination zone which is provided by one or more illumination sources, some of which may be ultraviolet illumination sources.

In a step 2030, one or more illumination colors are selected. In a step 2040, the pollen is illuminated. The selection of the illumination colors may be based on a pre-determined illumination sequence that is stored by the monitor. The particle (e.g., spore) monitor may access the pre-determined illumination sequence in order to identify the color (e.g., wavelength) of light that should be emitted. The selection may be controlled by a computer. The computer selects an illumination source(s) with desired spectral properties. The selected illumination sources are then activated.

In an embodiment, the illumination sequence may be determined dynamically. A method may include illuminating the captured particles under white light, while the particles are being illuminated by the white light, capturing a first image of the particles, identifying, from the first image, colors of the particles, based on the colors of the particles as revealed by the first image, and selecting another color, different from white, with which to illuminate the particles for a second image of the particles. For example, RGB images collected under white light illumination may contain yellow particles of a shape possibly indicative of grass pollen grains. As discussed previously, the interpretation of the imaged pollen grains being grass pollen may then be tested by using quantum-dot illumination sources corresponding to spectral curves 1932, 1934 and 1936 of FIG. 19.

In a step 2050, the monitor performs an optical detection. The optical detection may include capturing an image of the particles under the illumination. In other words, while the sampled spore or pollen is illuminated, a lens array and an RGB camera sensor capture images of the sampled spore or pollen.

Steps 2030-2050 may be repeated 2052 any number of times in order to capture further color information about the sampled particles (e.g., pollen or spores) and other detected particulates. In a step 2060, the optical data (e.g., images of particles) is analyzed. In a step 2070, the optical data (e.g., images) may be transmitted to a remote server.

In an embodiment, as discussed above, the particle monitor can be connected to a network. The connection to a network allows the particle monitor to receive updates. An update may include, for example, updates to the illumination sequence, updates to image capture settings, or both. An illumination sequence stored at the particle monitor may specify the order for activating the different illumination sources. The image capture settings may specify focal depths or depths of focus. For example, three-dimensional morphology information may be obtained through a sequence of depths of focus corresponding to different horizontal layers of a translucent particle such as a fungal spore. The ability to update the particle monitor remotely or over a network helps to ensure use of the latest algorithms for quickly and accurately identifying or discriminating particles.

In a specific embodiment, aspects and principles of the system may be applied to monitoring a vineyard for agriculture diseases or agricultural pathogens. In this specific embodiment, the collection cartridge can be hand-held by a user for a manual collection of particles that may have collected on a surface of a leaf or grape of a grape vine. In this specific embodiment, a method may include holding a collection cartridge, the collection cartridge comprising an adhesive coated tape and a slot through which a portion of the tape is exposed; positioning the slot to face an object; pressing the cartridge against the object to bring the portion of the tape into contact with a surface of the object, thereby transferring particles on the surface to the tape; and inserting the cartridge into a particle monitor for an analysis of the particles. The object may include a leaf, such as a grape leaf, or a grape such as from a grape vine. The types of particles of interest to identify may include small pests, insects, bacterium, mildew, fungal spores including mold spores, or combinations of these.

Examples of airborne fungal spores of interest to vineyards may include powdery mildews such as *Erysiphe necator, Eutypa Lata, Botrytis*, and *Cladospora* mold among others. Mildew is a fungus. Powdery Mildew (*Erysiphe necator*) is widely considered to be the most problematic of all the vineyard molds. In an embodiment, the particle monitor is configured to discriminate the spore health of powdery mildew.

Detection of such mold may be transmitted to a mobile app on the vineyard owner's mobile device. The system can provide counts, trends, and predictive data and analytics displayed via a web application or mobile application. The application allows for customizing alerts for efficient vineyard management operation. The system can provide up-to-the minute information on invasive, disease causing molds, pollens, and weeds. Winds, for example, can carry disease spores for miles. It is desirable to distinguish between harmful and benign molds for successful fungicide operations. The system allows for 24/7 monitoring and is much more cost-effective than microscopic inspection and visual spot checks. Early disease detection and control can increase yield and product quality.

In an embodiment, systems and techniques are provided for the detection and classification of airborne particles (e.g., pollens, molds, dander, heavy smoke (ash) particles, sand/silica, asbestos, and many others). Systems and techniques are provided for detecting and counting particles having a size (e.g., a longest dimension) from about 1 um to about 1500 um. In an embodiment, a minimum particle resolution is about 0.3 um. In another embodiment, a minimum particle resolution is about 0.1 um). In an embodiment, a light-based methodology includes multiple different analysis techniques including deep neural network machine learning and advanced algorithms to extract unique particle signatures leading to classification.

A media cartridge is provided that captures particles for physical record archiving, future studies, advanced studies in a laboratory, or combinations of these. An analysis may include particle feature extraction, vector extraction, executing a classifier algorithm, particle classifications, and aggregating the information into a results file, or combinations of these. The results file may be transmitted to a user's mobile device for display. Particle detection techniques may include morphology (e.g., shape and size), UV fluorescence (e.g., flavin, NADH & protein excitation), colorimetry (e.g., color parameters), topography (e.g., height and texture), internal structure, or combinations of these.

Particle monitoring apparatus and methods have been described above that provide systems and techniques to identify the types of airborne biological particles. For example, airborne particles may be identified as a spore of a particular species of fungus or a pollen grain of a particular type of flowering plant. Advantageously, such apparatus and methods may be used to not only identify the types of biological particles, but also recognize the state of biological particles. For example, in the control of agricultural pathogens, when a particular disease causing fungal spore is detected, it is of interest to know if the spore is in a healthy and hence virulent state, or in a sterile state as may result from exposure to a fungicide.

Figures 20, 21A:
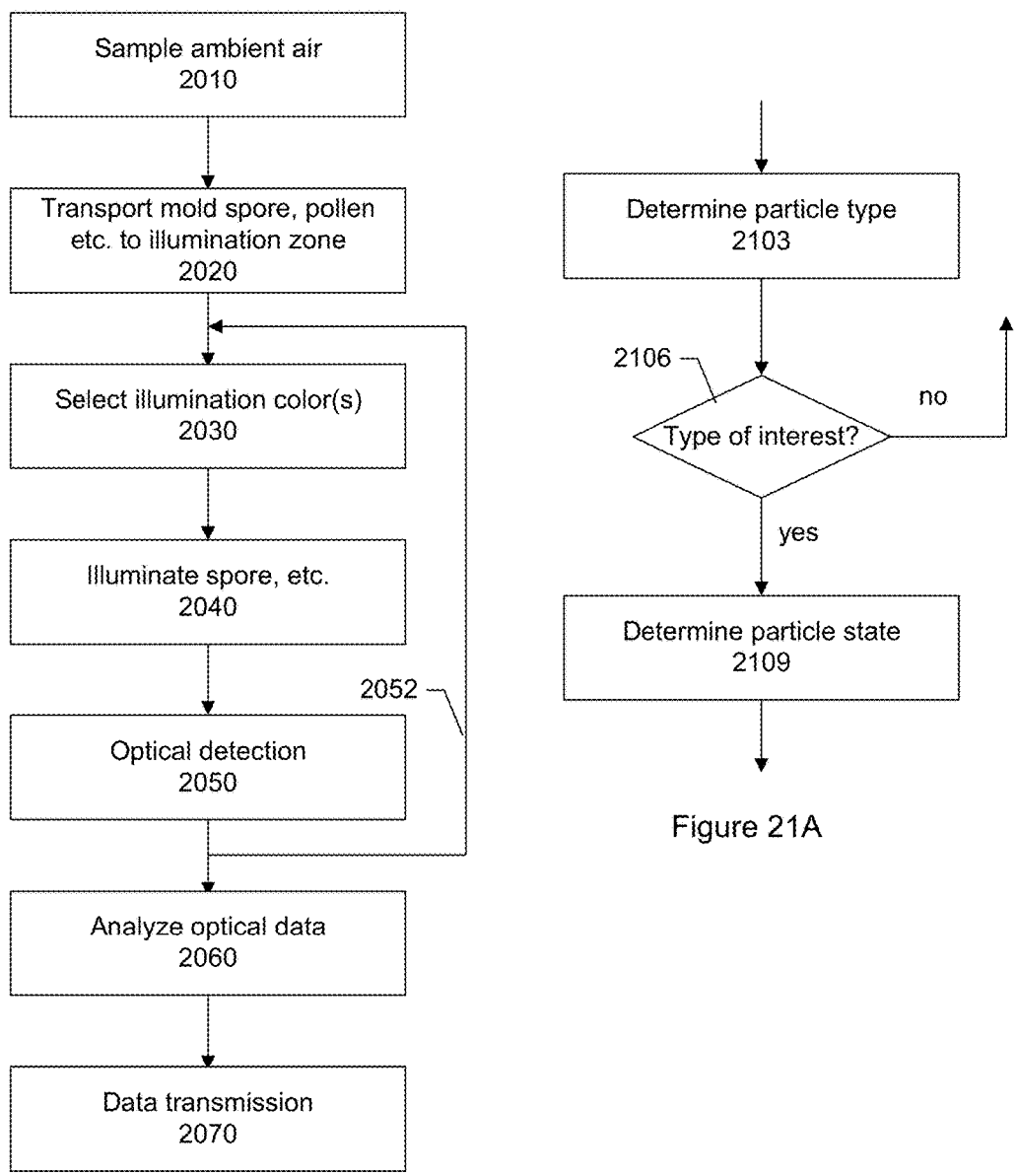
FIG. 20 shows an overall flow illustrating some basic ingredients of automated particle (e.g., mold spore or pollen) monitoring according to a specific embodiment.
FIG. 21A illustrates a detail of interpretation 230 of FIG. 2 involving determination of particle state as well as type.

FIG. 21A shows a flow chart describing the extension of particle identification to the determination of the state of a particle. At step 2103, the type of a biological particle has been determined with apparatus and methods such as described above. For example, the particle may be identified as a fungal spore of powdery mildew or as a pollen grain of ragweed. At step 2106, it is decided if the determined particle type is of interest. For example, for a particle monitor at a vineyard, a particle identified as a grass pollen is not of interest and the particle monitor moves on to collect and analyze further airborne particles. However, if the vineyard particle monitor identifies the particle as a pathogenic fungal *botrytis* spore, the particle monitoring system moves on to step 2109. At step 2109, the particle monitoring system reaches a conclusion about the state of the biological particle.

In agricultural applications, it is of particular interest is to determine if the biological particle, such as a pathological fungal spore, is in a healthy virulent state or in an injured and sterile state. Other aspects of a biological particle's state may be of interest. For example, distinguishing between spores in a moist versus desiccated states may aid predictions on time of (humidity activated) fungal growth from spores. Distinguishing between sexually and asexually produced spores may provide information of interest relating to that nature of a fungal reproduction and infestation. These are illustrations where not only the type, also but the state of biological airborne particles is of interest to agriculture.

For non-agricultural applications such as personal pollen monitors, determinations of the state of airborne biological particles may also be of interest. The state of allergenic particles may well have an effect on a user's physiological reaction to exposure to a given number of the allergenic particles. For example, weakened UV fluorescence of pollen grains due to decomposition of fluorescing biomolecules with time or sunlight exposure may well correlate with decomposition of the pollen grain's allergenic biomolecules with time or sunlight exposure. Another example of a non-agricultural application for the system and techniques as discussed is the detection of airborne mold spores in support of mold inspection and mold remediation/removal from buildings. It is to be understood that the embodiments described below for agricultural applications illustrate principles that also apply to applications in other areas.

Figure 21B:
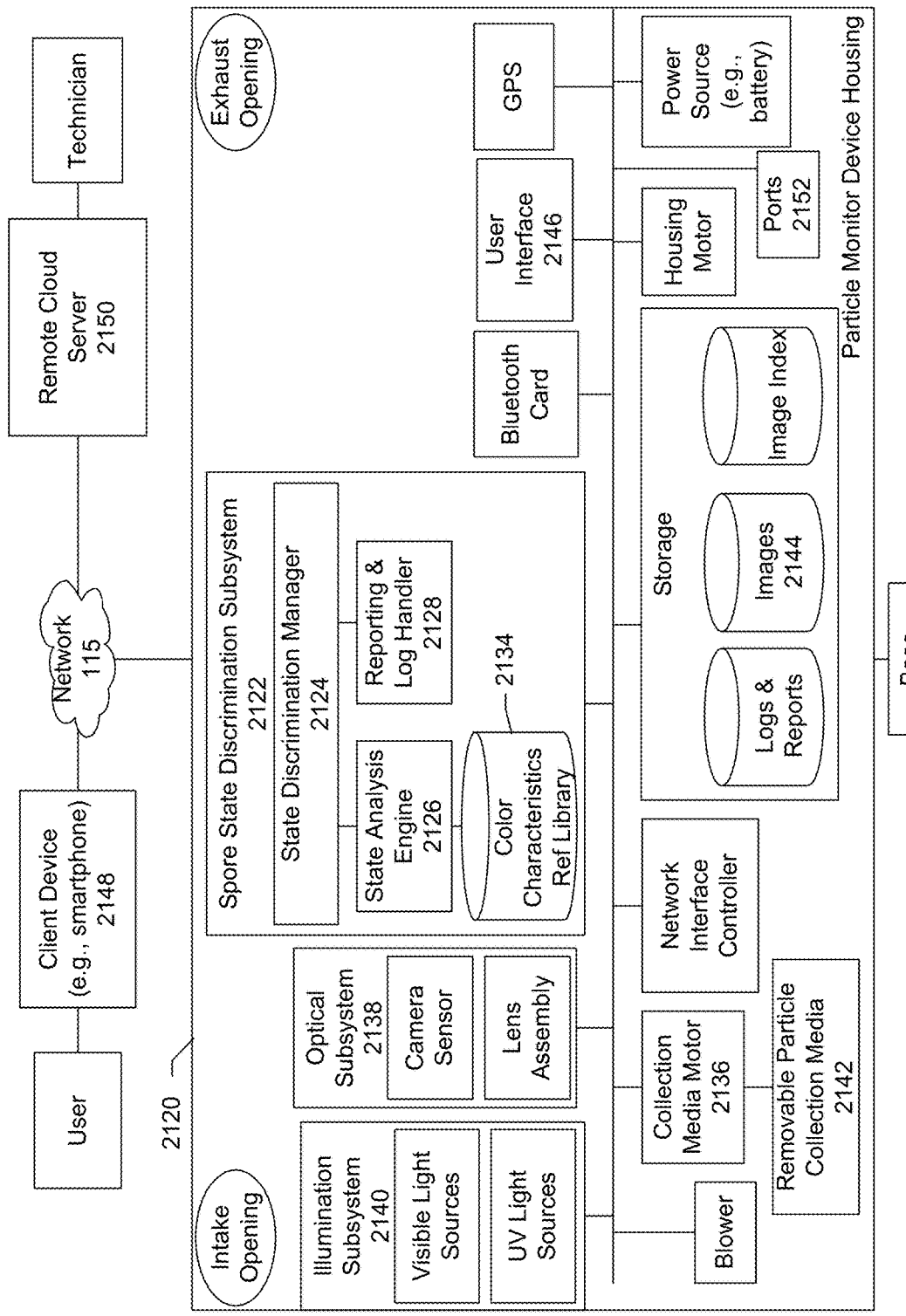
FIG. 21B shows a block diagram of a particle monitoring device for identifying a state of a particle according to a specific embodiment.

FIG. 21B shows a block diagram of a particle monitoring device 2120 according to a specific embodiment. The particle monitoring device shown in FIG. 21B is similar to the particle monitoring device shown in FIG. 3. The particle monitoring device shown in FIG. 21B, however, includes a spore state discrimination subsystem 2122. The state discrimination subsystem includes a state discrimination manager 2124, state analysis engine 2126, reporting and log handler 2128, and a reference database 2134 storing color characteristics of biological particles corresponding to illumination under various UV light. It should be appreciated that the blocks shown can be functional rather than structural so that it is possible to have many different hardware configurations that can perform the illustrated functions. Implementation of the functional entities may vary.

The state discrimination manager provides overall management of the processes to identify a state of a particle such as a fungal spore. In particular, the state discrimination manager is responsible for directing the operation of collection media motor 2136, optical subsystem 2138, and illumination subsystem 2140 to capture images of particles trapped within removable particle collection media 2142. In an embodiment, the collection media motor advances tape of the collection media having the trapped particles to a position underneath the optical subsystem. The illumination subsystem illuminates a portion of the tape having the trapped particles with various light including visible light and UV light. The optical subsystem captures images of the particles while the particles are being illuminated under each of the different lighting conditions.

The UV light sources include light sources capable of generating UV light of various spectral characteristics. For example, a first UV light source may provide UV light having a first spectral characteristic. A second UV light source may provide UV light having a second spectral characteristic, different from the first spectral characteristic. A third UV light source may provide UV light having a third spectral characteristic, different from the first and second spectral characteristics. And so forth.

The images may be stored in an image repository 2144. The discrimination manager retrieves the images from the image repository and passes the images to the state analysis engine for analysis. The color characteristics reference library stores a set of predetermined color characteristics of fluorescent light for various types of fluorescent biomolecules. In a specific embodiment, a predetermined color characteristic of fluorescent light for a fluorescent biomolecule of interest corresponds to a concentration of the biomolecule of interest in a fungal spore of a known state.

In a specific embodiment, these color characteristics of fluorescent light are associated with the fluorescent properties or attributes of fluorescent biomolecules of interest. Each predetermined color characteristic corresponds to excitation of a particular biomolecule of interest under UV light of a particular spectral characteristic.

For example, there can be a first color characteristic of fluorescent light for a first biomolecule of interest corresponding to the first biomolecule of interest being illuminated under UV light having the first spectral characteristic. The first biomolecule may be in a fungal spore of a known state (e.g., virulent or sterile). Thus, the color characteristic can be associated with the fungal spore of the known state.

Likewise, there can be a second color characteristic of fluorescent light for a second biomolecule of interest corresponding to the second biomolecule of interest being illuminated under UV light having the first spectral characteristic. There can be a third color characteristic of fluorescent light for a third biomolecule of interest corresponding to the third biomolecule of interest being illuminated under UV light having the first spectral characteristic. And so forth.

Likewise, there can be a first color characteristic of fluorescent light for the first biomolecule of interest corresponding to the first biomolecule of interest being illuminated under UV light having the second spectral characteristic, different from the first spectral characteristic. There can be a second color characteristic of fluorescent light for the second biomolecule of interest corresponding to the second biomolecule of interest being illuminated under UV light having the second spectral characteristic. There can be a third color characteristic of fluorescent light for the third biomolecule of interest corresponding to the third biomolecule of interest being illuminated under UV light having the second spectral characteristic. And so forth.

Likewise, there can be a first color characteristic of fluorescent light for the first biomolecule of interest corresponding to the first biomolecule of interest being illuminated under UV light having the third spectral characteristic, different from the first and second spectral characteristic. There can be a second color characteristic of fluorescent light for the second biomolecule of interest corresponding to the second biomolecule of interest being illuminated under UV light having the third spectral characteristic. There can be a third color characteristic of fluorescent light for the third biomolecule of interest corresponding to the third biomolecule of interest being illuminated under UV light having the third spectral characteristic. And so forth.

Thus, the reference library stores predetermined color characteristics of fluorescent light of various biomolecules of interest present in a fungal spore of a known state (e.g., virulent or sterile). The color characteristics correspond to the biomolecules of interest being illuminated with UV light of various spectral characteristics. Each predetermined color characteristic may be tagged with a first tag identifying a particular biomolecule of interest (e.g., flavin, NADH, or tryptophan), a second tag identifying a state of a fungal spore in which the particular biomolecule of interest is present, and a third tag identifying UV light of a particular spectral characteristic that was used to illuminate the fungal spore including the particular biomolecule of interest.

In an embodiment, the optical subsystem generates a color image of a trapped particle while the trapped particle is illuminated by the illumination subsystem with UV light of a particular spectral characteristic. The state analysis engine determines a state of a biological particle (e.g., fungal spore) by measuring from the color image a degree and color of fluorescence for each pixel within an outline of a fungal spore identified in the image. The analysis engine compares the measurements against the color characteristics reference library to identify which predetermined color characteristic of fluorescent light most closely matches the measurements. Upon identifying a matching predetermined color characteristic, a cross-reference can then be performed to the tag associated with the matching predetermined color characteristic storing the known corresponding state information.

Upon identifying the state, the reporting and log handler creates an entry in a log file. The entry may include a first field storing an identification of the particle (e.g., powdery mildew), a second field storing a timestamp indicating the time and date of particle capture, and a third field storing a determined state of the particle (e.g., virulent or sterile).

The results of the state determination may further be displayed on a user interface 2146. The user interface may include an electronic screen on which the results are displayed. Instead or additionally, the results may be transmitted to a client device (e.g., smartphone) 2148, remote cloud server 2150, or both. The transmission of the results may include a transmission of the images taken of the trapped particle. Instead or additionally, the particle monitor may include a port (e.g., USB port) 2152 in which the results, images, or both may be copied to a portable USB drive plugged into the port. For example, in some cases, there may not be network connectivity at the location where the particle monitor device has been deployed. In this case, the user can download the results, images, or both by traveling to the location of the particle monitor and connecting the particle monitor to a portable drive (e.g., flash drive).

FIGS. 21C-D show examples of results of the state determination that may be output by the particle monitor device. In particular, FIG. 21C shows an electronic screen 2172 identifying a particle detected (e.g., powdery mildew), a date and time of capture (e.g., Jul. 4, 2017), and a determined state (e.g., virulent). FIG. 21D is similar to FIG. 21C. In FIG. 21D, however, another powdery mildew particle has been captured at a later date (e.g., Jul. 6, 2017) and its state has now been determined to be sterile. As discussed, the state determination results may be displayed on an electronic screen of the particle monitor device, written to a log file at the particle monitor device, transmitted from the particle monitor device to a client device (e.g., smartphone), transmitted from the particle monitor device to a central server, or combinations of these.

Figure 22:
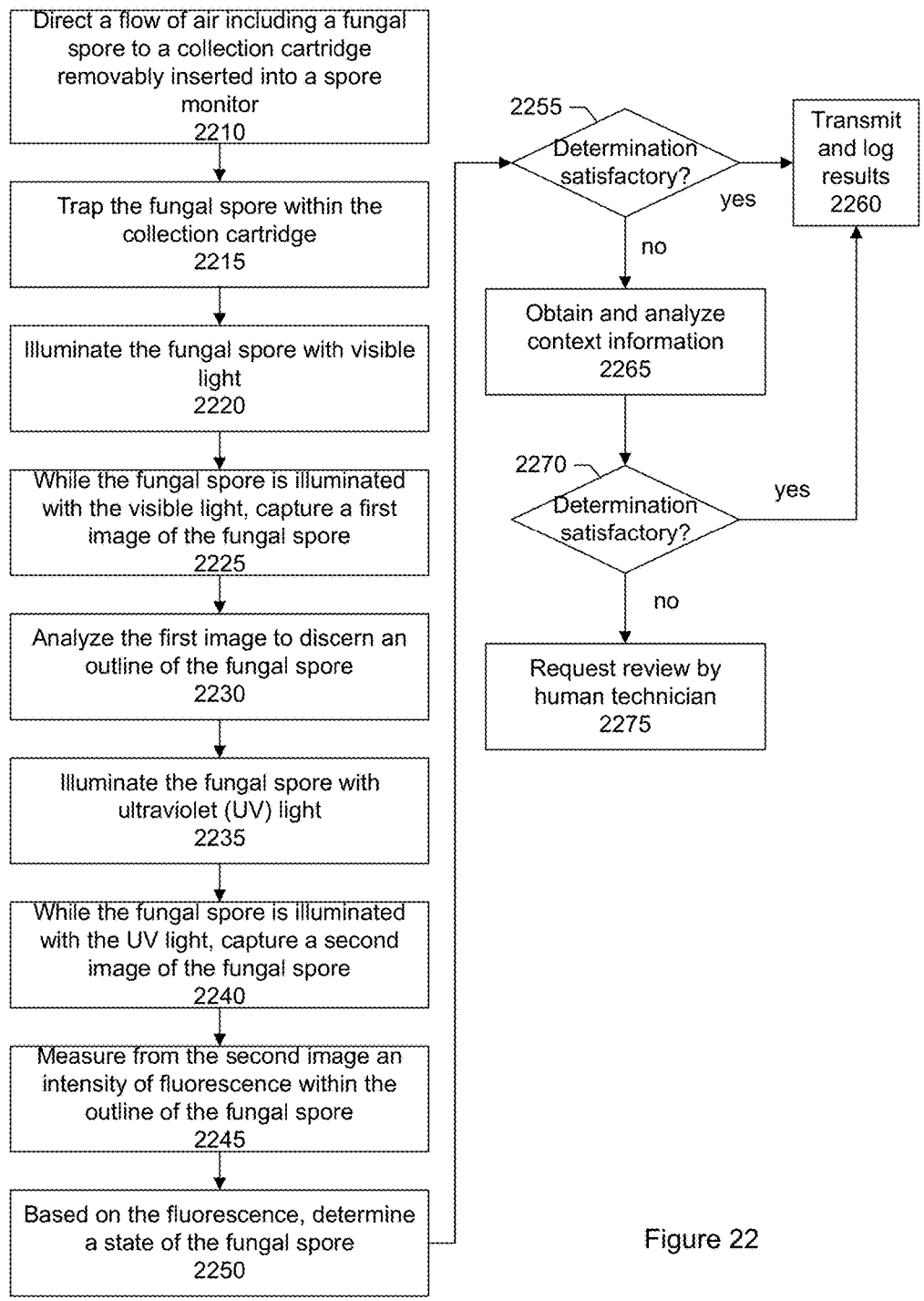
FIG. 22 shows an overall flow of a process for identifying and determining a state of a particle according to another specific embodiment.

FIG. 22 shows a flow chart of a process for determining a state or health of a particle such as a fungal spore. FIGS. 23-26 schematically illustrate images of fungal spores of interest to agricultural applications. In some cases, a fungal spore of interest is an undesired pathogen, but not necessarily. As a counter example, vitality of airborne fungal spores of a highly sought after gourmet truffle may be considered to be a good thing. In any case, it is of interest to know the health state of spores in order to anticipate their ability to initiate new fungal growths.

Referring now to FIG. 22, in a step 2210, a flow of air that may include a fungal spore is directed to a collection cartridge removably inserted into a spore monitor. In a step 2215, the fungal spore is trapped within or inside the collection cartridge. For example, the fungal spore may be trapped by an adhesive tape housed within the collection cartridge.

After the fungal spore has been trapped, the spore monitor advances a portion of the tape having the trapped fungal spore to the inspection zone. In a step 2220, the fungal spore is illuminated with visible light (e.g., wavelengths ranging from about 390 nm to about 700 nm. In a step 2225, while the fungal spore is illuminated with the visible light, the camera sensor of the spore monitor captures a first image of the fungal spore.

Figure 23:
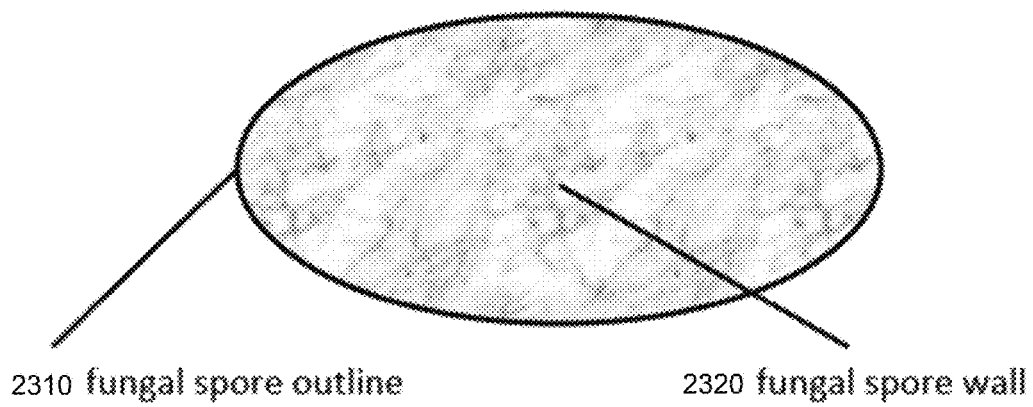
FIG. 23 is a schematic representation of a fungal spore image using visible light illumination.

FIG. 23 illustrates an image 2300 of a fungal spore illuminated by visible light such as white light. Such a visible light image can be used by the spore monitor to determine the shape and texture of the exterior fungal spore wall 2320, thus providing morphological information for use in the identification of the spore type. The visible light image may provide a clear determination of a fungal spore silhouette or outline 2310. In other words, in an embodiment, the spore monitor analyzes the first image to identify or discern an outline of the fungal spore (step 2230—FIG. 22).

In a step 2235, the fungal spore is illuminated with ultraviolet (UV) light. In a step 2240, while the fungal spore is illuminated with UV light, the camera sensor of the spore monitor captures a second image of the fungal spore. In a step 2245, the second image is analyzed to measure an intensity, degree, color, level of fluorescence, or combinations of these within the outline of the fungal spore.

In a step 2250, based on the intensity of fluorescence (or other measured attributes or combination of measured attributes), a state of the fungal spore is identified. In other words, the intensity of fluorescence can be used to determine the state or health of the trapped fungal spore. In an embodiment, there can be a predetermined threshold intensity. The measured intensity is compared to the predetermined threshold intensity. If the measured intensity is above the threshold, a determination may be made that the fungal spore is in a first state. If the measured intensity is below the threshold, a determination may be made that the fungal spore is in a second state, different from the first state.

Figure 24A:
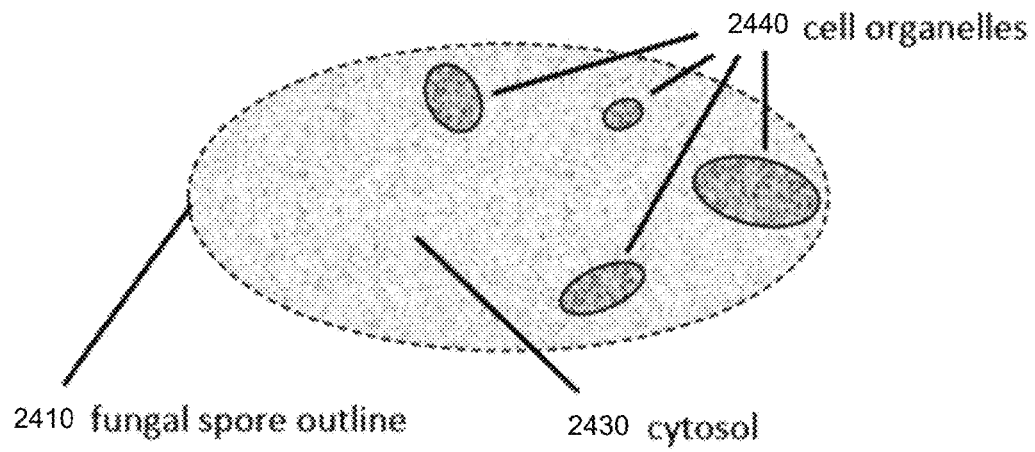
FIG. 24A is a schematic representation of a healthy fungal spore fluorescence image using ultraviolet light illumination.

For example, FIG. 24A illustrates an image 2400 of the UV fluorescence for a healthy fungal spore. Within the fungal spore, the density of fluorescing biomolecules may be different between the cytosol 2430 and different types of cell organelles, with certain types of organelles having the highest densities of fluorescing biomolecules. (Cytosol is the matrix fluid of the cell within the cell wall and within which are the cell's organelles.)

To take a specific example, consider 365 nm UV illumination resulting in fluorescence mainly of flavins and also a contribution from NADH (nicotinamide adenine dinucleotide). Flavins and NADH play a key role in cell respiration. The cell organelles known as mitochondria provide energy to other parts of the cell by consuming fuel such as glucose and energizing ATP molecules that then diffuse to other parts of the cell. (A fungal spore is a cell.) Flavins and NADH play a key role in energizing of ATP molecules and hence flavins and NADH may be expected to be present in higher concentrations at mitochondria. In an embodiment, a particle monitor includes a UV illumination source configured to generate and emit light at a wavelength of 365 nm. With 365 nm UV illumination, mitochondria may be the strongly fluorescing cell organelles 2440 and the cytosol 2430 may fluoresce relatively weakly within the fungal spore outline 2410.

For readers not familiar with the roles of mitochondria, flavins, NADH and ATP in cellular metabolism, the following analogy may be informative. Imagine a city whose energy needs are provided by a fossil fuel power plant. The power plant of the city is analogous to the mitochondria of a cell such as a fungal spore. Both the city's power plant and the cell's mitochondria use hydrocarbons (e.g., fossil fuel or glucose) as an energy source. The heat-driven turbines of the city's power plant are analogous to the "Krebs" or "citric-acid" cycle of biochemical reactions within the mitochondria. In analogy to energy from the city's power plant being delivered to homes of residents via electrical power lines, energy containing ATP molecules diffuse from the mitochondria through the cytosol to various organelles and other locations within the cell.

In other words, ATP molecules go to various locations including the cells outer membrane and the cytosol itself. At the city's power plant, an electric generator plays an essential role transferring energy from fossil-fuel powered turbines to the electrical power grid of the city. Flavins and the biomolecule NADH plays a role in the cell's energy system that is analogous to the electric generator of the city's power plant; flavins and NADH provide an essential energy-transfer link between the biochemical reactions of the Krebs or citric-acid and the energy transporting ATP biomolecules. Flavins and NADH are crucial to the cellular energy system. Flavins and NADH are essential to spore metabolism including respiration.

"NADH" is the higher energy form of the biomolecule "nicotinamide adenine dinucleotide" where the "H" refers to a hydrogen atom. If the hydrogen atom is removed, the result is the lower energy "$NAD^+$" form of nicotinamide adenine dinucleotide. The Krebs cycle "charges up" nicotinamide adenine dinucleotide molecules by converting $NAD^+$ into NADH. When NADH in turn "charges up" an energy carrying ATP molecule (by converting ADP to ATP), it reverts to its lower energy $NAD^+$ form.

These biochemistry details are of interest to biological particle monitoring devices as described herein because only the higher-energy NADH form of nicotinamide adenine dinucleotide fluoresces when illuminated by 365 nm ultraviolet light. The lower-energy $NAD^+$ form of nicotinamide adenine dinucleotide does not fluoresce. Hence the intensity of 365 nm UV fluorescence images of fungal spores is sensitive to the energy charge state of the nicotinamide adenine dinucleotide. If the respiration, including the Krebs cycle, of a fungal spore is shut down by a fungicide, spore mitochondria will no longer be able to convert lower-energy $NAD^+$ to higher-energy NADH and hence UV fluorescence due to NADH will fade.

Interestingly, in contrast to NADH, the fluorescing form of flavins is a lower-energy form of flavins while the "charged up" form of flavins does not fluoresce. Hence when mitochondria are actively metabolizing and producing energy for the spore, we may expect a higher ratio of NADH fluorescence to flavin fluorescence relative to a spore in a dormant state. Conversely, when mitochondria are not actively metabolizing and producing energy for the spore, a higher ratio of flavin fluorescence to NADH fluorescence relative to the spore in an active or charged state may be observed.

Figure 24B:
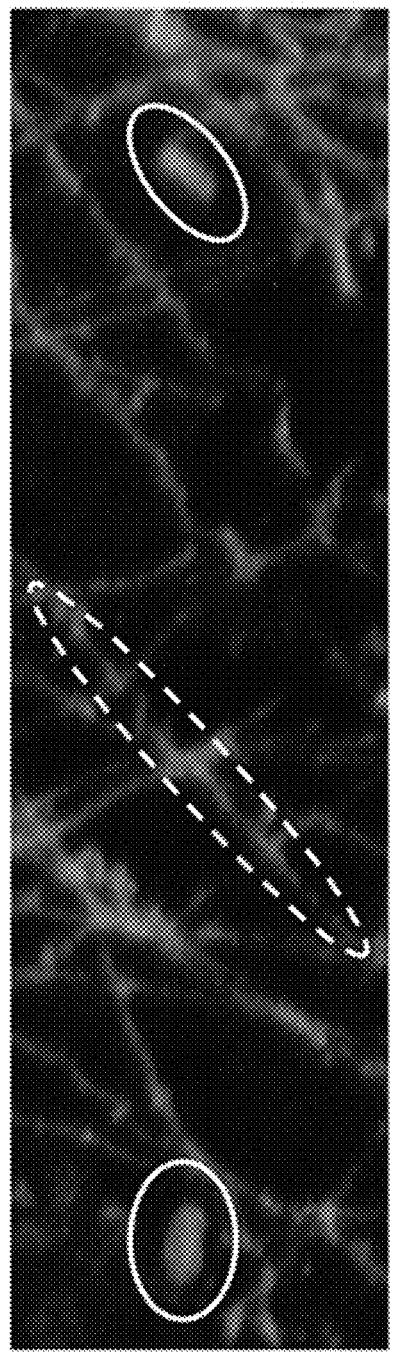
FIG. 24B shows an image of a mold particulate matter including spores fresh off a grape vine.
Figure 24C:
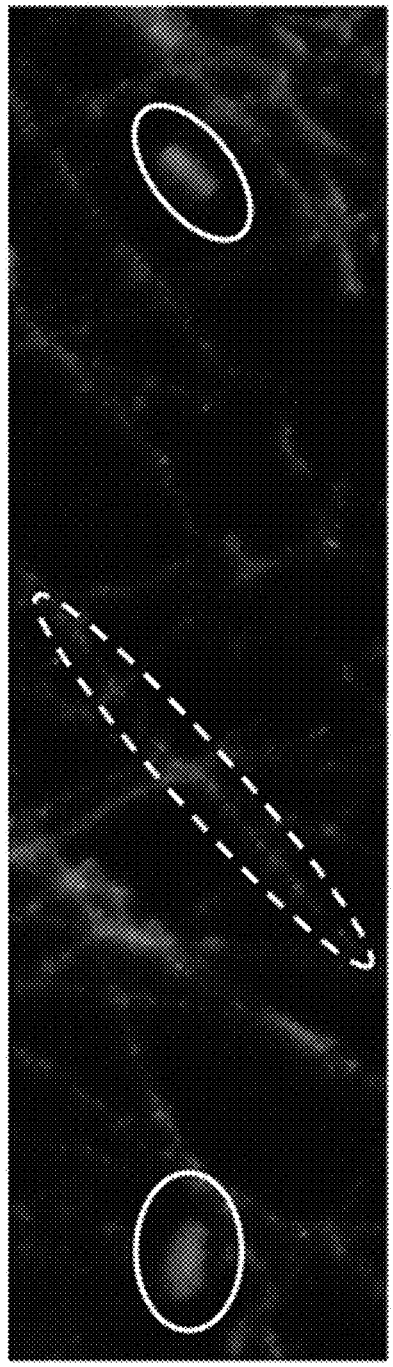
FIG. 24C shows an image of the mold particulate matter including spores fifteen hours later.

FIGS. 24B and 24C show images of mold material including spores. The image of FIG. 24B was captured shortly after the mold material was captured. The image of FIG. 24C is of the same mold material, but captured 15 hours later. Images of two mold spores are inside the solid circles of FIG. 24B and the same spores are also circled in FIG. 24C. The spores seen in these figures are about thirty microns long. Much of the other mold material in the images are "hyphae." Hyphae of mold are roughly analogous to roots or branches of plants. Hyphae are often in the form of long thin lines, such as the hyphae indicated by the dashed circle in FIGS. 24B and 24C. In this 15-hour interval, there was a change in the metabolic state of the imaged spores (and other mold parts such as hyphae).

In this experiment, a 340 nm UV LED source of the device was on for the entire duration of the test, running at 100 mA. And the laboratory ambient temperature ranged from about 70 to 75 degrees per day, while the humidity ranged from about 35 percent to 40 percent.

The images show that mold spores will change color over time as they age and their metabolic function changes. In particular, the color changes from a strong (high fluorescent) turquoise color to a more greenish color over time, such as over the 15-hour interval between the images of FIGS. 24B and 24C. In some cases, the morphology of the spore may change with time, such as becoming more long and narrow due to desiccation.

The particles captured by the cartridge adhesive of the prototype monitoring device included brand new healthy spores feeding from a grape bunch. In this experiment, the cartridge was removed from the particle-monitoring device, the adhesive touched on mold growing on the graph bunch, and then the cartridge reinserted into the particle-monitoring device. The images of FIGS. 24B and 24C are a portion of the field of view captured by the camera sensor. The grape bunch was located in a vineyard in Napa, Calif. known to have powdery mildew.

In this specific embodiment, a spore state is determined by employing a 340 nm UV excitation source in the monitoring device. A very healthy and young spore will have a turquoise color and a high degree of fluorescence (intensity) when captured using an imager of the monitoring device. With time, the fluorescence color may change (e.g., to green) and the degree of fluorescence (intensity) may fade. The morphology or shapes of the fluorescent light images may also vary as the state of the spore changes. The use of a fungicide will accelerate the changes in the spore state within a few hours of being mortally wounded.

The environment plays a big role in the life of a spore. As an example, grape powdery mildew spores can live up to 60 days in a perfect environment that helps it thrive and then die of age. Certain fungicides may "kill" a spore within minutes while others may disable its reproductive ability, thus altering their metabolic functions. An older spore having very low metabolic function will die faster than a young one when wounded by fungicides.

For a UV excitation wavelength of 340 nm (between the 325 nm and 365 nm examples given by the dot-dot-dashed lines in FIG. 28S), NADH and riboflavin are the only fluorescing biomolecules that we are expecting. A 340 nm wavelength is too long (photon energy too low) to excite tryptophan in proteins or any other biomolecule that fluoresces in response to shorter UV wavelengths. NADH only fluoresces in its high-energy state (the lower-energy NAD+ state does not fluoresce) while riboflavin is the opposite in that only its lower-energy state fluoresces. Neither molecule will fluoresce after they have decomposed. Furthermore, as seen in FIG. 28S, the higher-energy form of NADH emits blue (about 455 nm) fluorescent light while the lower-energy form of riboflavin emits green (about 520 nm) fluorescent light. Given this scientific information, the following mapping between UV fluorescence behavior and metabolic state may be expected to apply in many cases. Depending on the application different mappings may apply.

Blue (Turquoise) fluorescence may indicate a metabolically active state. Metabolic activity will put a significant fraction of NADH/NAD+ molecules in their higher-energy "NADH" state in which they are holding a hydrogen "H" ready for use in metabolic reactions; hence this metabolically active state will emit blue fluorescent light. Much of the riboflavin will also be in a higher-energy state and hence not fluorescing but some riboflavin will remain in the lower-energy state and fluoresce green light; this green light component in combination with the NADH blue may well explain the turquoise color seen in the data. The blue (turquoise) fluorescent color is a signature of a metabolically active state. A metabolically active state may well be an indication of a healthy and freshly made spore.

Strong green fluorescence may indicate a metabolically resting state. A healthy spore that is resting or hibernating will contain a full complement of NADH and riboflavin molecules. These molecules will generally be in their lower-energy state. In its lower-energy NAD+ state, NADH does not fluoresce thus removing its blue light from the camera sensor image. In contrast, the riboflavin molecules will fluoresce strongly precisely because they are in their lower-energy state. In this manner a strong green image is a signature of intact biomolecules in a metabolically resting state. A metabolically resting state may well be an indication of a healthy spore that is "hibernating" while it waits for conditions supportive of mold growth. However, if the right conditions never arrive, the metabolically resting state may also an indication of a spore under siege by unfavorable conditions and that will eventually lead to its death.

Weak green fluorescence may indicate a decomposing state. A spore that is dying and decomposing will not only lack a blue NADH fluorescence signature, but will have an increasingly dim green fluorescence signatures as more and more (lower-energy) riboflavin molecules decompose.

When flavins fluoresce in response to UV light illumination, they emit light at a wavelength of about 520 nm (green). When NADH fluoresces in response to UV light illumination, it emits light at a wavelength of about 460 nm (blue). Depending on the properties of the optical image sensor, fluorescent light at 520 nm or 460 nm will produce distinctive RGB color ratios. For example, for an image sensor with color sensitivities as illustrated in FIG. 16, the ratio of intensities measured in red, green and blue sub-pixels will be approximate RED:GREEN:BLUE=1:10:4 for flavins and 0:1:8 for NADH. If measured RGB color ratios are approximately 1:10:4, the color ratios would support an interpretation that the observed fluorescence is due to flavins with little contribution from NADH. However if another color ratio is observed, then NADH and/or other biomolecules are contributing to the observed fluorescence image. Such an ability to probe the biochemistry with real-time optical image processing contributes to the ability of a biological particle monitor to probe the state as well as identity of biological particles under inspection.

Figure 25:
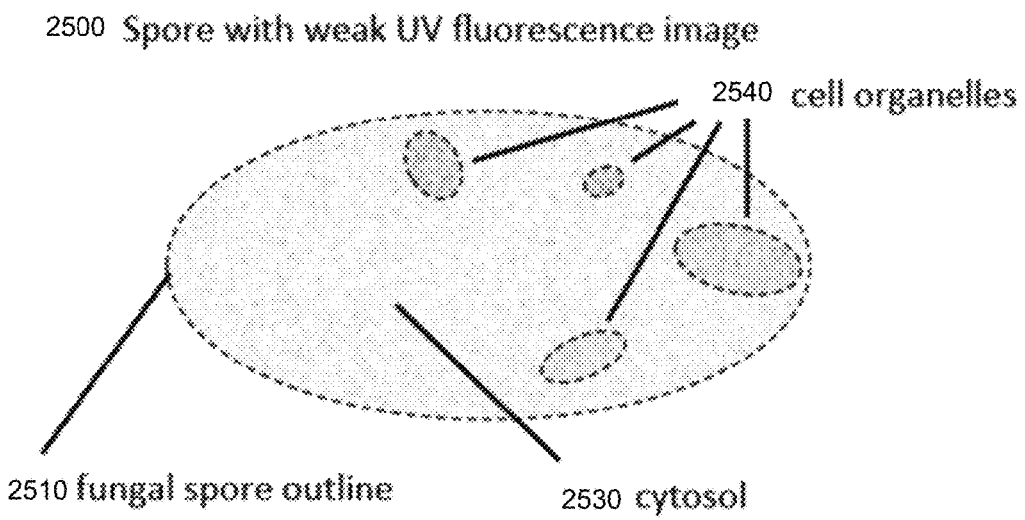
FIG. 25 is a schematic representation of a fungal spore with a weak fluorescence image using ultraviolet light illumination.

FIG. 25 schematically illustrates an image 2500 of the UV fluorescence of a fungal spore in which the intensity of fluorescence is weak compared to that illustrated in FIG. 24A. Such an image would indicate a lower density of fluorescing biomolecules in cytosol 2530 within fungal spore outline 2510 relative to cytosol 2430 as well as a lower density of fluorescing biomolecules in cell organelles 2540 relative to cell organelles 2440. If the illumination is 325 nm UV and the fluorescing biomolecule is NADH, then an image such as that illustrated in FIG. 25 would indicate a relatively low density of NADH and hence a relatively low energy production within the cell, that is a low level of respiration.

Figure 26:
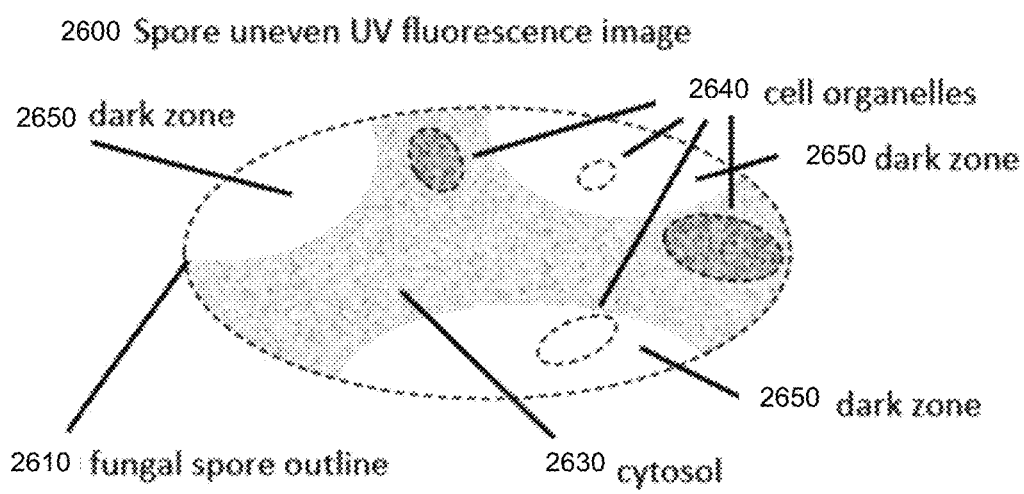
FIG. 26 is a schematic representation of a fungal spore with an uneven fluorescence image using ultraviolet light illumination.

Schematically illustrated image 2600 of FIG. 26 is similar to FIG. 24A except for the presence of dark zones 2650 within the fungal spore outline 2610 where little or no fluorescence occurs. (For purposes of illustration, FIGS. 23 through 27 are shown as negative images in the sense that the dark shading in the figures indicate an increase UV fluorescence and the white or absence of shading indicates no UV fluorescence.) In this case, under UV illumination, some of the cytosol 2630, and perhaps some cell organelles 2640, goes dark. Such an image would suggest that certain local portions of the spore are ailing.

While not explicitly shown in a figure, it is also of interest to observe when the effects illustrated in FIGS. 25 and 26 occur at the same time. That is, when there are not only darkened local regions of reduced UV fluorescence, but also an overall reduction in UV fluorescence intensity in the remaining regions of the spore.

Figure 27:
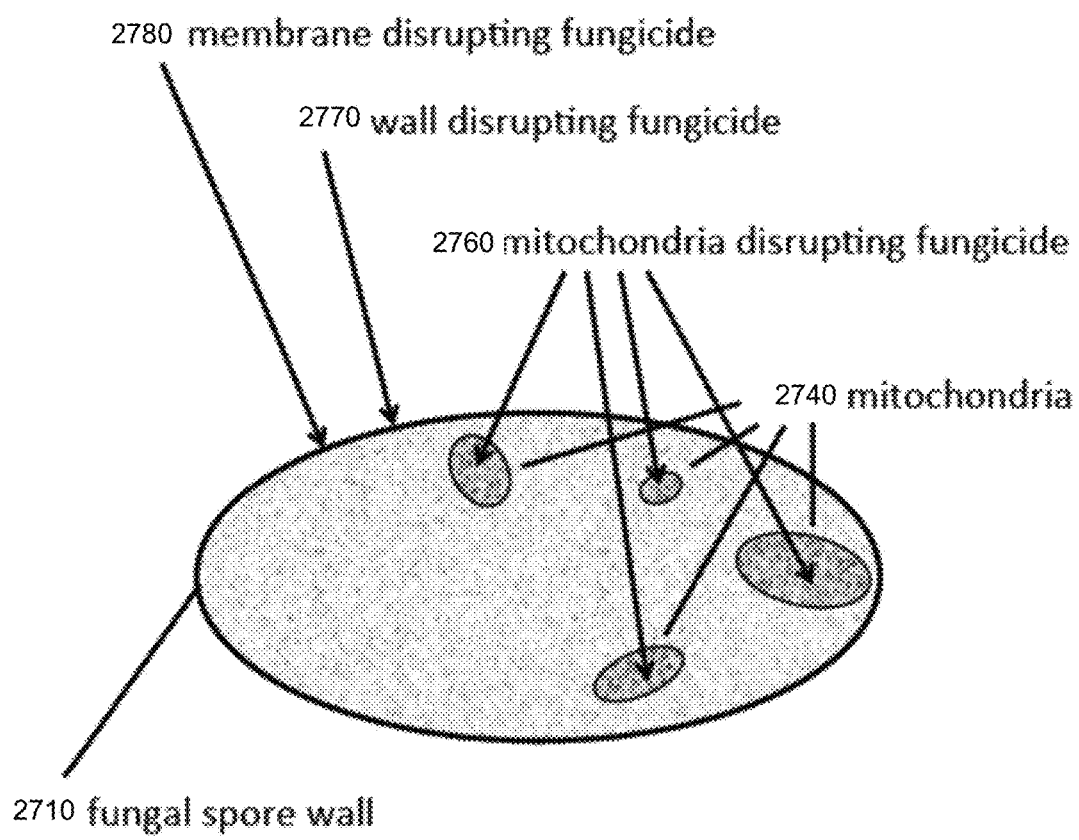
FIG. 27 illustrates mode of action of representative fungicides.

FIG. 27 illustrates some of the modes of action of fungicides. Mitochondria disrupting fungicides 2760, such as QoI, cyazofamid, boscalid and flutolanil interfere with the function of mitochondria 2740. A fungal spore damaged by such a mitochondria-disrupting fungicide may well have low levels of flavins and NADH such as illustrated in FIG. 25.

Cell wall disrupting fungicides 2770, such as polyoxin D, damage the cell wall 2710. Membrane disrupting fungicides 2780, such as DMI, dicarboximides, fludioximides, PCNB, chloroneb and propamocarb, damage cell membranes such as that immediately inside of the cell wall. A fungal spore damaged by either a wall disrupting fungicide or a membrane disrupting fungicides may suffer local damage where there is a breach in the cell wall or membrane. This may result in UV fluorescence images such as represented by FIG. 26. Analysis of visible light images (to determine the location of the fungal spore outline) and at least one UV-excited fluorescence image provides information on the state of a fungal spore, such as whether it remains healthy and virulent or whether it is injured, for example, by a fungicide.

As discussed above in connection with curve 1962 of FIG. 19, an ultraviolet illumination source with a wavelength somewhat shorter than 365 nm, such as 280 nm, will excite fluorescence of tryptophan and any other fluorescent amino acids within proteins. In other words, the amino acid tryptophan is excited by 280 nm UV light. There can be even shorter wavelengths that may excite other amino acids. Subtracting out the 365 nm fluorescence image, the 280 nm excited fluorescence image will provide image on the distribution of proteins within a fungal spore. Again this may well be used not only to aid biological particle identification, but also determination of the state of the biological particle. Similarly, even shorter UV wavelengths may be used to fluorescently excite even large sets of biomolecules, providing further information regarding both the identity and state of biological particles of interest.

Once a particle-monitoring device has captured visible-light and UV fluorescence images, a number of options exist for extracting particle state information from the image data. In an embodiment, explicit mathematical algorithms based on scientific considerations may be provided based on quantitative measures of fluorescence intensity (e.g., FIG. 25 versus FIG. 24A) and fluorescence non-uniformity (e.g., FIG. 26 versus FIG. 24A). For example, a threshold of total intensity may be defined below which a fungal spore is considered to be in an unhealthy state. Alternatively, machine-learning algorithms, such as often used with deep neural networks in the field of Artificial Intelligence (AI), may be used instead of, or in addition to, explicit scientifically based mathematical algorithms.

In either case, there is great value in creating a learning set of data. A learning set of data may include, for example, visible-light and UV fluorescence images of a number of healthy and virulent fungal spores, a number of fungal spores treated with a fungicide whose mode of action is to disrupt mitochondria (see item 2760 of FIG. 27), a number of fungal spores treated with a fungicide whose mode of action is to disrupt cell walls (see item 2770 of FIG. 27), as well as a number of fungal spores treated with a fungicide whose mode of action is to disrupt cell membranes (see item 2780 of FIG. 27). Once provided with a sufficiently informative learning set of images, systems and techniques may be applied to develop algorithms that distinguish between different states of biological particles.

The ability to develop effective algorithms that distinguish between different states of biological particles is further enhanced by the use of a tape medium such as illustrated in FIGS. 8, 9 and 10. Having a physical archive of captured biological particles such as fungal spores, particles of interest may be further studied off-line in a laboratory. For example, fungal spores may be removed from the tape medium and placed in an appropriate nutrient and then incubated under appropriate temperature and humidity conditions. If the spores grow into fungal colonies, then one has the gold-standard of proof that the collected fungal spores were virulent. If algorithms processing images predicted otherwise, then effort can be directed to fine tuning algorithms accordingly. If fungal colonies do not form, that would be consistent with a prediction from imaging processing algorithms that inspected fungal spores were not virulent.

However care must be given to the possibility that spore virulence was lost during storage in the tape medium. The tape medium may be stored in controlled temperature and humidity conditions in order to preserve spore vitality. In addition to attempted growth of fungal colonies, laboratory tests of fungal spores may include a number of bio-assay tests. In general, the option to supplement real-time optical image process with laboratory study of archived physical samples of particles provides an import technique to test and improve the reliability of the results of optical image processing.

Referring back now to FIG. 22, in a step 2255, the spore monitor calculates a degree of confidence in the state assessment. If the degree of confidence is above a threshold degree (e.g., state assessment is satisfactory), the spore monitor transmits and logs the state result (step 2260). Alternatively, if the degree of confidence is below the threshold degree (e.g., state assessment is not satisfactory), the spore monitor requests, obtains, and analyzes context information (step 2265). In a step 2270, the spore monitor again calculates a degree of confidence in the state assessment. If the degree of confidence is above the threshold (e.g., state assessment is satisfactory), the spore monitor transmits and logs the state result (step 2260). If the degree of confidence is below the threshold (e.g., state assessment is not satisfactory), the spore monitor issues a request for review by a human technician (step 2275).

It should be appreciated that any number of images may be captured and the images may be captured in any order. For example, the UV illuminated image may be captured before the visible light illuminated image. That is, the visible light illuminated image may be captured after the UV illuminated image. In some embodiments, only UV illuminated images are captured. That is, one can imagine situations in which no visible light image is captured. For example, if a protein fluorescence image turns out to provide a better outline of the spore than the visible light image.

Figure 28A:
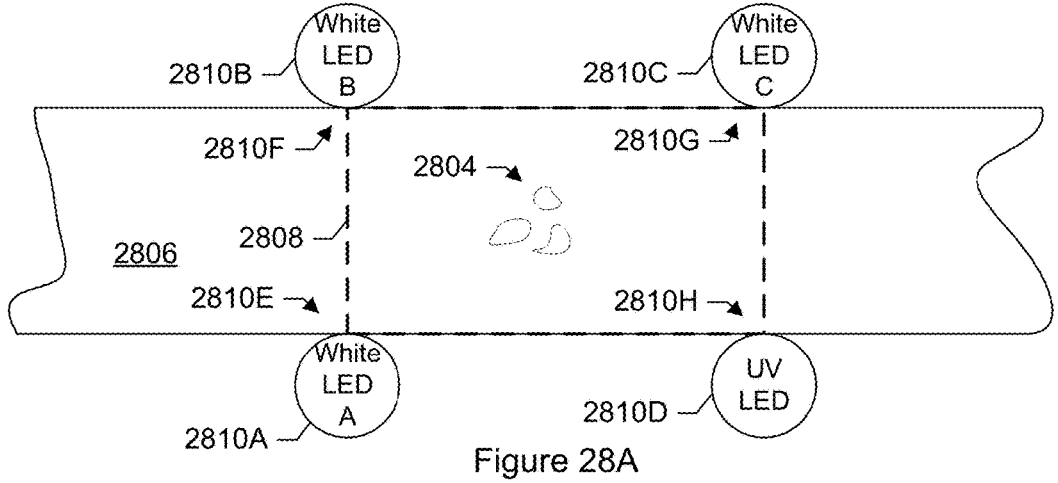
FIG. 28A shows an illumination system of a particle monitor according to another specific embodiment.

FIG. 28A shows a block diagram of a top view of a lighting or illumination arrangement of a particle monitor device according to another specific embodiment. As shown in the example of FIG. 28A, particles 2804 trapped on a portion of tape 2806 have been positioned within a field of view 2808 of a camera sensor. The field of view is shown in the figure as a broken line. The particles may include fungal spores.

The illumination system of this monitoring device includes a first white light source or structure 2810A, a second white light source or structure 2810B, a third white light source or structure 2810C, and an ultraviolet light source or structure 2810D. In an embodiment, the light sources include light emitting diodes (LEDs) or clusters of LEDs. The light sources are arranged about or around the field of view.

The light sources have illumination directions corresponding to the corners of the field of view. More specifically, the first white light source is positioned so that its light arrives in the field of view from a direction corresponding to a first corner 2810E of the field of view. The distance from the white light LED 2810A to first corner 2810E is larger than shown in FIG. 28A. The sketch is not to scale in order to avoid drawing items too small to be clearly seen (like is generally done in for drawings of the solar system). The second white light source is positioned so that its light arrives in the field of view from a direction corresponding to a second corner 2810F of the field of view. The third white light source is positioned so that its light arrives in the field of view from a direction corresponding to a third corner 2810G of the field of view. The UV light source is positioned so that its light arrives in the field of view from a direction corresponding to a fourth corner 2810H of the field of view. The dimensions of the field of view, such as the distance from first corner 2810E and second corner 2810F may be approximately one millimeter. The distance of the light sources 2810A, 2810B, 2810C and 2810D from the field of view 2808 may be one or more centimeters.

The positioning of the light sources allow for illuminating the trapped particles from different angles. In a specific embodiment, the light sources are distributed and spaced equally about the field of view. The light sources may form corners of a square. A first distance is between first and second white light sources. A second distance is between second and third white light sources. A third distance is between the third white light source and the UV light source. A fourth distance is between the UV light source and the first white light source. In this specific embodiment, the distances are equal to each other. In another specific embodiment, at least one distance is different from another distance. For example, the light sources may form corners of a rectangle or other polygon. It should be appreciated that the light sources shown in FIG. 28A and elsewhere can represent openings through which light is output towards the field of view. For example, an opening may include an end of an optical fiber. An opposite end of the optical fiber may be connected to the actual emitter (e.g., LED) that may be located elsewhere in the particle monitor device and remote from the field of view. The optical fiber guides or transmits light from the actual emitter to the opening near the field of view.

In an embodiment, a technique for identifying a spore uses bursts or flashes of white light in combination with illuminating the trapped particles with UV light. Before the health of a fungal spore can be determined, an identification of the type of spore it is may be made. One of the key parameters employed in identifying these is the morphology of the particle among others.

Fungal spores are in many cases transparent or semi-transparent under visible light, which presents a challenge in obtaining morphology using white light, as most of it will go through it. These are also pleomorphic where their size and shape can vary over time, that is, spores are like frogs that also change shape during their lifecycle (think tadpole versus adult frog). Desiccation or moisture absorption may also cause spore shape changes. Typical techniques used today employ light microscope, SEM, AFM microscopy, among others; and are time consuming, requiring sample preparation and trained users of the device and the technique employed.

It can be cumbersome and time consuming when viewing a transparent fungal spore such as *Erysiphe Necator* (aka. Powdery mildew) or *Botrytis* (aka. Gray mold) for a user to apply a staining dye to enhance the outline of the spore in order to determine the shape (morphology) of the spore using a camera or estimating it against a size grid. In another example, when using a fluorescent microscope it is necessary to apply fluorescent dyes to the subject and further manipulate the emitted light through beam splitters and filters. Typically light is polarized and, or collimated. AFM techniques may employ force, beam deflection, contact, phase measurements, electrical fields, magnetic fields, and others to map out the shape of a particle.

In order to obtain the shape of a spore or simultaneously scan a group of spores without doing any sample preparation, applicant has discovered that while exciting the spore(s) with a UVLED (non-polarized) and applying a burst of white light from a non-polarized light source at a different angle from the UVLED excitation angle, near the end of the integration time results in a single image that contains fluorescent data as well as a profile of the full area (shape) of the particle.

Applicant has discovered that due to the pleomorphic nature of the fungal spores and that they do not always come in front of the camera lens in the same direction and their health state, it is desirable to input white light in smaller bursts around the perimeter of the particle.

Figure 28B:
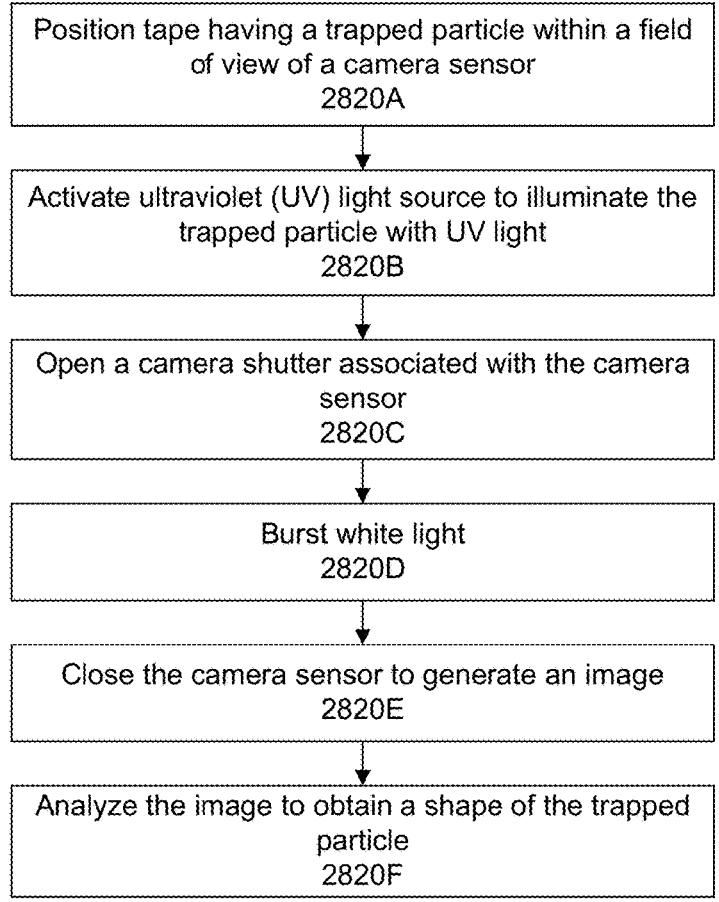
FIG. 28B shows an overall flow for combining UV and white light bursting when imaging a trapped particle according to a specific embodiment.

FIG. 28B shows an overall flow of the white light burst or flash technique according to a specific embodiment. In a step 2820A, a portion of tape having a trapped particle is positioned within a field of view of a camera sensor of the particle monitor. In a step 2820B, a UV light source (e.g., UV LED) is activated to illuminate the trapped particle with UV light. The activation of the UV light source is accompanied by the opening of a camera shutter associated with the camera sensor (step 2820C). Optionally, shutter opening of step 2820C may occur simultaneously with, or even before, the UV light activation of step 2820B. In a step 2820D, one or more bursts of white light is directed towards the trapped particles within the field of view. In a step 2820E, the camera sensor is closed to generate an image. In a step 2820F, the image is analyzed to obtain a shape of the trapped particle.

Figure 28C:
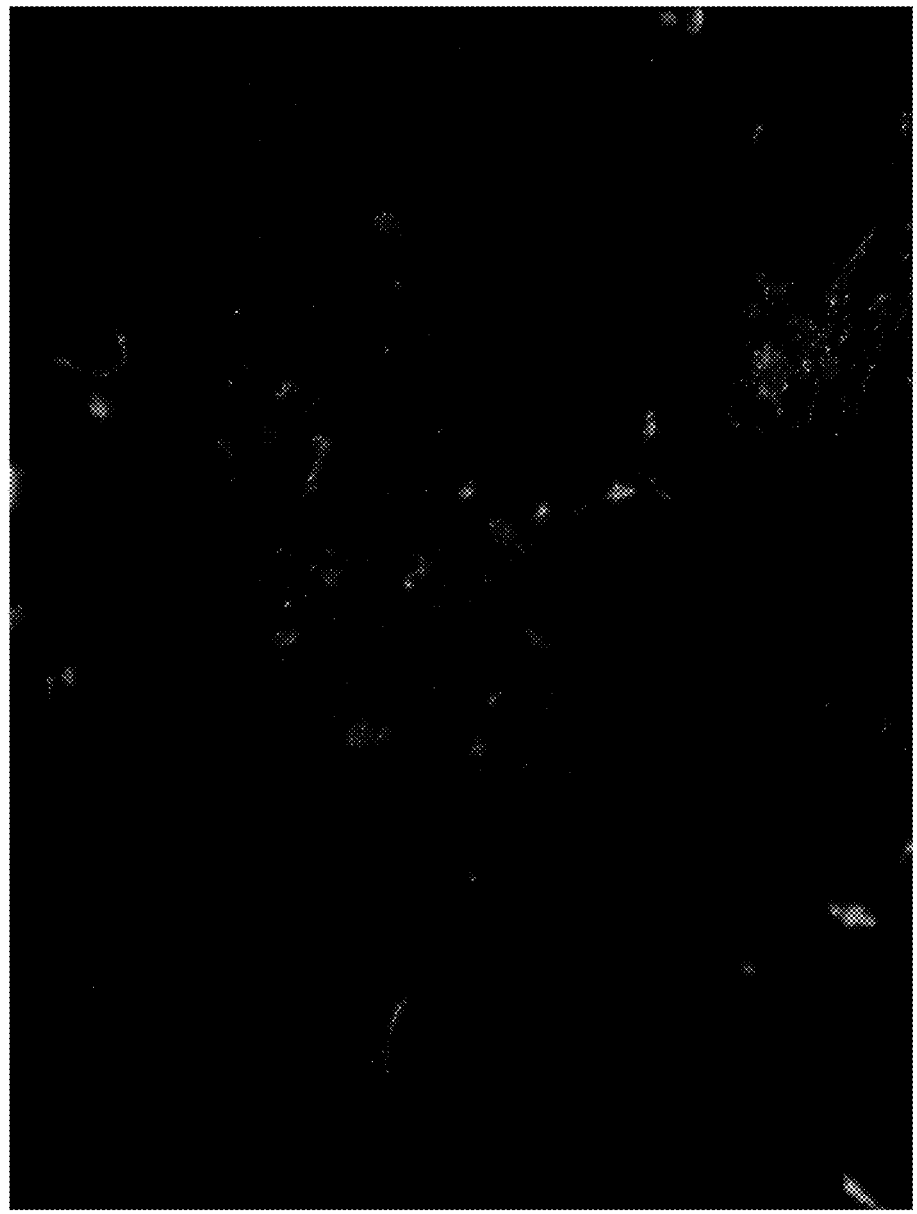
FIG. 28C shows an image of a fungal as illuminated under white light.
Figure 28D:
FIG. 28D shows an image of the fungal as illuminated under UV light.
Figure 28E:
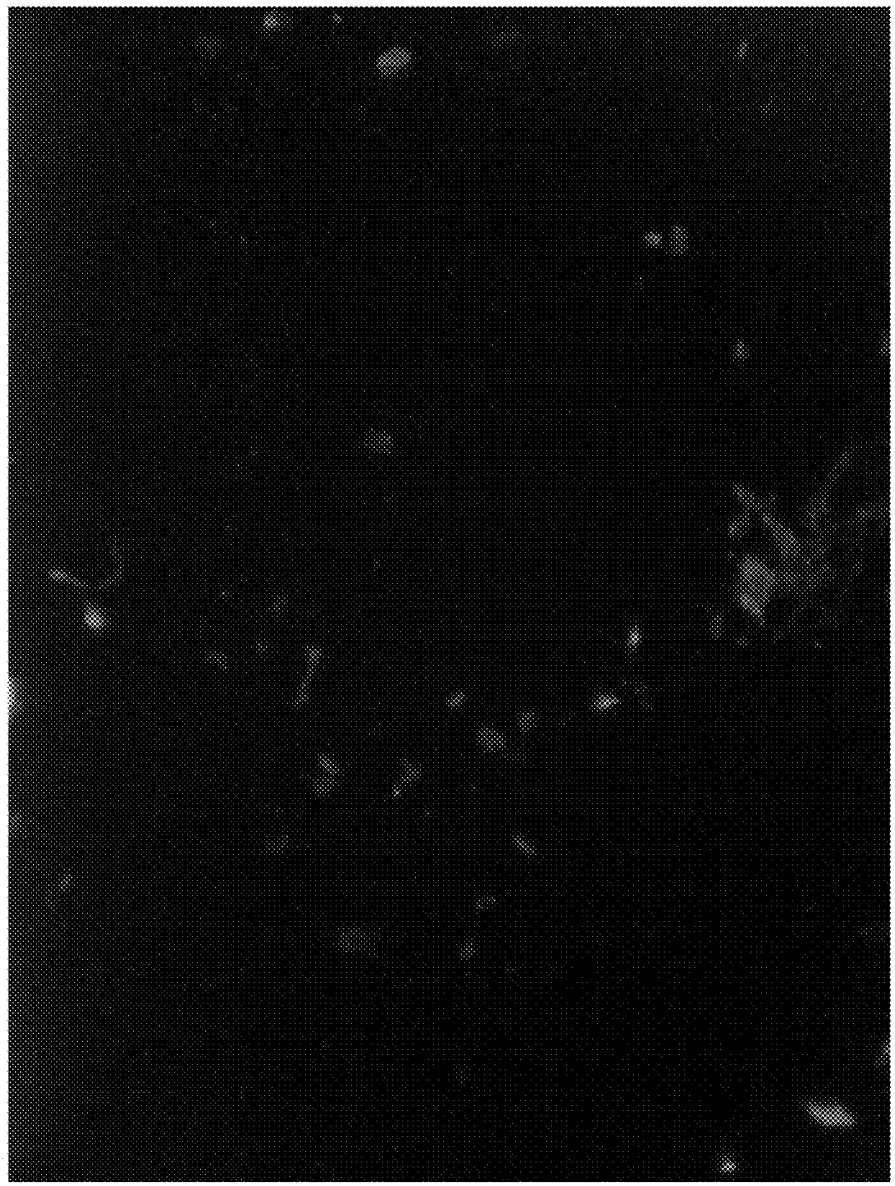
FIG. 28E shows an image of the fungal as illuminated under UV light and a burst of white light.

FIGS. 28C-28E show a comparison of various image techniques on fungal powdery mildew. FIG. 28C shows an image of the fungal as illuminated under white light. FIG. 28D shows an image of the fungal as illuminated under UV light. FIG. 28E shows an image of the fungal as illuminated under UV light and a burst of white light.

More particularly, in this experiment, powdery mildew spores along with conidia and some hyphae were imaged using white light (FIG. 28C), a 340 nm UV light (FIG. 28D), and the UV plus white light burst (FIG. 28E). A duration of the white light burst was 0.1 seconds. Based on the imaging results, UV plus the white light burst was shown to provide better definition of total particle area and shape (used to extract important classification parameters) along with UV fluorescence used to determine the health state of the fungal spore. In this experiment, the white light image was collected much earlier than the UV and UV plus white burst images and the particles in the field of view had shifted to the left by approximately 0.25 mm.

Figure 28F:
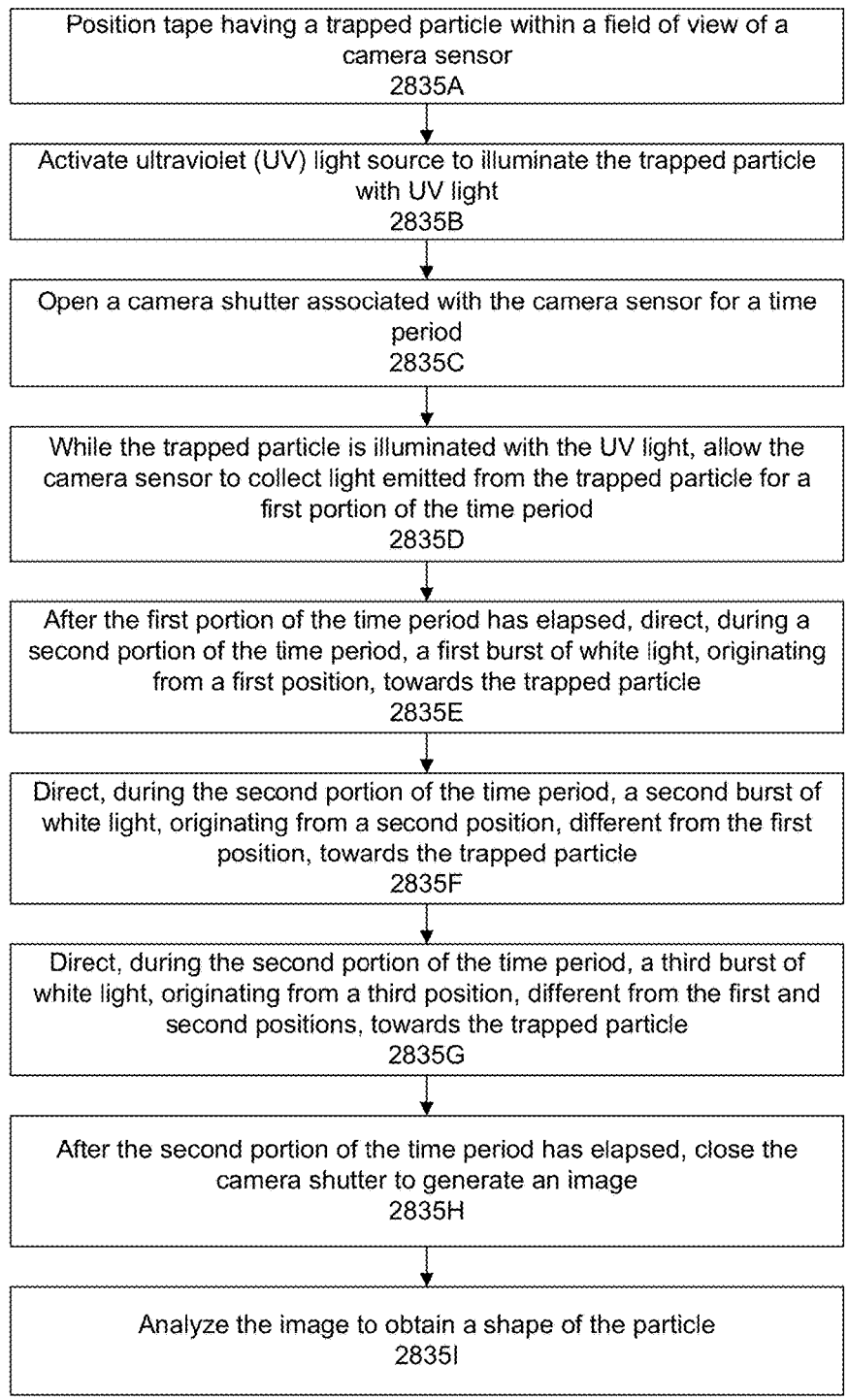
FIG. 28F shows further detail of a flow for combining UV and white light bursting when imaging a trapped particle according to another specific embodiment.

FIG. 28F shows further detail of a flow for the white light burst or flash technique according to a specific embodiment. In a step 2835A, a portion of a tape having a trapped particle is positioned within a field of view of a camera sensor. In a step 2835B, a UV light source (e.g., UV LED) is activated to illuminate the trapped particle with UV light. In a step 2835C, a camera shutter associated with the camera sensor is opened for a time period. The time period may be referred to as an exposure time period.

In a step 2835D, while the trapped particle is illuminated with the UV light, the camera sensor is allowed to collect light emitted from the trapped particle during a first portion of the time period.

In a step 2835E, after the first portion of the time period has elapsed, past, or expired, a first burst of white light, originating from a first position, is directed during a second portion of the time period after the first portion towards the trapped particle.

In a step 2835F, after the first burst, a second burst of white light is directed during the second portion of the time period towards the trapped particle. The second burst of white light originates from a second position, different from the first position.

In a step 2835G, after the first and second bursts, a third burst of white light is directed during the second portion of the time period towards the trapped particle. The third burst of white light originates from a third position, different from the first and second positions.

In a step 2835H, after the second portion of the time period has elapsed, the camera shutter is closed to generate an image.

In a step 2835I, the image is analyzed to obtain a shape of the particle.

In a specific embodiment, a duration of the time period is about 15 seconds, a duration of the first portion of the time period is about 14 seconds, and a duration of the second portion of the time period is about 1 second.

Figure 28G:
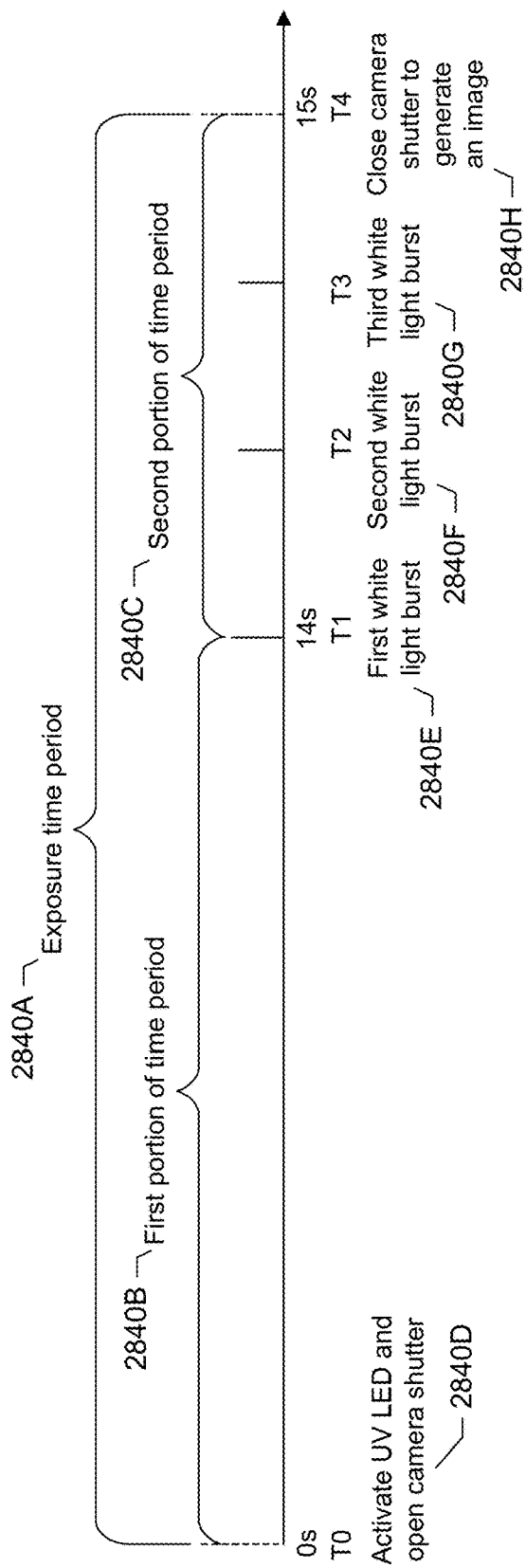
FIG. 28G shows a timeline of events for combining UV and white light bursting when imaging a trapped particle according to a specific embodiment.

FIG. 28G shows a timeline and sequence of events of the white light burst technique according to a specific embodiment. As shown in the example of FIG. 28G, there is a time period or exposure time period 2840A, first portion 2840B of the time period, and second portion 2840C of the time period. The second portion is immediately after the first portion. In other words, the first portion is immediately before the second portion. In this specific embodiment, durations of the first and second portions are different. In this specific embodiment, the duration of the first portion is greater than the duration of the second portion. In other words, the duration of the second portion is less than the duration of the first portion.

At T0, initial events 2840D of the first portion of the time period includes activating a UV LED and opening the camera shutter. The first portion of the time period ends at T1 at which point the second portion of the time period begins. The ending of the first portion of the time period (or the beginning of the second portion of the time period) is accompanied by a first burst of white light 2840E. During the second portion of the time period, there is a second burst of white light 2840F at T2 that follows the first burst of white light. In other words, the second burst is after the first burst. The first burst is before the second burst.

During the second portion of the time period, there is a third burst of white light 2840G at T3 that follows the second burst of white light. In other words, the third burst is after the first and second bursts. The first and second bursts are before the third burst. The second portion of the time period ends at T4 and is accompanied by a closing of the camera shutter to generate an image 2840H.

In a specific embodiment, the UV light and white light bursts originate from different positions about the field of view of the camera sensor. For example, as shown in the block diagram of FIG. 28A, the light sources or light openings are arranged to illuminate from different directions about or around the field of view. This allows various light to be directed towards the trapped particles at various different angles. In particular, the first white light source is closer to the first corner of the field of view than the second, third, and fourth corners. The second white light source is closer to the second corner of the field of view than the first, third, or fourth corners. The third white light source is closer to the third corner of the field of view than the first, second, and fourth corners. The UV light source is closer to the fourth corner of the field of view than the first, second, or third corners.

In a specific embodiment, a duration of the time period is 15 seconds, a duration of the first portion of the time period is 14 seconds, a duration of the second portion of the time period is 1 second, a duration of the first burst of white light is 0.033 seconds, a duration of the second burst of white light is 0.033 seconds, and a duration of the third burst of white light is 0.033 seconds. In a specific embodiment, a method includes first turning on the UVLED from the bottom right of the field of view and opening the camera shutter to collect emitted light for 15 seconds. At 14 seconds of completion, turning on a white LED for 0.033 secs from the bottom left of the field of view, then turning it off while turning on a second white LED coming from the top left of the field of view for 0.033 secs, then turning it off while turning on a third white LED in the top right of the field of view for a total of 0.033 secs. The shutter then closes at 15 secs and the camera generates a single image showing fluorescence of the particles with white light enhancing the fluorescent light within the particle and filling in the entire volume of a spore defined by its outline, perimeter, or boundary.

As shown in the timeline example of FIG. 28G, the white light burst is orders of magnitude smaller than the UV integration time. Applicant has discovered that a tenth of a second (0.1 secs) is plenty of white light over 15 secs of UV fluorescence, for at least for powdery mildew spores. Adding more white light integration time results in more image saturation, which causes finer spore details to be lost. And having too little does not add enough detail to the spore shape. Other spores may benefit from a different setup.

In a specific embodiment, the white light burst occurs right before the end of the integration time. In this specific embodiment, applicant has discovered that capturing these at beginning or middle of integration time does not provide enough detail when UV fluorescence continues to be captured after white light was acquired.

This could be done at more angles and directions than just three and it can be desirable to have these also alternate from different incident angles above the tape surface. In a specific embodiment, there are at least two white light sources and one UV light source at 120-degrees apart from each other.

FIGS. 28H-O show a series of intermediate sample images made of grape powdery mildew under various lighting conditions or modes using the lighting arrangement shown in FIG. 28A. These intermediate sample images help to illustrate the advantages and benefits of combining UV and white light bursts or flashes when imaging a trapped particle for identification and analysis.

Figure 28H:
FIG. 28H shows an image generated where UV light was coming from a bottom right hand corner of the field of view.
Figure 28I:
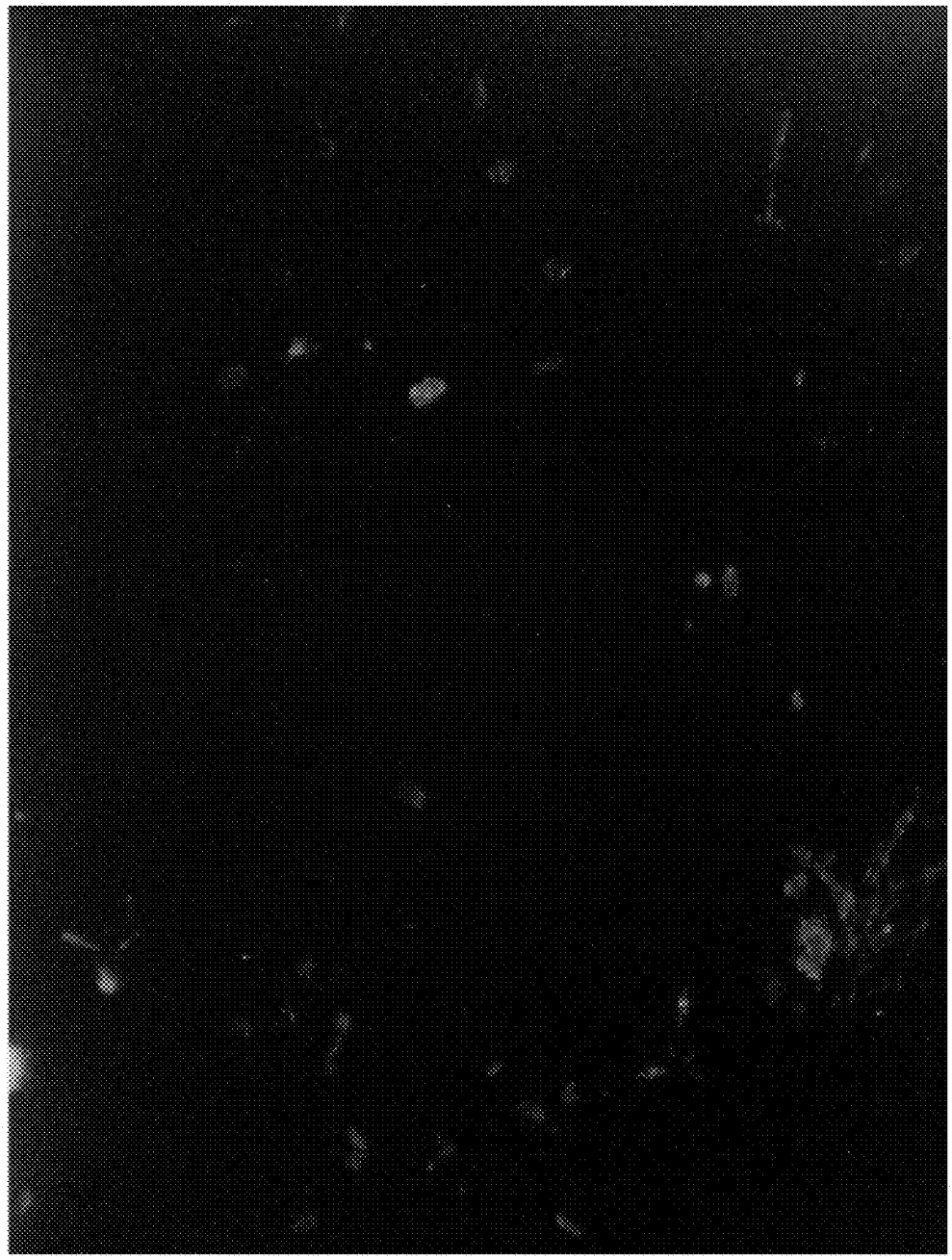
FIG. 28I shows an image generated where a direction of illumination was from a bottom left hand corner of the field of view.
Figure 28J:
FIG. 28J shows an image generated where a direction of illumination was from a top left hand corner of the field of view.
Figure 28K:
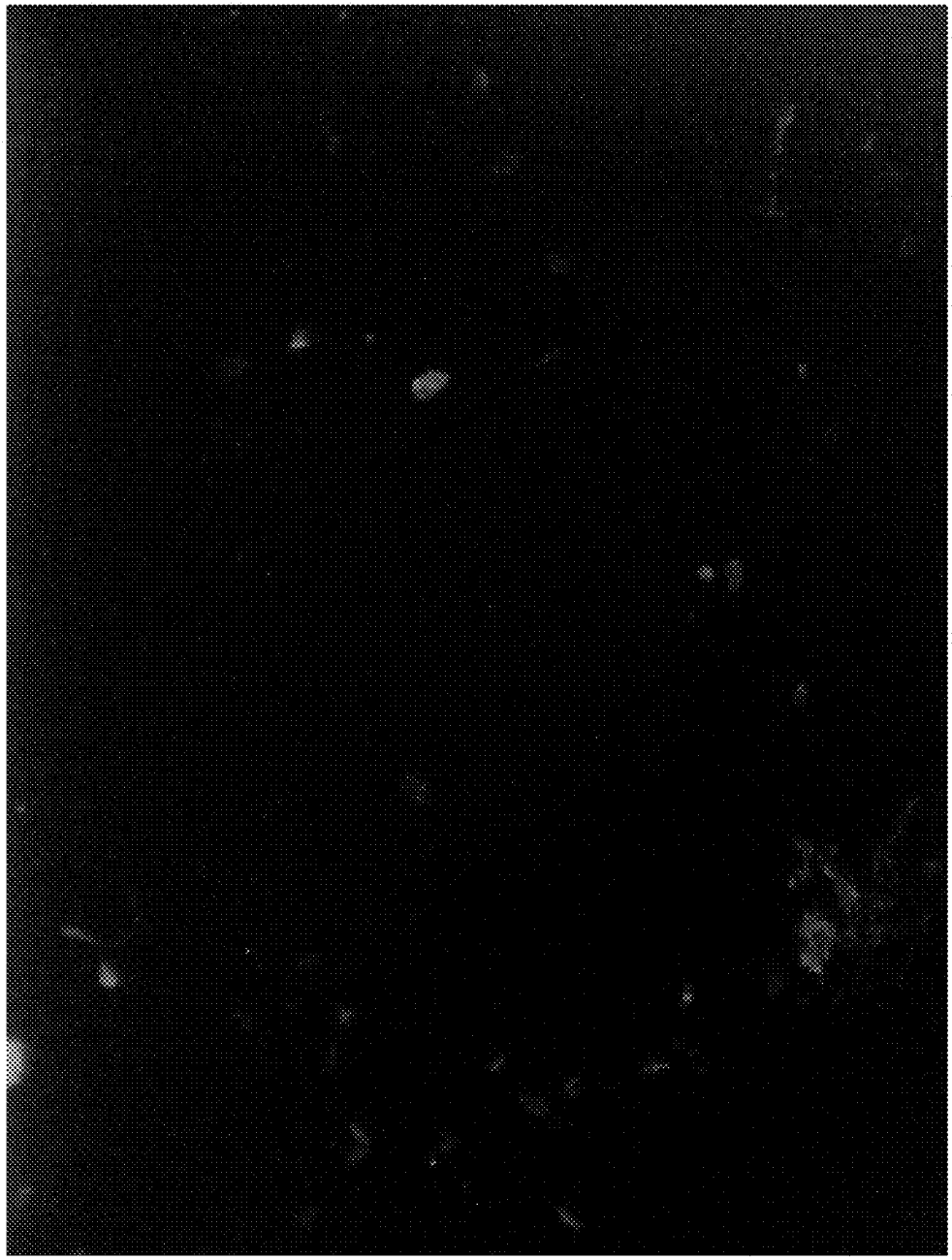
FIG. 28K shows an image generated where a direction of illumination was from a top right hand corner of the field of view.
Figure 28L:
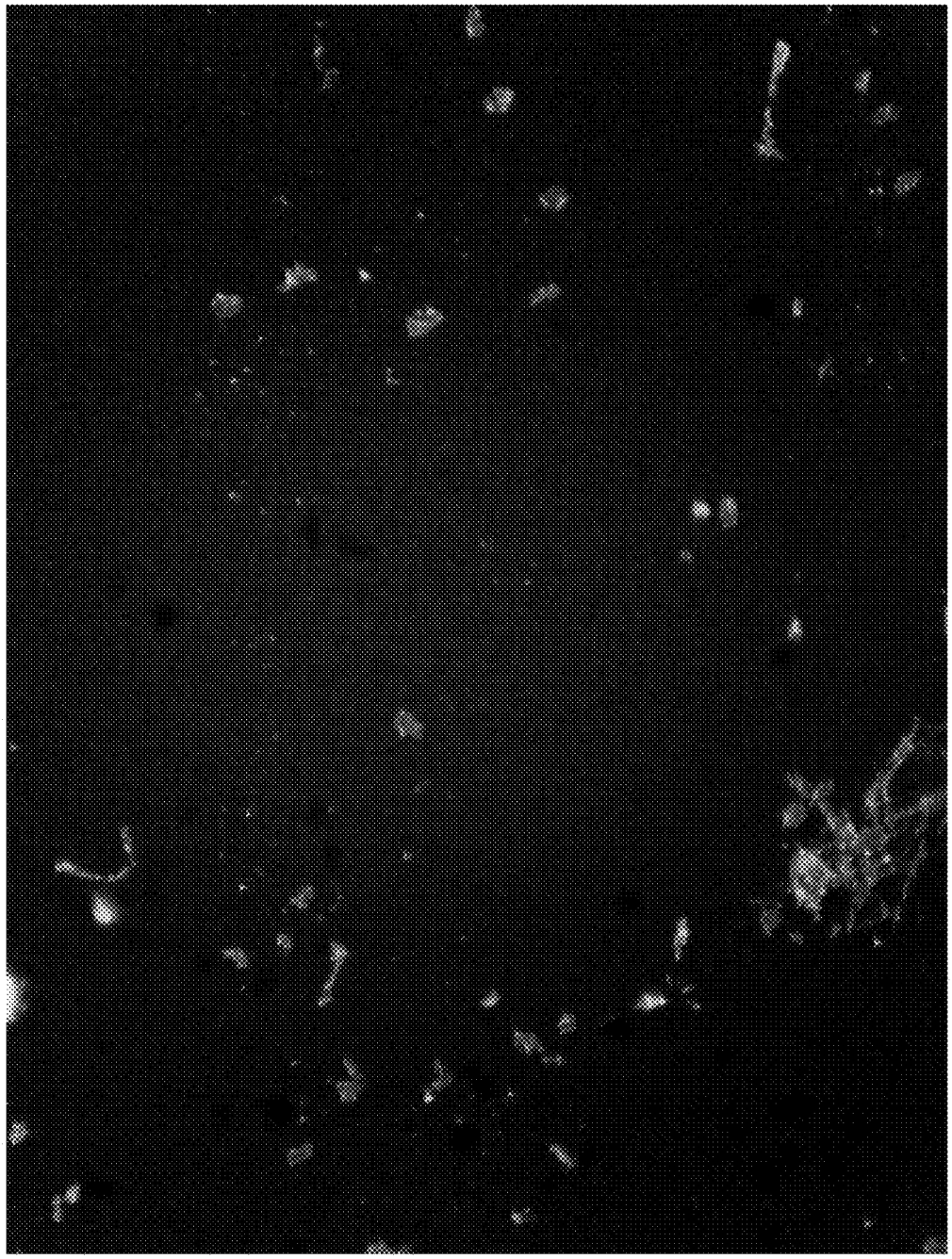
FIG. 28L shows an image generated where all three white LEDs were on simultaneously for 1 second.
Figure 28M:
FIG. 28M shows an image generated where illumination included a single white LED and no UV light was present.
Figure 28N:
FIG. 28N shows an image where the white light bursting or flashing occurred early during the exposure time period.
Figure 28O:
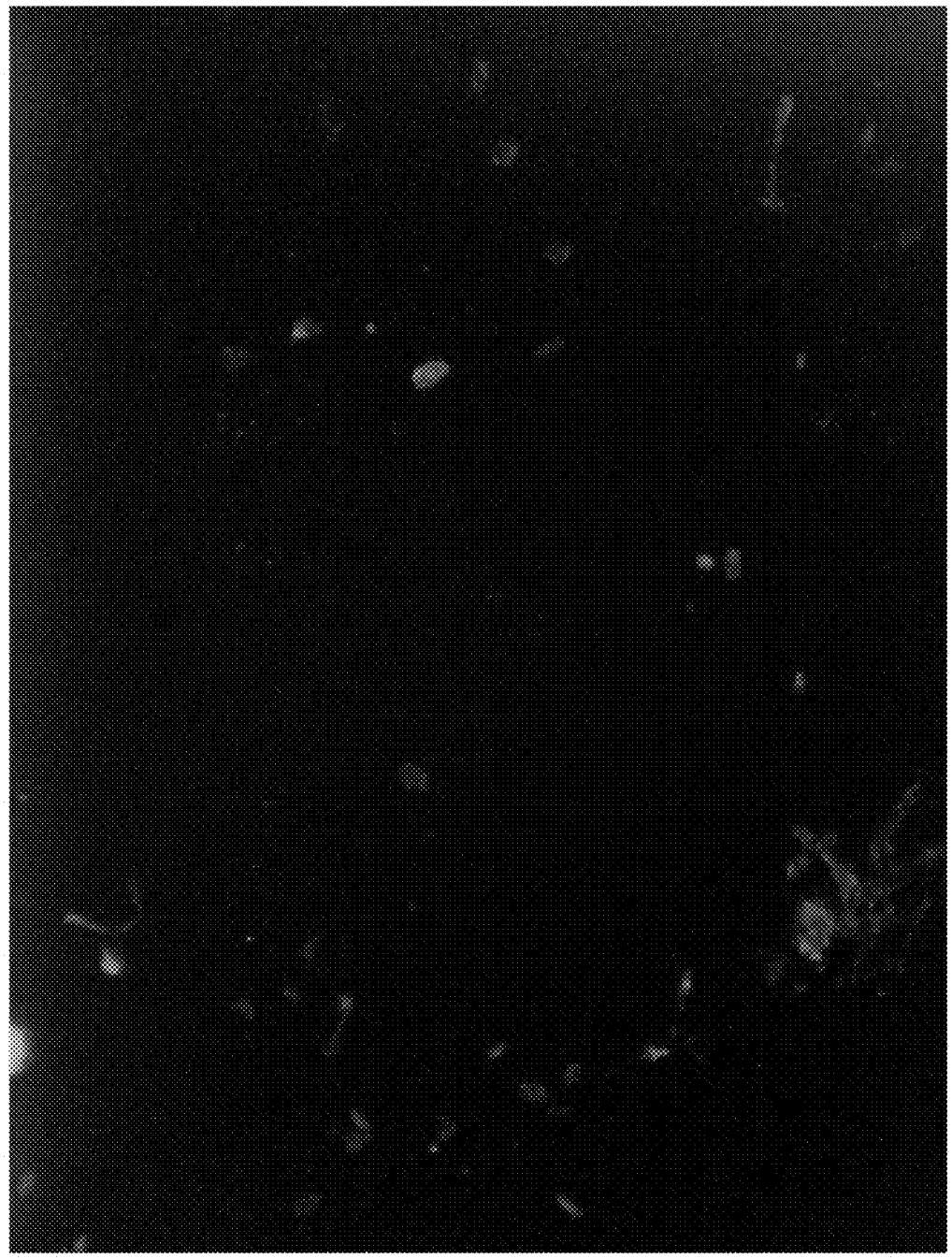
FIG. 28O shows an image where the white light bursting or flashing occurred late during the exposure time period.

More specifically, FIG. 28H shows an image generated while UV light is coming from bottom right of the field of view. FIG. 28I shows an image generated while a direction of illumination was from bottom left of the field of view. FIG. 28J shows an image generated while a direction of illumination was from top left of the field of view. FIG. 28K shows an image generated while a direction of illumination was from top right of the field of view. FIG. 28L shows an image generated where all three white LEDs were on simultaneously for 1 second. FIG. 28M shows an image generated where illumination included a single (white) LED and no UV light was present. FIG. 28N shows an image where the white light bursting or flashing occurred early during the exposure time period. FIG. 28O shows an image where the white light bursting or flashing occurred late during the exposure time period.

Figure 28P:
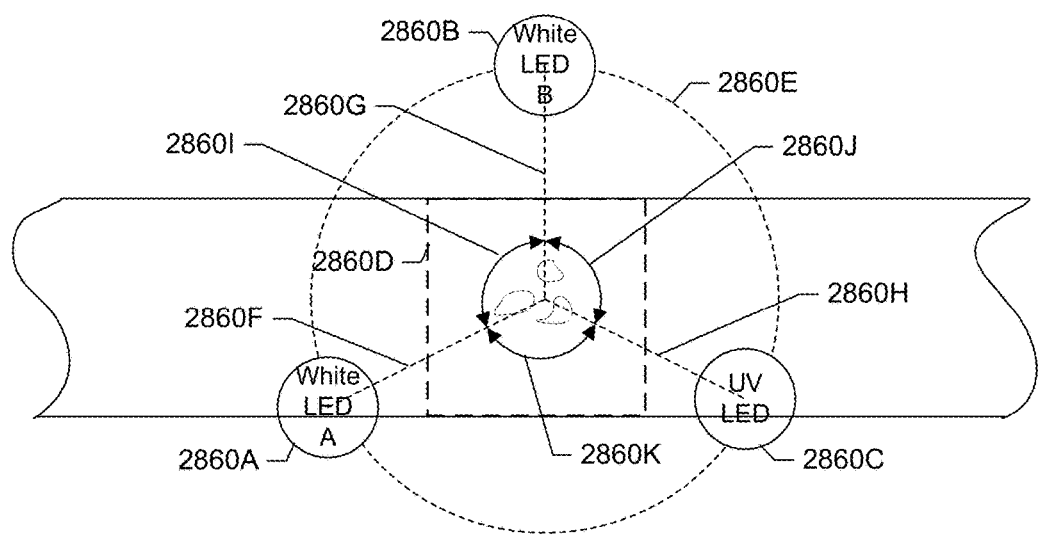
FIG. 28P shows a top view of an illumination system of a particle monitor according to another specific embodiment.

FIG. 28P shows a top view of a lighting or illumination arrangement of a particle monitor according to another specific embodiment. FIG. 28P is similar to FIG. 28A. In FIG. 28P, however, the illumination system includes two white light sources (a first white light source 2860A, a second white light source 2860B), and a UV light source 2860C. The light source direct, from different directions, light towards a field of view 2860D of a camera sensor. As shown in the example of FIG. 28P, the light sources are disposed about or around the field of view and are equally spaced from each other. In other words, in this specific embodiment, the light sources are positioned such that a circle 2860E passes through a center of each light source. A first line segment 2860F extends from a center of the circle to a center of the first white light source. A second line segment 2860G extends from the center of the circle to a center of the second white light source. A third line segment 2860H extends from the center of the circle to a center of the UV light source.

A first angle 2860I is between the first and second line segments. A second angle 2860J is between the second and third line segments. A third angle 2860K is between the third and first line segments. In a specific embodiment, the first, second, and third angles are the same. In a specific embodiment, each of the first, second, and third angles are 120 degrees.

In an embodiment, non-polarized light is used so that light scatters in random angles and reflects randomly. This can help against the ever changing topography of the spores throughout their life cycle. When young their outer shell may have a soft surface and be full of moisture which is more reflecting, but under stress like loss of moisture it will wrinkle and shrink in size having varying areas of the spore that will reflect more or less than others. In contrast, having light coming from all directions at once may fill in details that are not clearly visible from certain illumination angles.

Some light goes through the particle, some may get tunneled (or channeled) within the outer walls (the skin) of the spores, and some light will bounce in different directions inside the spore as it goes through mitochondria, lipids, and others where absorbed versus reflected light will vary. In some cases, illuminating from a single angle may not reveal the entire shape, but illuminating from multiple angles at different intervals reveals more finer details of the spores.

As the spores age, certain structures will be weaker than others and will take a lot more energy to emit light.

In some cases, a single or multi-angle white light image may not provide enough spore shape details. The amount of reflected white light across the spore may correspond to its health (age as well) as seen through the UV fluorescence. Newly released spores have very bright turquoise fluorescence and a very bright reflected white light across the entire shape of the spore. However, after days later the turquoise fluorescence decreases or becomes green and applicant has discovered that when collecting a single white light image of the same previous spore now shows dimmer, less reflecting, or dark areas within the spore. This may indicate that one cannot necessarily rely on a white light image to extract shape because it will also change with the spore's health.

Using UV fluorescence with the short burst of white light integrated from different angles and across different directions across the spores' camera field of view can provide an accurate rendition of the spores' volume. And instead, there can be a single fluorescent and single white light against the combined image to detect the spore state.

Below are some benefits of this collection scheme:

1) A single image contains accurate spore shape, which is one of many parameters used in identification. Contains fluorescent information across its shape to determine spore state 2) Additional information about spore texture can be extracted to further identify a particle within its state.

3) A new set of color parameters can be extracted and used in spore identification at various stages of the life of the species.

In various specific embodiments, a new method and technique is provided for extracting shape information of transparent and semi-transparent particles including fungal spores and other organisms regardless of the stage in their lifecycle. In a specific embodiment, a method is provided of simultaneously generating shape, texture, and topography data of a transparent spore. In another specific embodiment, there is a system for simultaneous discrimination of random particles and their classification.

FIG. 28P shows a symmetrical arrangement of the light sources. In various other specific embodiments, there may be a non-symmetrical or asymmetrical arrangement of the light sources. For example, one or more of the first, second, or third angles may be different from another of the first, second, or third angles. In another specific embodiment, a light source may be in a plane different from a plane of another light source.

Figure 28Q:
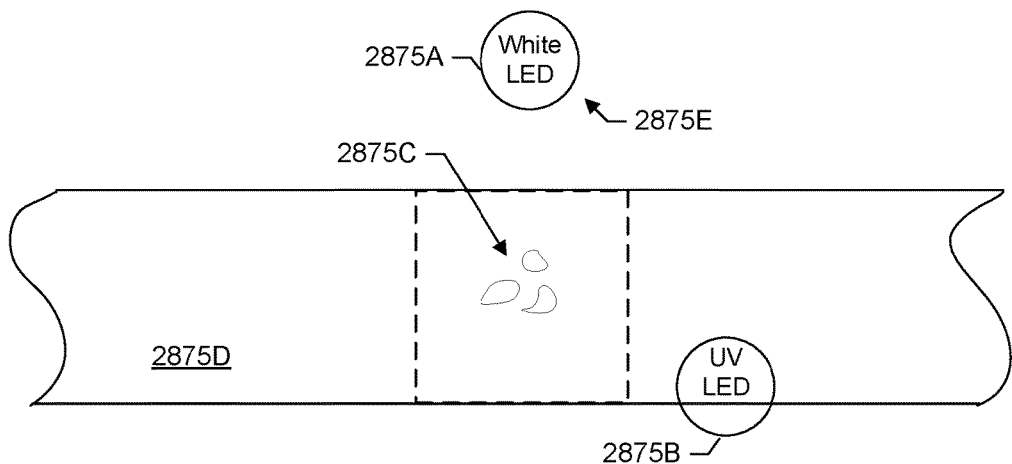
FIG. 28Q shows a top view of an illumination system of a particle monitor having a movable light source in a first position according to another specific embodiment.
Figure 28R:
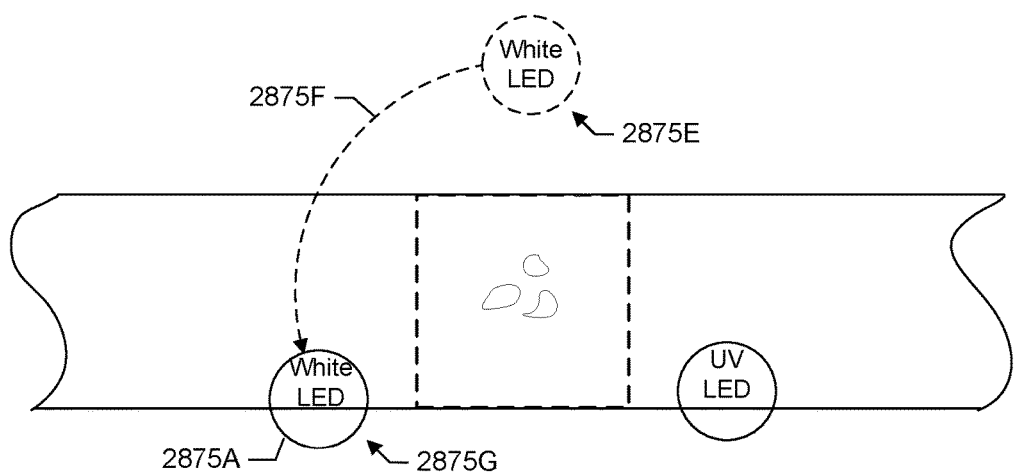
FIG. 28R shows a top view of an illumination system of a particle monitor having a movable light source in a second first position according to another specific embodiment.

FIG. 28P shows an example of light sources whose positions are fixed. FIGS. 28Q and 28R show top views of another lighting arrangement of a particle monitor device according to another specific embodiment. FIGS. 28Q and 28R are similar to FIG. 28P. In FIGS. 28Q and 28R, however, there is a single white light source whose position is moveable. More particularly, FIG. 28Q shows a lighting or illumination system that includes a white light source 2875A and a UV light source 2875B. In this specific embodiment, at least one of the light sources is moveable relative to particles 2875C trapped on a cartridge collection tape 2875D.

Specifically, FIG. 28Q shows the white light source in a first position 2875E. FIG. 28R shows the white source having moved 2875F from the first position to a second position 2875G, different from the first position. The light source (e.g., white light source) can be moved so that the particles can be illuminated from different angles and directions. In a specific embodiment, one or more light sources are rotatable about the field of view. A light source may rotate, translate, or both so as to illuminate particles within the field of view from different angles and directions.

In a specific embodiment, illumination of the particle with LEDs is from fixed angles about the tape where the spore is positioned under the camera. In another specific embodiment, a device may include only a single white light source and the light source can move about the spore and illuminate it from different directions and angles.

In a specific embodiment, at least three positions or angles—120 degrees apart are provided to aid in generating a contour profile of the spore. There can be a 'turret' holding a single white and UV LEDs that rotates around the camera's field of view illuminating and the camera collecting images from different illumination angles.

In another specific embodiment, there can be a stage holding the spore (the tape) can move from a known XY location to a known new XY location and illuminated again where both image locations are overlap using software to now reveal an enhanced contour profile of the particle, this could be done multiple times until a satisfactory profile has been obtained, which can be determined when a new XY location does not change the previous area profile of the particle (spore). In another specific embodiment, the lights may be fixed but the camera moves about to allow for images from different light angles.

As another example, a particle monitor device may include a multiplexer, computer controller and control circuit, light openings disposed in different positions, locations, or angles about a field of view of a camera sensor of the monitor, a white light emitter, and a UV light emitter. At least a subset of the light openings may be connected to an output of the multiplexer. Another subset of the light openings may be connected to the UV light emitter.

The multiplexer may be connected to the white light emitter. For example, first and second light openings may be connected via optical fiber to the output of the multiplexer. The white light emitter may be connected via optical fiber to the multiplexer. The first light opening may be positioned about the field of view to output light in a first direction or angle towards the field of view. The second light opening may be positioned about the field of view to output light in a second direction or angle, different from the first direction or angle, towards the field of view.

The computer controller and control circuit is interconnected with and controls the operation of the multiplexer, camera sensor, and emitters. The computer can use the multiplexer to control which of the first or second light openings to use to transmit light from the white light emitter to the field of view.

For example, a first burst of white light may be transmitted from the white light emitter through the multiplexer and out the first light opening towards the field of view. The first burst of white light will not be transmitted through the second light opening because the multiplexer can prevent the transmission. A second burst of white light may be transmitted from the same white light emitter through the multiplexer and out the second light opening towards the field of view. The second burst of white light will not be transmitted through the first light opening because the multiplexer can prevent the transmission.

Thus, a single light emitter can be used to output light in two or more different directions or angles at different times. This can help to reduce the cost of the particle monitor. As one of skill in the art will recognize, a UV light emitter can similarly be connected to a multiplexer to provide different UV illumination lighting at different times, directions, or both. Alternatively, the multiplexer may be configured to provide illumination (e.g., white light, UV light, or both) from different angles or directions simultaneously or concurrently.

Current prior art devices include some sort of impactor or undesired particle purge prior to analyzing a set of particles of interest. In a specific embodiment, a particle monitor device is provided that is not limited to any particle size or shape, rather the flow of air is unobstructed, unrestricted, and unlimited in the particles that get analyzed, and analysis is only limited by camera resolution. In a specific embodiment, light illumination comes from at least two directions to generate the contour profile of the particle (spore). In a specific embodiment, white light is added as a burst to UV light in generating the contour profile of the particle (spore). In a specific embodiment, the spores are illuminated against a dark (black) background.

Conventional fluorescence spectroscopy takes advantage of the high spectral resolution of spectrometers such as those based on diffraction gratings. Such spectrometers can be very expensive. In comparison, the color resolution of a color camera sensor is very crude as is seen by the broad curves of red, green and blue sub-pixels in the plot of FIG. 16. The embodiments discussed in this application make use of color camera sensors due to their ability to provide rich morphology data at low cost, even at the cost of loosing color spectral resolution. Nevertheless, surprisingly, the humble color resolution of camera sensors are still sufficient to extract useful color information with which to separate contributions of different types of fluorescent biomolecules and hence probe the state of fungal spores. To further illustrate this point, a further detailed embodiment is discussed below.

Referring to FIG. 28S, consider fungal spores for which the dominant biomolecules contributing to fluorescence images are riboflavin (understood to also include related biomolecules), NADH (also understood to include related molecules including NADPH), and tryptophan (also understood to include any other fluorescing amino acids). Such fluorescing biomolecules may be excited by blue or ultraviolet (UV) light of wavelength $\lambda_{EX}$ resulting in the emission of light of wavelength $\lambda_{EM}$. FIG. 28S represents the wavelength of color characteristics of these three types of biomolecules where inside the heavy circles are values wavelength pairs ($\lambda_{EX}$, $\lambda_{EM}$) of relatively stronger fluorescence and inside the finer lines relatively weaker but non-zero fluorescence. Riboflavin has three particularly favorable excitation wavelengths, all of which result in the same emission wavelength.

In this detailed embodiment, four fluorescence images of fungal spores are captured at excitation wavelengths of about 445 nm, 365 nm, 325 nm and 280 nm. These excitation wavelengths correspond to the dot-dot-dash horizontal lines drawing in FIG. 28S. Corresponding biomolecule fluorescence wavelength conversions are illustrated in FIG. 29. Riboflavin results in emission at about 520 nm as indicated by items (a), (b), (d) and (f) of FIG. 29, while NADH results in emission at about 455 nm in items (c) and (e). Only the shortest wavelength excitation 280 nm is able to excite tryptophan, and only the longer-wavelength tail of the resulting emission spectrum is in the visible spectrum and detectable by the camera sensor (according to FIG. 16). In this example, only riboflavin contributes to fluorescence due to 445 nm excitation. The fluorescence signal from 365 nm illumination is due to both riboflavin and NADH with riboflavin dominating. The fluorescence signal from 325 nm also is due to both riboflavin and NADH, but this time with NADH dominating. Finally the fluorescence signal from 280 nm includes a contribution of tryptophan as well as riboflavin.

The distributions of flavins, NADH, and proteins (amino acid chains, most of contain at some level the amino acid tryptophan) provide important clues about the state of a spore. Let "$C_{RIBOFLAVIN}(x,y)$" represent the distribution or concentration of riboflavin and related biomolecules as a function of the coordinates (x,y) of the camera sensor pixels within the outline of a fungal spore. Likewise let us define "$C_{NADH}(x,y)$" and "$C_{TRYPTOPHAN}(x,y)$" similarly for the distributions of NADH and tryptophan. For example, the distributions "$C_{RIBOFLAVIN}(x,y)$" and "$C_{NADH}(x,y)$" may have peaks of high concentration at the locations of mitochondria while the distribution "$C_{TRYPTOPHAN}(x,y)$" may have peaks where there are high concentrations of proteins. The biomolecule distributions "$C_{RIBOFLAVIN}(x,y)$", "$C_{NADH}(x,y)$" and "$C_{TRYPTOPHAN}(x,y)$" are of interest for assessing the state of a fungal spore.

However, these biomolecule distributions of interest cannot be directly measured, but must be inferred from red, green and blue color pixel data from camera images. Let "$RGB_i(x,y)$" represent the signal from an RGB-camera-sensor color subpixel "i" (where i=RED, GREEN or BLUE) for the pixel at location (x,y); a superscript may be added to explicitly define the excitation wavelength $\lambda_{EX}$. FIG. 30 provides a general formula for relating measured pixel values "$RGB_i(x,y)$" to the biomolecule distributions "$C_j(x,y)$" where j=RIBOFLAVIN, NADH or TRYPTOPHAN. The quantum efficiencies of the color sub-pixels as a function of wavelength, such as plotted in FIG. 16, are represented by "$p_i(\lambda)$" where again i=RED, GREEN or BLUE. The fluorescence characteristics of the biomolecules, such as plotted in FIG. 28S, is represented by the factor "$F_j$" where a superscript "$\lambda_{EX} \to \lambda_{EM}$" indicates a two-dimensional location ($\lambda_{EX}$, $\lambda_{EM}$) in the plot of FIG. 28S. In FIG. 31, the general formula of FIG. 30 is explicitly applied to the biomolecule fluorescences of FIG. 29.

From captured fluorescence images, the numerical values of left hand sides of the equations of FIG. 31 are known. In the method of this embodiment, the color sensitivity characteristics of the camera sensor, "$p_i(\lambda)$", are predetermined via calibration procedures or other techniques.

Similarly, laboratory studies of the fluorescence properties of biomolecules of interest, perhaps as reported in the published scientific literature, predetermine the values of "$F_j$" for sets of wavelengths "$\lambda_{EX} \to \lambda_{EM}$" of interest. As a result, for each pixel within the outline of a fungal spore, in FIG. 31, there are ten linear equations with three unknowns, namely the biomolecule distributions "$C_{RIBOFLAVIN}(x,y)$", "$C_{NADH}(x,y)$" and "$C_{TRYPTOPHAN}(x,y)$." Hence there is redundant information from which to compute the three biomolecule distributions with the aid of well-known methods of solving sets of linear equations. Thus, based on the equation of FIG. 30, it is possible to determine biomolecule distributions from captured fluorescence images.

In other words, as long as the number of independent equations is greater than or equal to the number of biomolecule distributions to be extracted, it is feasible to do so. For example, even without the images for 445 nm blue illumination and 325 nm UV illumination, the distributions of the three types of biomolecules may still be determined. Similarly, if all four illumination wavelengths are retained, but several additional biomolecules are found to contribute to the fluorescence images, the distributions of the additional types of biomolecules may also be determined.

Illumination wavelengths 365 nm, 325 nm and 280 nm are outside the visible spectrum and well into the ultraviolet spectrum to which the camera sensor does not respond. However, the longest illumination wavelength 445 nm is still within the visible spectrum and corresponds to a blue color. Referring to FIG. 16, signals of blue camera sensor sub-pixels, and even green camera-sensor sub-pixels, will be dominated by direct scattering of the blue 445 nm light making it difficult to detect the presence of relatively weaker 520 nm fluorescent light. The 445 nm→520 nm fluorescence signal is most easily detected with the red camera-sensor sub-pixels as red sub-pixels have some sensitivity to green 520 nm fluorescent light ($p_{RED}(520$ nm$) \neq 0$) and at the same time the red sub-pixels are very insensitive to the blue 445 nm illumination light ($p_{RED}(445$ nm$) \approx 0$). Red camera-sensor sub-pixels signals for 445 nm illumination have the advantage of providing images of the flavin distribution unmixed with fluorescent signals of biomolecules excited only by ultraviolet light.

Figures 32, 33:
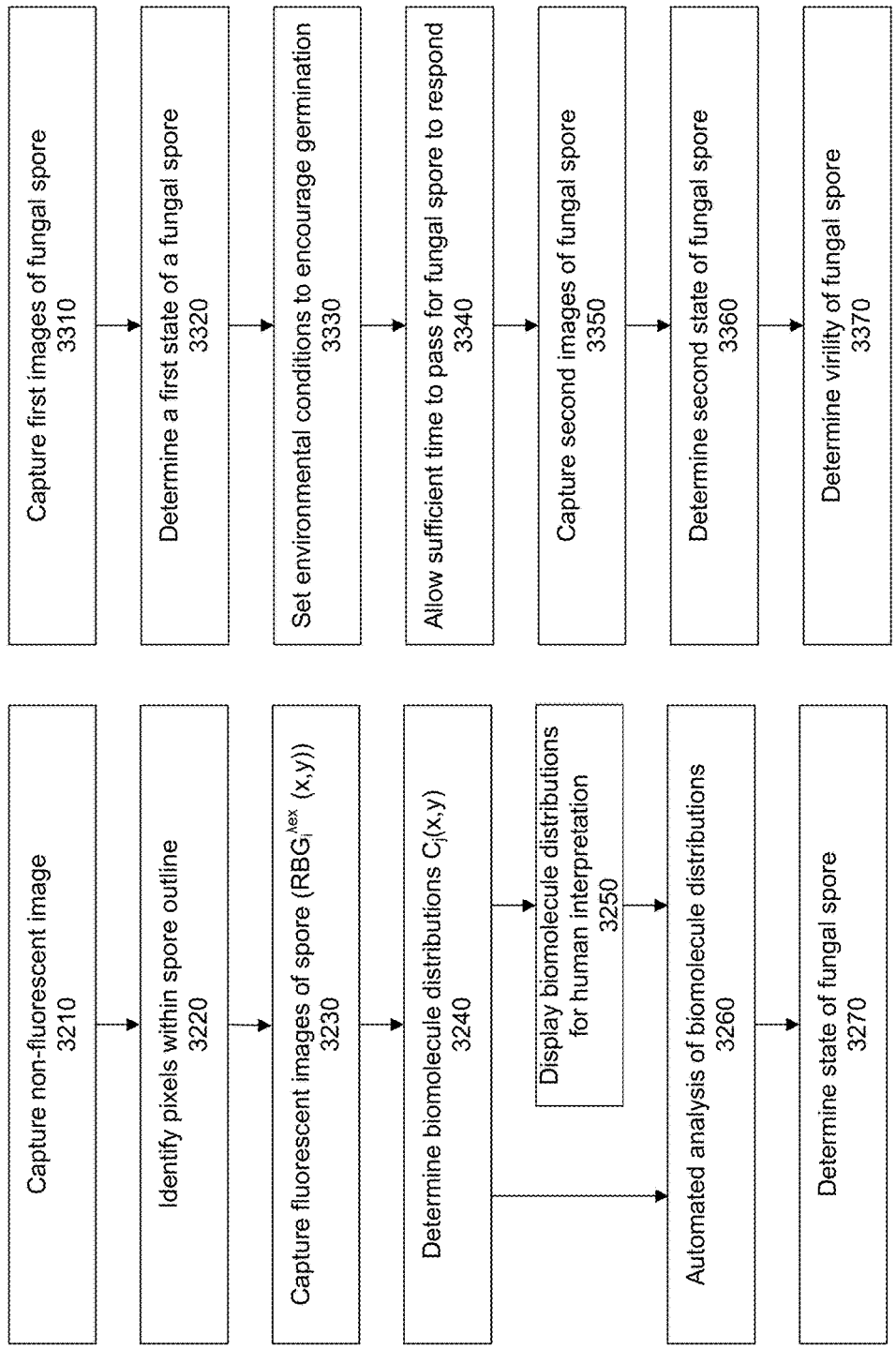
FIG. 32 shows a flow chart of a process for assessing a fungal spore according to a specific embodiment.
FIG. 33 shows another flow chart of a process for assessing a fungal spore according to a specific embodiment.

The above discussion corresponds to steps 3210, 3220, 3230 and 3240 of the flow chart of FIG. 32. In a specific embodiment, a method may include capturing, by a camera sensor, an image of a fungal spore while the fungal spore is illuminated with UV light; inferring concentrations of biomolecules of interest within the fungal spore by correlating, associating, or relating a value of a pixel located at coordinates (x,y) on the image to a concentration of a biomolecule of interest as being at the coordinates (x,y) on the image; obtaining reference information comprising fluorescent properties of the biomolecules of interest associated with known states of the fungal spore; obtaining camera sensor information comprising color sensitivity characteristics of the camera sensor; and processing the inferred concentrations of the biomolecules of interest within the fungal spore with the reference and camera sensor information to identify a state of the fungal spore.

In applications in which skilled specialists are available to interpret the data, it may be advantageous, as in step 3250, for the system to visually present to a human operator the results of the computations of biomolecule distributions. In an embodiment, the process ends at step 3250 and steps 3260 and 3270 are omitted. In this specific embodiment, the monitor does not proceed to determine the state of fungal spore, but rather leaves that to a human operator. Alternatively, the system may have appropriate software to provide automatic determination of the state of the fungal spore based on the biomolecule distributions within the outline of the fungal spore.

Of particular interest in agricultural application is the difference between a viable spore of a fungal pathogen that is capable of spreading disease and a fatally injured or dead spore that is not capable of spreading disease. That is, it is of interest to test the infectiousness of detected pathogenic fungal spores. A conventional laboratory test of spore virility is to incubate spores in a nutrient medium under appropriate temperature and humidity conditions and observe whether or not the spores grow into visible mold colonies. While a convincing test of infectiousness, the time delay and labor costs of such a test is often disadvantageous. Building on the method of FIG. 32, a much faster and lower-cost test of fungal spore infectiousness is provided.

Referring to FIG. 33, step 3310 corresponds to steps 3210, 3220 and 3230 of the flow chart of FIG. 32 and results in the capture of both visible light and fluorescent light images of a fungal spore. Step 3320 of FIG. 33 corresponds to steps 3240 through 3270 in which the state of the fungal spore is determined. In particular, step 3320 determines a first state of a capture fungal spore, namely the state of the spore shortly after being captured from ambient air.

In step 3330, the captured fungal spore is subjected to conditions that encourage spore germination and growth.

Conditions to encourage germination may include, but are not limited to, humidity, temperature, and availability of nutrients. For example, via motion of the adhesive coated tape within the cartridge, a spore sample may be moved to a location of elevated humidity and temperature, and perhaps a small drop of sugar water wets the fungal spore. In other words, in a specific embodiment, a particle monitor includes an environmental regulator, device, or subsystem. The environmental regulator is responsible for providing a controlled environment for the captured fungal spore in order to assess the state of a captured fungal spore. The environmental regulator may include, for example, a humidifier, dehumidifier, or both to control or change a humidity level within the particle monitor; an air conditioner, heater, or both to control or change a temperature within the particle monitor; a feeder to provide the fungal spore with nutrients, or combinations of these.

In step 3340, enough time is allowed to pass during which the fungal spore responds to germination inducing conditions with a change in metabolic state. For example, a delay may be implemented between the setting of the environmental conditions and capturing of a second image. It is important to note that the wait time of step 3340 is very brief compared to the time it takes a spore to grown into a mold colony as in conventional viability tests. It may not even be necessary to wait for the spore to split into multiple cells. To determine whether or not a fungal spore has been killed or fatally injured by fungicide, it may be sufficient to observe metabolic changes, or lack thereof, with a single spore cell. For example, it may be sufficient to observe the degree of increased metabolic activity in the spore's mitochondria as determined from the riboflavin and NADH fluorescence signals.

In step 3350, steps 3210, 3220 and 3230 of FIG. 32 are repeated in order to capture second images of the fungal spore after it has been subjected to germination inducing conditions. In step 3360, steps 3240 through 3270 are repeated but this time with the second rather than first captured set of images resulting in the determination of a second post-germination-condition state of the fungal spore. In step 3370, the second fungal spore state as determined in step 3360 is compared to the first fungal spore state as determined in step 3320 and a determination is made of the infectiousness of the fungal spore captured from ambient air.

In an embodiment, a feature of the system analyzes both morphology and fluorescence properties of particles that have been trapped and imaged using a color camera sensor. The combined analysis can be used to not only identify a particle, but to also assess a state of the particle (e.g., healthy versus not healthy, active versus dormant, or alive versus dead). The morphology analysis facilitates an identification of the various parts or anatomy of a cell (e.g., mitochondria versus cell wall). Consider, as an example, a fungicide designed to interrupt a specific process of the cell or to target a specific portion of the cell (e.g., mitochondria). Since different parts of the cell may have differing properties with respect to fluorescence, analyzing images captured under different illumination conditions can be used to determine whether or not the fungicide has been effective.

Determining a state of a fungal spore may include analyzing context information. For example, if the context information indicates that environmental conditions are conducive to germination and an image analysis indicates that the fungal spore is inactive, a determination may be made that the fungal spore is actually dead rather than in a dormant or hibernating state. Conversely, if the context information indicates that environmental conditions are not conducive to germination and an image analysis indicates that the fungal spore is inactive, a determination may be made that the fungal spore may be in a dormant state and a further analysis is required to determine whether or not the spore is dead.

FIG. 34 illustrates the contents of an exemplary particle information packet 3400 that may be generated by particle monitor 105 in an embodiment, in connection with analyzing particles captured by the particle monitor. FIG. 35 shows a particle information packet history.

Referring now to FIG. 34, shown are parameters of a data structure storing characteristics of a particle and metadata associated with the particle. The data structure may be stored in the memory or storage of a physical computing device. The data structure may be implemented, for example, as a table of a database. While FIG. 34 shows some specific examples of particle characteristics and metadata that may be collected, derived, and stored for a particle, it should be appreciated that there can be instead or additionally other particle characteristics, associated metadata, or both that may be stored.

Consider, as an example, a particle monitor placed in a vineyard to monitor pathogenic fungal spores such as powdery mildew. In this context, FIG. 35 illustrates an example hypothetical history of one particle information packet.

When a particle is observed in the field of view of the camera sensor of the particle monitor, a particle information packet 3400 (FIG. 34) is created (step 3505—FIG. 35). At creation, it includes a packet header 3410 (FIG. 34) including particle ID number 3412 and pointers 3414 to various blocks in the packet, a particle ID block 3420 containing items 3421 through 3426, as well as an objectives block 3430 with an application type 3432 of "agricultural monitoring" and a definition of particles of interest 3434 of "powdery mildew."

In the example shown in FIG. 34, the particle ID block includes a timestamp 3421, particle collection device serial number 3422, device GPS coordinates 3423, adhesive-coated tape reel number 3424, x-coordinate of particle along length of tape 3425, and y-coordinate of the particle (perpendicular to the length of tape) 3426.

In a specific embodiment, the particle identification subsystem includes a pixel-to-tape mapping unit that maps a location of a particular particle that has been captured within an image to the particle's physical location on the tape. The mapping unit determines a first location of a particle within an image. The first location may be a set of pixel coordinates. For example, a pixel coordinate X may represent the particle's location as measured along an x-axis from a reference point in the image. A pixel coordinate Y may represent the particle's location as measured along a y-axis from the reference point in the image. The pixel coordinates can be mapped into real space or into real x-y coordinates as measured from a reference point on the tape.

The particle collection cartridges may be assigned unique serial numbers so that images of the particles can be associated with corresponding collection cartridge having the physical particles. As discussed, in an embodiment, the particle monitor includes a counter that tracks a position of the tape. For example, the counter may track an amount or length of tape taken up by the uptake reel, an amount or length of tape unspooled from the supply reel, or both. Tracking the position of the tape allows for cross-referencing the images with the corresponding physical particles on the tape.

In another specific embodiment, the tape may include a set of markers that can be captured in the particle images. The markers may be individually or sequentially numbered and distributed at various intervals along a length of the tape. An interval may correspond to a width of a field of view of the camera sensor so that a marker associated with the interval will be captured in an image. The marker allows for cross-referencing the image with the portion of tape where the corresponding physical particles have been trapped. The markings may be made using any technique for making a visible impression on the tape including, for example, printing, silkscreen printing, stamping, or chemical processing. Alternatively, the tape may include a magnetizable layer for magnetic marking and readout of tape locations.

At this point, status block 3440 contains a measurement status flag 3442 and an analysis status flag 3444 with no bits set, and null work-in-progress and definitive particle classifications 3446 and 3448. This is the state of particle information packet 3400 at step 3505 of FIG. 35.

At step 3510 (FIG. 35), the particle monitor embedded software stores into data block 3480 (FIG. 34) sensor data 3481 for those RBG camera pixels including and surrounding the detected particle. At this step, a bit in measurement status flag 3442 is set to indicate the capture of camera sensor data 3481. At this point, no decision has been made whether the detected particle is even a biological particle rather than, for example, a dust particle.

The first analysis step is step 3515 (FIG. 35). This first analysis step involves estimating the diameter or longest major axis of the detected particle. From this measurement there results a work-in-progress or preliminary particle classification 3446 (FIG. 34) such as "<5 microns" (less than 5 microns), "10-15 microns" (between 10 and 15 microns), "35-40 microns" (between 35 and 40 microns) or ">200 microns" (greater than 200 microns). A corresponding bit in the analysis status flag is set. If the result had been outside the size of powdery mildew, a quick definitive particle classification 3448 of "not powdery mildew" would have been made on the basis that the particle size is not compatible with the particles of interest 3434.

However, in this case we imagine a work-in-progress classification 3446 that is compatible with the particles of interest. However, this size range may also compatible with many particles that are not of interest, such as dust particles that happen to be in this size range.

Given that the possibility remains that the packet might correspond to a particle of interest, the software of the monitor makes a decision to analyze particle shape. This is step 3520 of FIG. 35. If the outcome had been a shape inconsistent with powdery mildew a definitive or final particle classification 3448 (FIG. 34) of "not powdery mildew" would have been made.

However, we imagine a resulting work-in-progress classification 3446 of morphological characteristics (e.g., surface texture, shape, and size) consistent with powdery mildew. In engineering practice, the work-in-progress classification 3448 can be a numerical code that can be configured, by for example, scientists and software engineers or other users. As with all analysis steps, another bit in the analysis status flag 3444 is set after completion of this analysis step.

Consider that the work-in-progress classification does not exclude the possibility that the particle is powdery mildew. As a result, in step 3525 (FIG. 35), the monitor's software makes a decision to analyze color information in camera sensor data 3481 (FIG. 34). If the result had been a color not characteristic of powdery mildew, the processing of the particle information packet 3400 would have ended with a "not powdery mildew" definitive classification 3448. However, to provide a more instructive example, imagine step 3525 (FIG. 35) results in a work-in-progress classification 3446 (FIG. 34) of morphological and color characteristics consistent with powdery mildew.

Note that in steps 3520 (FIG. 35) and 3525, no new data is collected, only new analyses of previously measured data stored in data block 3480 (FIG. 34).

At the completion of step 3525 (FIG. 35), the embedded software of the monitor has not yet reached a definitive classification, and may not have the best information to decide what comes next. At such a point, the monitor looks for guidance from software on the cloud. In step 3530, the embedded software transmits the particle information packet 3400 (FIG. 34) to the cloud.

The cloud software has access to great deal more information than does the embedded software of the particle monitor. For example, in step 3535, the cloud software may have access to databases where the system collects and stores relevant information such weather patterns, elevations at various GPS coordinates, and historical records of powdery mildew occurrences. Powdery mildew grows well in environments of high humidity and moderate temperatures. The device GPS coordinates 3423 and time stamp 3421 (FIG. 34) of particle identification block 3420 can be used to retrieve past or historical weather conditions. If the historical weather conditions indicate a lack of rain and humidity, the presence of powdery mildew can be excluded. However, in FIG. 35 we consider the case that the contextual information available on the cloud does not exclude detection of particles of interest 3434 (FIG. 34).

To provide better discrimination between types of fungus, the cloud software may decide that better morphology information is desirable and in step 3540 (FIG. 35) sends a request to the particle monitor to collect further camera images of the particle with one or more alternate focal depths. Focal depth may be varied by mechanical movement of lens and/or camera sensor, by electronic control of a variable lens, by software control of processing of image data from a light-field camera system, or combinations of these.

The request received by the particle monitor triggers step 3545 and the requested measurements are made and added to the alternate focus data 3482 (FIG. 34) of data block 3480. With this additional data, in step 3550, a more refined shape or morphology analysis is performed. The analysis of step 3550 may be performed by embedded software of the particle monitor (e.g., analyzed locally at the particle monitor), by cloud software (e.g., analyzed remotely by a cloud server), or both.

By capturing images of the particle at multiple focal depths, all parts of a particle can be brought into focus, thus providing more complete morphological information. For translucent particles, a scan of focal depth may be used to capture three-dimensional particle structure information.

In step 3555, the cloud software also sends a request to the particle monitor to collect further camera images with an alternate illumination source. In step 3560 the alternate illumination data is stored as item 3483 (FIG. 34) in data block 3480.

Here we assume that the monitor is equipped with a quantum-dot LED illumination source tuned to the absorption of powdery mildew. The quantum-dot LED illumination source may be optional hardware that was included in the particle monitor configuration due to the desire to deploy the monitor for agricultural monitoring; in this sense the definition of particles of interest 3434 may not only influence processing of a particle information packet 3400, but also influence the hardware configuration of the particle monitor.

Let us assume that such a powdery mildew sensitive alternate illumination is used and in step 3565 (FIG. 35), analysis (local, on the cloud, or both) of all the color data in block 3480 (FIG. 34) confirms the presence of powdery mildew.

At this point, the evidence is strong that powdery mildew has been determined. However, before disturbing the agricultural management consultant with an alert, it may be prudent to obtain a second opinion from a human technician. In the scenario of FIG. 35, at step 3570, the cloud software sends a request for a second opinion from a trained technician. In step 3575, resulting technician notes are stored in data block item 3487 (FIG. 34). The request may include particle data collected by the system and the system's determination based on the particle data. This information may be displayed, for example, on an electronic screen such as via a web page provided by the system. The web page is accessible by the trained technician. The web page may further include an input box that the technician can use to enter notes regarding the accuracy of the identification and other information.

The technician may in turn request a third opinion by a scientific specialist whose notes are captured in step 3580 and are stored in data block item 3488 (FIG. 34). In this scenario, we imagine that the scientific specialist is fully convinced and the identification is definitively confirmed 3448 (FIG. 34). It is now time to inform the agricultural management consultant that powdery mildew has been detected (step 3585).

In the interests of cost and a fast response, it may well be more exceptional than routine to involve humans, as in steps 3575 and 3580, in which it is otherwise an automated particle detection and classification system. This exceptional scenario is considered here to more fully describe a deeply multi-tiered particle discrimination scenario. A deeply multi-tiered scenario may also be one where the user of a particle monitoring device has required human review of the particle data every so often (e.g., periodically). An example of this is an institutional, commercial, or single user with multiple systems deployed across a region and operating 24 hours a day 7 days a week. In such a scenario, human involvement as described in steps 3575 and 3580 may take place as part of a quality assurance procedure.

For example, a human review of particle data may be required after one hundred, one thousand, ten thousand, a million, or another number of particle detections have occurred. A human review of particle data may be required every hour, once a day, once a week, once a month or at some other interval of time. The criteria or frequency for when human review of particle data is required can be configurable such as by a user or administrator of the system. The system (e.g., monitor, cloud server, or both) can track this criteria to determine when a human review of particle data is required. When a human review of particle data is required, the system can send out a notification to the human reviewer to request a review of the particle data. The request may include the particle data and an identification made based on the particle data. The human reviewer can review the particle data to see whether or not the particle identification was correct. Further leveraging of the talents of the human reviewer may be provided by using results of human reviews as input to automated machine learning algorithms so that reliance on human review decreases with time.

Even after the user has been alerted, the particle information packet may continue to be processed for quality control and algorithm development purposes. In step 3590, the used reel of adhesive-coated tape containing the detected particle is collected and stored in an archive. Later, in step 3595, a bioassay using anti-bodies specific to powdery mildew is performed to verify beyond a shadow of a doubt that the particle was correctly classified—or to learn that a mistake was made and that the particle information packet should be closely studied to determine what changes need to be made to the algorithms of the various tiers of the particle discrimination system. Depending on a particle information packet's history, the data block 3480 may also contain alternate tape location camera sensor data 3484, information from the cloud on local weather conditions 3485, information from the cloud on known seasonal pathogens 3486, laboratory microscope images 3489 of archived particles, bio-assay data 3490, expert-technician notes 3491 and/or expert scientist notes 3492. The particle information packet may include a relationship block 3460 storing sequence numbers of related particles 3462 and a nature of relationship of related particles 3464.

Principles and aspects of the particle information packet may further be applied to assessing the state of an identified particle such as assessing the state of the powdery mildew.

Principles and aspects of the system may also be applied to drones configured for agricultural monitoring. One example of a drone is an unmanned aerial vehicle (UAV). Other examples of drones are unmanned, but not necessarily flying or aerial vehicle. Land-based drones may include an autonomous 4-wheeler, sprayer, tractor trailer, and the like that may be used in a cultivated field such as a vineyard. In an embodiment, a drone includes a particle monitor. The drone can be programmed to fly over an agricultural area (e.g., vineyard or farm) in order to monitor for agricultural pathogens.

Table D below shows a flow for spore state discrimination according to a specific embodiment.

TABLE D

| Step | Description |
|---|---|
| 1 | Define a plurality of types of fluorescent biomolecules of interest within the fungal spore. |
| 2 | Store a first plurality of predetermined color characteristics of fluorescent light for each type of fluorescent biomolecules of interest, each predetermined color characteristic of the first plurality of predetermined color characteristics corresponding to excitement of a respective fluorescent biomolecule of interest under ultraviolet (UV) light having first spectral characteristics. |
| 3 | Store a second plurality of predetermined color characteristics of fluorescent light for each type of fluorescent biomolecules of interest, each predetermined color characteristic of the second plurality of predetermined color characteristics corresponding to excitement of a respective fluorescent biomolecule of interest under UV light having second spectral characteristics, different from the first spectral characteristics. |
| 4 | Store a third plurality of predetermined color characteristics of fluorescent light for each type of fluorescent biomolecules of interest, each predetermined color characteristic of the third plurality of predetermined color characteristics corresponding to excitement of a respective fluorescent biomolecule of interest under UV light having third spectral characteristics, different from the first and second spectral characteristics. |
| 5 | Direct a flow of air comprising the fungal spore to a collection cartridge. |
| 6 | Trap the fungal spore within the collection cartridge. |
| 7 | Illuminate the fungal spore in the collection cartridge with visible light. |
| 8 | While the fungal spore is illuminated with the visible light, capture a first two-dimensional color image of the fungal spore. |
| 9 | Analyze the first two-dimensional color image to identify an outline of the fungal spore, the outline of the fungal spore being defined by a set of image pixels receiving light from the fungal spore. |

TABLE D-continued

| Step | Description |
| --- | --- |
| 10 | Illuminate the fungal spore in the collection cartridge with UV light of the first spectral characteristics. |
| 11 | While the fungal spore is illuminated with the UV light of the first spectral characteristics, capture a second color image of the fungal spore. |
| 12 | Measure from the second color image a degree and color of fluorescence for each pixel within the outline of the fungal spore. |
| 13 | Illuminate the fungal spore in the collection cartridge with ultra-violet (UV) light of the second spectral characteristics. |
| 14 | While the fungal spore is illuminated with the UV light of the second spectral characteristics, capture a third color image of the fungal spore. |
| 15 | Measure from the third color image a degree and color of fluorescence for each pixel within the outline of the fungal spore. |
| 16 | Illuminate the fungal spore in the collection cartridge with UV light of the third spectral characteristics. |
| 17 | While the fungal spore is illuminated with the UV light of the third spectral characteristics, capture a fourth color image of the fungal spore. |
| 18 | Measure from the fourth color image a degree and color of fluorescence for each pixel within the outline of the fungal spore. |
| 19 | Based on the measurements from the second, third, and fourth color images of degree and color of fluorescence, estimate a concentration of each type of fluorescent biomolecule of interest for each image pixel within the outline of the fungal spore. |
| 20 | Generating two-dimensional images of concentrations of the fluorescent biomolecules of interest with outlines of fungal spores. |
| 21 | Based on information from a two-dimensional distribution of fluorescent biomolecules of interest within the outline of the fungal spore, determine the state of the fungal spore. |
| 22 | Correlate state of fungal spore with other variables such as time, temperature, humidity, and fungicide treatments. |
| 23 | Issue alerts and updates to responsible parties |

In Step 1, the types of fluorescent molecules are of interest are defined. In mathematical terms, this may include, for example, defining the molecule enumeration index "j" of the equation of FIG. 30. In the example in FIGS. 30 and 31, the molecule enumeration index "j" takes on the values of "riboflavin", "NADH" and "tryptophan". This is a reasonable choice for the determination of the state of biological particles such as fungal spores or pollen grains. This is because flavins (see FIG. 46) and NADH (see FIG. 47) are fluorescing biomolecules essential to cellular metabolism and tryptophan (see FIG. 48) is an essential amino acid used in the construction of proteins.

If the particles of interest are diesel particulate matter and the state of interest is the degree of chemical toxicity, then the defined types of fluorescent molecules of interest may be polycyclic aromatic hydrocarbons (PAHs) such as anthracene (see FIG. 41), triphenylene (see FIG. 42), and coronene (see FIG. 43).

If particles of interest are diesel particulate matter, but pollen grains and mold spores are background particles that need to be rejected, the molecules of interest may include riboflavin, NADH and tryptophan as well as PAHs.

It is desirable that for the given application that the set of molecules of interest be 'complete' in the sense that no molecules outside the set contribute significantly to measured fluorescent signals; this aids interpretation of the signals. More generally, in applying the described systems and techniques to a specific application, an important step is to determine (by experiment or literature research) the types of fluorescent molecules of interest. Such a determination of the types of fluorescing molecules of interest may well be done by engineers or scientists associated with the company providing the particle-monitoring device 700. The resulting information may be coded into software or initialization files associated with the device. For example, the initialization files may be stored in the particle monitor device. The initialization files may be transmitted from a central server, over a network, and to the particle monitor device. The initialization files can be updated remotely, locally (e.g., copied from pluggable USB drive inserted into monitor device), or both. In embodiment, a method includes storing first initialization at a particle monitor device where the first initialization files specify first fluorescent molecules of interest; receiving at the particle monitor second initialization files where the second initialization files specify second fluorescent molecules of interest, different from the first fluorescent molecules of interest; and replacing the first initialization files with the second initialization files.

Taking the example of riboflavin, NADH and tryptophan as the types of fluorescent molecules of interest, in Step 2 the fluorescent behavior of these molecules of interest in response to a particular UV illumination source is determined and stored for later use in Step 19. For example, particle-monitoring device 700 may include a UV illumination source with a representative wavelength of 365 nm that results in riboflavin fluorescing with a green color having a representative emission wavelength of 520 nm, NADH fluorescing with a blue color having a representative emission wavelength of 455 nm, and tryptophan not fluorescing at all. It is to be understand that a 365 nm UV light source, such as a 365 nm UV LED, does not only generate photons of wavelength 365 nm, but rather generates photons with a wavelength spectrum of finite width and peaking around 365 nm. It is the color characteristics of emitted fluorescent light in response to illumination by the spectrum from the UV light source that is of interest. It is to be understood that in concisely referring to an excitation wavelength of 365 nm from a UV light source, we mean the entire spectrum from the UV light source. Similarly in concisely referring to a fluorescent emission wavelength of, say, 520 nm, it is understood that a full description of the color of fluorescently emitted light is a spectrum peaking near 520 nm. In FIGS. 30 and 31, the color characteristics of the fluorescent molecules riboflavin, NADH and tryptophan under 365 UV illumination are notated with the letter "F" with subscript "RIBOFLAVIN" and superscript "365 nm→520 nm", the letter "F" with subscript "NADH" and superscript "365 nm→455 nm", and the absence of a letter "F" with subscript "TRYPTOPHAN" with superscript "365 nm→ . . . ". The quantitative values, or absences, of these "F" values quantify a plurality of predetermined color characteristics of fluorescent light for each type of fluorescent molecule of interest in response to one particular type of UV light source (e.g. a 365 nm UV LED) having its own UV spectral characteristics. Determination of these "F" values, or similar information in a different format, may be done by engineers or scientists associated with the provider of particle-monitoring device 700, and then coded into software or initialization files associated with the device.

In some applications, one UV illumination source may be sufficient. In other applications it may be desirable to enrich measured data with the aid of a second UV light source with different spectral characteristics. For example, particle-monitoring device 700 may include a second UV LED with a representative wavelength of 325 nm. If so, the method proceeds to Step 3 that repeats the previous step for the second UV light source. In the example of FIGS. 30 and 31, Step 3 may result in the determination of "F" values for 325 nm→520 nm riboflavin fluorescence and 325 nm→455 nm NADH fluorescence, and an absence or zero value of an "F" value for tryptophan.

If particle-monitoring device 700 includes a third UV light source, then optional Step 4 applies. For example, particle-monitoring device 700 may include a third UV LED with a representative wavelength of 280 nm. In the example of FIGS. 30 and 31, Step 4 may result in the determination of "F" values for 280 nm→520 nm riboflavin fluorescence and 280 nm→400 nm tryptophan fluorescence, and an absence or zero value of an "F" value for NADH. While not included in Table D, further steps may be inserted to accommodate additional UV light sources. Each additional UV light source enriches the data available but also adds cost. In many applications the best balance between cost and performance may be with one, two or three UV light sources.

As seen in FIGS. 28, 29 and 31, as well as the earlier discussion of these figures, riboflavin fluorescence is also possible with 445 nm blue light. It is to be understood that in Steps 2, 3 or 4 above, 'UV light' may be interpreted as excitation light of sufficiently short wavelength to induce visible-light fluorescence of molecules of interest, which in some cases the excitation light may be within the visible light spectrum.

In the example of FIG. 28S, each molecule of interest has only one emission wavelength peak value independent of the excitation wavelength. For example, riboflavin emits a spectrum of wavelengths with a peak wavelength about 520 nm, independent of whether the excitation wavelength is 445 nm, 365 nm, 325 nm or 280 nm. This behavior is typical. However, if a molecule had two fluorescence emission peaks, that could easily be accommodated with additional "F" values.

In Steps 5 and 6, particles of interest are captured within the collection cartridge and moved to the inspection zone as described previously. A visible light image is captured in Steps 7 and 8. A first fluorescence image under UV light illumination is captured in Steps 10 and 11. Optional second and third fluorescence images under second and third UV light sources are captured in steps 12 and 13 and steps 15 and 16 respectively. While the visible light image is captured first in Table D, the images may be captured in any order. Furthermore, the capture of additional UV fluorescence images of Steps 12 and 13, and of Steps 15 and 16, may be conditional on whether the previously captured images are deemed sufficient to determine the state of the particles of interest. For all images, two-dimensional color information is captured in the form of RGB pixel values from the camera sensor 1420. Such color image data is represented by "RGB(x,y)" with a subscript of either "RED", "GREEN" or "BLUE" in FIGS. 30 and 31 where each pixel has different coordinates "(x,y)". RGB color pixel data for UV-excited fluorescence is captured much the same way as for visible light scattering, but the captured image data is processed differently.

In Step 9, the visible light image from Steps 7 and 8 is analyzed to determine outlines of particles of interest, that is, it is determined which camera sensor pixels correspond to (x,y) locations inside particles of interest and which to (x,y) outside particles of interest. Alternatively, one or more of the UV fluorescence images, perhaps in combination with the visible light image, is used to determine particle outlines. After completion of Step 9, UV fluorescence color image data corresponding to pixels within particles of interest may be determined as in Steps 12, 15 and 18.

The steps leading up to Step 19 provide rich image data not only to recognize particles of interest, but also to determine their state. In particular, in Step 19, the concentration of each type of fluorescence molecule of interest may be determined from the captured image data, the molecule fluorescence color characteristics determined in Steps 2, 3 and 4 as well as the pixel color sensitivities of camera sensor 1420. In FIGS. 30 and 31, the pixel color sensitivities are represented by the letter "p" with a subscript specifying the pixel color ("RED", "GREEN" or "BLUE") and an argument specifying the wavelength of the fluorescently emitted light, or more generally the wavelength spectrum of the fluorescently emitted light. The numerical "p" values may be determined along with "F" values in Steps 2, 3 and/or 4. Referring to the formula of FIG. 30, the RGB(x,y) values within particles of interest for the one or more UV fluorescence images are known from Steps 12, 15 and/or 18. The "p" and "F" values are known from Steps 2, 3 and/or 4. Using this information and solving the resulting set of simultaneous linear equations such as illustrated in FIGS. 30 and 31, the concentrations "C(x,y)" for each molecule of interest may be determined as a function of pixel location (x,y). For example, if the molecules of interest are riboflavin, NADH and tryptophan, the resulting concentration maps may be notated as "$C_{RIBOFLAVIN}(x,y)$", "$C_{NADH}(x,y)$" and "$C_{TRYPTOPHAN}(x,y)$".

Steps 7 and 8 may be combined with Steps 10 and 11. That is, during an exposure for a camera sensor image capture, the particles of interest may be illuminated by visible light (Step 7) and by UV light (Step 10), either simultaneously or sequentially. Because exposure times for UV light are typically longer than for visible light, the visible light source might flash for a fraction of a second during UV illumination lasting several seconds. A shorter visible light illumination may occur before, during or after UV illumination; if during the visible light illumination may occur at any time during the UV illumination period. The resulting captured image serves as both the scattered visible light image of Step 8 and the fluorescence image of Step 11. From this single combined RGB image, the fungal spore outline may be determined (Step 9) and the fungal spore fluorescence color may be determined (Step 12). Likewise Steps 7, 8 and 9 may be repeated and combined with Steps 13, 14 and 15 as well as with Steps 16, 17 and 18.

In a specific embodiment there are four illumination sources that in plan view illuminate the inspection zone 840 from the four compass directions. Illumination directions may be at an angle of 60 degrees with respect to the vertical optical axis of the camera sensor. The north illumination source is a UV LED while the east, south and west illumination sources are white LEDs. In an embodiment all LEDs generate un-polarized light. The camera sensor exposure time is 15 seconds during which the UV LED is on. After 14 seconds of exposure and UV illumination, the east white LED is turned on for 0.033 seconds, after which the south LED is turned on for 0.033 seconds and then the west LED is turned on for 0.033 seconds. For at least some types of mold spores, it has been observed that images captured under such illumination conditions provide excellent data for extracting morphological data including a determination of the outlines of spores. In some applications it may be sufficient to drop the south white LED have only two white LEDs illuminating from east and west directions. More than three white LEDs may be desired in other applications. Other methods of enabling white-light illumination from multiple directions are also possible. This includes providing a light ring so that illumination comes from all directions (in plane view). This also includes providing mechanical means to physically move a white LED so that it can illuminate the inspection zone from different directions, e.g. by mounting LED on a turret.

In an embodiment, the calculation of molecule concentrations C(x,y) will be most reliable if the set of molecules of interest from Step 1 is complete (in the sense that no other molecules contribute significantly to the measured fluorescence signals). It is also desirable that the number of equations corresponding to FIG. 30 exceeds the number of molecules of interest to that the simultaneous linear equations are over-constrained; a poor quality of fit would provide a warning that the set of molecules of interest is not complete.

An engineer or scientist may find it intuitive and informative to inspect the molecule concentration maps in a visual format. For example, software might display an image of a particle of interest where the computer display (not camera sensor) pixel at location (x,y) has a red sub-pixel value set to the value of $C_{RIBOFLAVIN}(x,y)$, a green sub-pixel value set to the value of $C_{NADH}(x,y)$, and a blue sub-pixel value set to the value of $C_{TRYPTOPHAN}(x,y)$. This corresponds to Step 20. From the information of Step 20, the state of the particles of interest is determined by a skilled human or by automatic software in Step 21.

If artificial intelligence (AI) or neural network algorithms are trained and applied, such machine-learning methods may well directly process the RBG(x,y) image data, thus skipping Steps 19 and 20 and proceeding directly to the particle state determination of Step 21. In other words, in a machine-learning trained-neural-network calculation, the information of Steps 19 and 20 may be present but deeply hidden within the weights of a neural network calculation.

In a specific embodiment, a reference fungal spore in a known state is illuminated using UV light at various spectral characteristics (e.g., different UV wavelengths). The fluorescence from the biomolecules in this reference fungal spore with the known state is captured and recorded as predetermined color characteristics of fluorescent light. These predetermined color characteristics of fluorescent light then function as references to identify a state of a fungal spore at issue.

In a specific embodiment, the fungal spore at issue is illuminated with UV light of a particular spectral characteristic. An image is captured. Concentrations of biomolecules of interest (e.g., riboflavin, NADH, and tryptophan) are estimated from the image. These estimated concentrations (generated from the image taken while the fungal spore at issue was illuminated with UV light of the particular spectral characteristic) are then compared against a subset of the predetermined color characteristics of fluorescent light. Each predetermined color characteristic of fluorescent light in the subset corresponds to UV light of the same particular spectral characteristic under which the image was taken. Upon finding a match between the estimated concentrations and one of the predetermined color characteristics of fluorescent light from the subset, the matching predetermined color characteristic may be cross-referenced to its reference fungal spore of the known state. In embodiment, the predetermined color characteristics of fluorescent light for fluorescent biomolecules of interest corresponds to a fungal spore of a known state having a particular concentration of those fluorescent biomolecules of interest.

In Step 22, the latest particle state information from Step 21 is combined with previous particle state information as well as with information on other variables such as time, temperature, humidity, and fungicide treatments. For example, if when temperature and humidity is favorable to mold infestations and the number of spores detected in a virulent state is increasing, it may be concluded that a mold infestation is imminent. As another example, if after a fungicide treatment, the number of detected spores in a healthy state rapidly decreases to zero, then there is reason to believe that the fungicide treatment was successful and sufficient. On the other hand if a fungicide treatment does not reduce the number of healthy spores, it may be an indication that the mold has developed a resistance to the fungicide in use and a different fungicide is needed. The analysis of data in Step 22 may lead, in Step 23, to alerts or updates being issued to responsible parties. For example, if Step 22 gives reason to believe that an outbreak of mold infestation is imminent, a message to the responsible farmer may be sent recommending an immediate application of fungicide.

Figure 37:
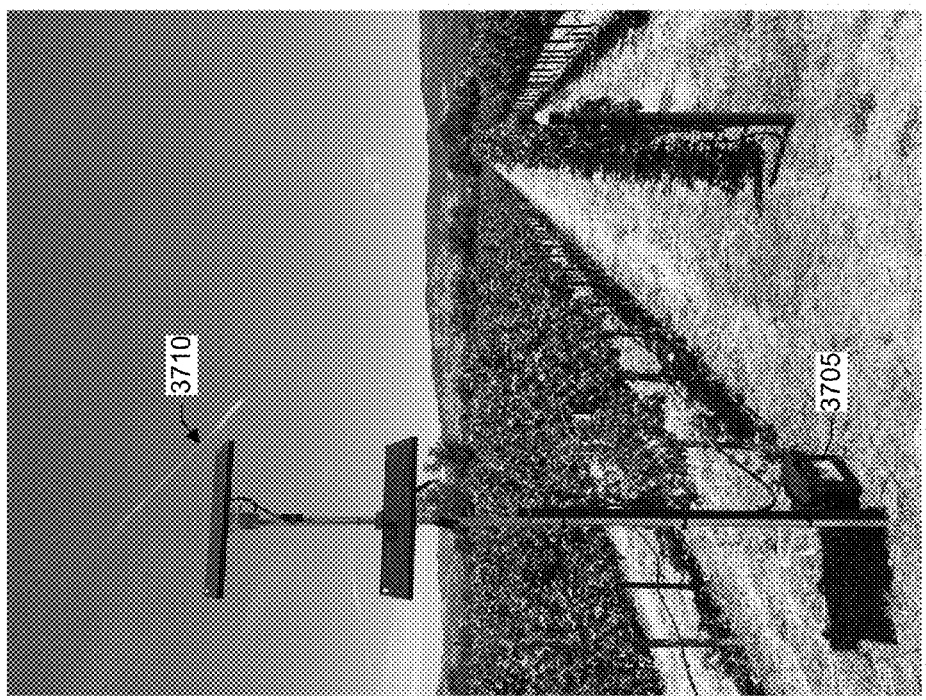
FIG. 37 shows an external solar panel and battery used to power the prototype particle monitor shown in FIG. 36.
Figure 36:
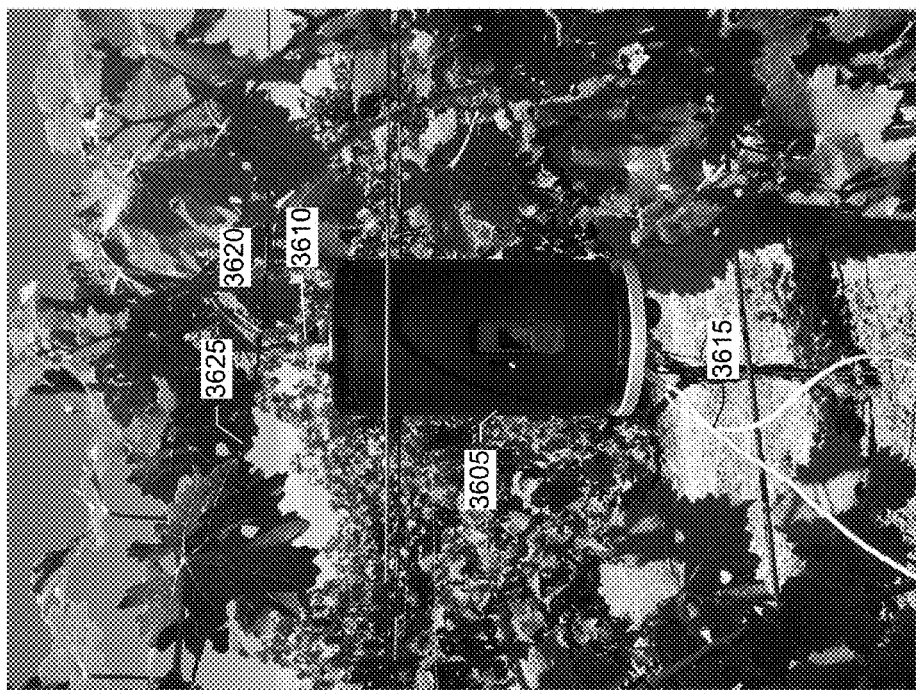
FIG. 36 shows a deployment of a prototype particle monitor in a vineyard.

FIGS. 36-37 show the placement of a particle monitor 3605 (FIG. 36) in a vineyard. In this specific embodiment, the particle monitor is powered by a rechargeable lead-acid battery 3705 (FIG. 37) which in turn is recharged by a set of solar panels 3710.

To prove operability, a prototype of the particle monitor was fully built, deployed within a vineyard, tested, and verified to operate as intended. As shown in FIG. 36, in this specific embodiment, the particle monitor includes an eyelet 3610 connected to a top end of the particle monitor and a set of wires 3615 extending from a bottom end of the particle monitor.

The eyelet allows a hook or carabiner 3620 to pass through so that the particle monitor can be attached to a vineyard wire 3625 and suspended in mid-air. Locating the particle monitor above the ground surface helps to facilitate a good sampling of air and helps to prevent ground dirt, dust, and bugs (e.g., ants) from entering the particle monitor.

An opposite end of the wires is connected to the rechargeable lead-acid battery (FIG. 37) which, as discussed, is recharged by the solar panels. In this specific embodiment, the battery and solar panels are located external to or outside the particle monitor. Locating the battery external to the particle monitor helps to reduce the overall weight of the particle monitor. For example, as shown in FIG. 36, the particle monitor can be hung from an existing vineyard wire without the vineyard wire breaking or experiencing heavy sagging due to the weight of the particle monitor. Locating the battery external to the particle monitor also helps to reduce the need for a lightweight and long-lasting battery; such characteristics generally increase the cost of the battery. The battery can be a relatively large lead-acid battery. Lead-acid batteries are generally less expensive than other battery types such as nickel cadmium (NiCd), nickel-metal hydride (NiMH), lithium ion ($Li^+$ ion), and lithium ion polymer ($Li^+$ ion polymer). Multiple particle monitors (e.g., two or more particle monitors) may be powered by the same external battery.

Locating the solar panels external to the particle monitor allows the solar panels to be placed in a location away from shading so that lots of sunlight can be received. The particle monitor can be placed proximate to or near a grape vine (as shown in FIG. 36). The shading of the particle monitor by the leaves of the grape vine will not detrimentally affect the powering of the particle monitor because the solar panels are located external to the particle monitor.

Diesel Exhaust Monitoring

The above discussion described detection of spores of agricultural interest. Nevertheless, the presented techniques are more broadly applicable. A noteworthy example of an alternate application of the above methods is the detection of soot particles in the air, such as from the exhaust of diesel engines. Due to the impact of diesel exhaust particles on human health, monitoring of soot particles is of particular interest to the field of air pollution monitoring.

Soot particles are formed by incomplete combustion of hydrocarbon fuels. For example, consider combustion of paraffin in a candle flame. Paraffin is composed of hydrocarbons with molecular formulas $C_NH_{2N+2}$ such as $C_{31}H_{64}$. Taking this N=31 example, complete burning with oxygen from the air results in only carbon dioxide and water vapor via the chemical reaction $C_{31}H_{64}+47\ O_2 \rightarrow 31\ CO_2+32\ H_2O$. If a metal spoon is placed well above the candle flame, it remains clean. When the metal spoon is moved down into the top of the candle flame, cooling the flame's gas and halting the chemical reactions before combustion is complete, a black layer of soot is formed on the spoon's surface. Incomplete burning of diesel fuel and other hydrocarbon fuels also generates soot.

The black color of soot correctly suggests that soot particles are carbon rich. Note that for complete combustion, such as $C_{31}H_{64}+47\ O_2 \rightarrow 31\ CO_2+32\ H_2O$, the hydrogen atoms of the hydrocarbon fuel are completely separated from the carbon atoms. During incomplete burning, chemical reactions occur that only partially separate hydrogen and carbon atoms, and only partially combines carbon atoms with oxygen to form carbon dioxide. This results in carbon rich molecules with formulas of the form $C_NH_M$ where M<2N+2. Production of molecules including aromatic rings is favored due to their relative stability. The simplest aromatic hydrocarbon is benzene whose chemical formula is $C_6H_6$ which is indeed carbon rich with 6=M=N<2N+2=14.

FIGS. 38-40 illustrate three representations of the planar benzene molecule $C_6H_6$. With heat and limited oxygen supply, aromatic rings may combine to produce polycyclic aromatic hydrocarbons (PAHs), namely hydrocarbons whose molecules contain multiple aromatic rings. Examples of polycyclic aromatic hydrocarbons (PAHs) are anthracene, triphenylene and coronene with chemical formulas $C_{14}H_{10}$, $C_{18}H_{12}$, and $C_{24}H_{12}$ respectively. FIG. 41 shows an anthracene molecule. FIG. 42 shows a triphenylene molecule. FIG. 43 shows a coronene molecule.

Soot particles contain polycyclic aromatic hydrocarbons (PAHs) of varying degrees of complexity. Many polycyclic aromatic hydrocarbon (PAHs) molecules are toxic. The nature and amount of polycyclic aromatic hydrocarbons (PAHs) in soot particles in the air we breathe is of interest from the perspective of human health.

An important characteristic of airborne soot particles is their size. The soot formed on a metal spoon in a candle flame appears to the human eye to be a continuous and smooth black coating, but in fact is composed of many microscopic soot particles. Diesel exhaust also contains such microscope soot particles. The largest airborne soot particles (including particles that are aggregates of smaller particles) can be as large as several microns in diameter.

However, for diesel particulate matter (DPM), the vast majority of airborne soot particles are of sub-micron size including the 100-nanometer sizes and below. Unlike larger particles, sub-micron sized soot particles travel deep into our lungs and for this reason are of particular concern to the Center for Disease Control's (CDC's) National Institute of Occupational Safety and Health (NIOSH). NIOSH method 5040 for monitoring airborne diesel particular matter (PDM), which is incorporated by reference, is designed to detect sub-micron sized particles. For example, the NIOSH 5040 document, available at the CDC website and incorporated by reference, includes the following quote concerning the removal of micron-sized particles from the particulates to be measured: " . . . For measurement of diesel-source EC in coal mines, a cyclone and impactor with submicrometer cutpoint are required to minimize collection of coal dust. A cyclone and/or impactor may be necessary in other workplaces . . . ". The sub-micron sizes of diesel exhaust soot particles of interest are much smaller than the multiple-micron sizes of mold spores and pollen grains.

Given the small sizes of airborne soot particles of interest, it would at first appear that a microscope-based device would be of little value in the field of diesel particulate matter (PDM) monitoring. The size of a 100-nanometer soot particle is much smaller than the wavelengths of visible light. (Visible light wavelengths range from 400 nanometers at the violet to 700 nanometers for red.) Optical microscopes cannot image objects that are small compared to the wavelength of light. Morphological features of such small soot particles are far beyond the resolution of optical microscopes. Electron microscopes can image soot particles with high resolution, but with high cost and complex sample preparation are not amenable to low-cost real-time monitoring. Small soot particles of interest are difficult to detect at all within an optical image, even as a small blurry dot. Per pessimistic conventional thinking, optical microscope-based devices have little to offer regarding the needs of diesel particulate matter (DPM) monitoring.

Applicant has identified a solution that goes contrary to the conventional thinking. Applicant has observed that the NIOSH 5040 method for diesel particulate matter (DPM) monitoring is far from perfect. It measures the total mass per unit air volume of ultrafine diesel particulate matter (DPM), but provides no information on the particle size distribution. Two air samples with exactly the same amount of diesel particular matter (DPM) in units of micrograms per liter, but with different particle size distributions, may well have very different degrees of impact on human health.

Furthermore, even with the same micrograms per liter and the same particle size distributions, two air samples may still have different impacts on human health if their chemical compositions differ. For example, soot particles in one air sample may contain more toxic polycyclic aromatic hydrocarbons (PAHs) than the other. There is a need to complement the micrograms-per-liter measurement of airborne diesel particulate matter (DPM), such as provided by NIOSH 5040 methods, with an ability to monitor other characteristics of diesel particulate matter (PDM) such as particle size distribution and polycyclic aromatic hydrocarbon (PAH) content.

Applicant has realized that an examination of the tail of particle size distribution can be useful in diesel exhaust monitoring. For soot particles that are large enough to be imaged by an optical microscope, optical images provide a good means via color and morphology to differentiate between larger soot particles and other particles of similar size. Hence the upper end of the soot particle distribution can be measured even in the presence of background particles of similar sizes. This is not true for monitors based on the NIOSH 5040 method. However, as discussed above, it is understood that such larger soot particles that can be effectively imaged in an optical microscope are not in the size range of greatest interest to human health. Nevertheless, surprisingly, and as described below, monitoring of large soot particles does nevertheless provide information of interest.

Figure 44:
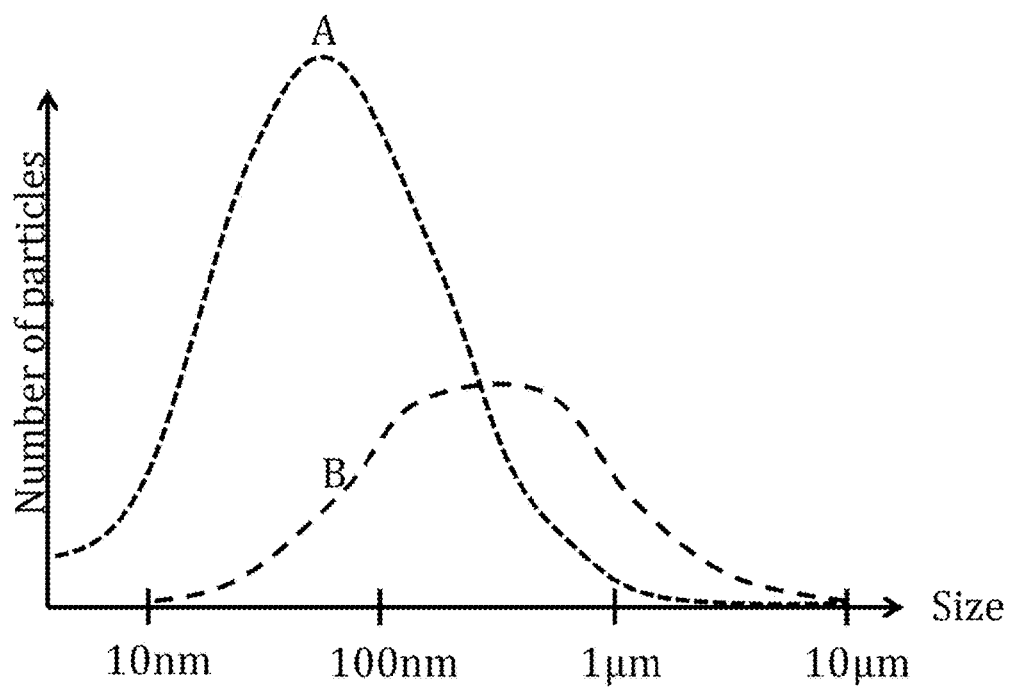
FIG. 44 shows a plot of two size distributions of diesel particulate matter (DPM).

The plot in FIG. 44 illustrates two size distributions of diesel particulate matter (DPM). Distribution A has on average smaller particles sizes and a larger total number of particles while distribution B has on average larger particle sizes and a smaller total number of particles. Consider the case where both distributions correspond to exactly the same mass per liter of air as measured by the NIOSH 5040 method.

Distribution A will be more damaging to human health as it contains more particles making it deep into our lungs and provides a larger total particulate surface area for exposing lung tissue to toxic polycyclic aromatic hydrocarbons (PAHs). Now consider the larger-size tails of the two distributions, such as the large-size tails above 1 micron in size. Distribution B has a much bigger tail into micron sizes than distribution A, something that can be observed with an optical-microscope based monitoring device. By measuring diesel particulate matter (DPM) with both NIOSH-5040 methodology and simultaneously with optical-microscope based devices, useful particulate-size-distribution information is provided that is relevant to assessing the effects of the diesel particulate matter (DPM) on human health.

Figure 45:
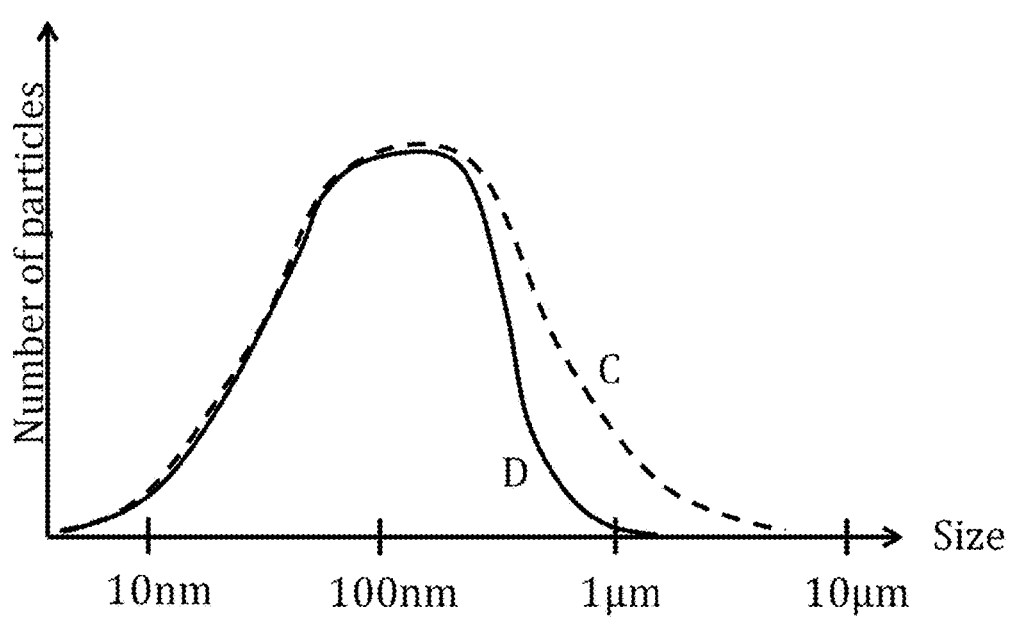
FIG. 45 shows another plot of two size distributions of DPM.

Larger particles settle out of air faster than smaller particles. For a given source of diesel particulate matter (DPM), the distribution of particle sizes will change over time. For example, on a calm day, the micron-sized particles will settle out of the air faster than the sub-micron-sized particles. This is illustrated FIG. 45 in which the micron sized particles in the source distribution C is missing from the size distribution D of the polluted air after it has separated from the source in time and distance. The presence or lack of the above-one-micron tail of the size distribution reveals clues about the distance of the source from the monitoring location. The above-one-micron tail of the size distribution, even if empty, provides useful additional information regarding diesel particulate matter (DPM) that is not available from NIOSH-5040 method measurements alone. Depending on the application, the optimal choice of threshold size for the large-size distribution tail may vary from a value of one micron, but the principles remain the same.

More generally, monitoring of the above-one-micron tail of the diesel particulate matter (DPM) distribution provide additional independent information that may be used in various ways by resourceful air pollution scientists and technicians. Perhaps an appropriate analogy here is between the tip of an iceberg and the above-one-micron tail of diesel particulate matter (DPM), and between sub-micron distribution of diesel particulate matter (DPM) and the undersea portions of icebergs. It is the undersea portions of icebergs that sink ships. Nevertheless it is useful for sailors to look for tips of icebergs rising above the surface of the sea. Likewise it is the sub-micron distribution of diesel particulate matter (DPM) that is most damaging to human health, but it may nevertheless useful to monitor the above-one-micron tail of diesel particulate matter (DPM) distributions.

Probing PAH Toxicity with UV Fluorescence

Under UV illumination, some polycyclic aromatic hydrocarbons (PAHs) fluoresce. For example, this is true for the above-mentioned anthracene ($C_{14}H_{10}$), triphenylene ($C_{18}H_{12}$) and coronene ($C_{24}H_{12}$). For example, anthracene fluoresces blue under UV light. Thus soot particles may include UV fluorescent molecules analogous to the flavin, NADH and tryptophan molecules of biological particles discussed above. The molecular structures of flavin, NADH and tryptophan are shown FIGS. 46, 47, and 48, respectively.

Like the polycyclic aromatic hydrocarbons (PAHs) anthracene, triphenylene and coronene, these three biological molecules fluoresce visible light under UV illumination due to the presence of polycyclic aromatic rings. The techniques described above in connection with FIGS. 29, 30 and 31 can equally well be applied to the analysis of polycyclic aromatic hydrocarbons (PAHs) content of soot particles. Data related to the polycyclic aromatic hydrocarbon (PAH) content of soot particles may be relevant to the assessment of the chemical toxicity of diesel particulate matter (DPM).

The polycyclic aromatic rings of the three biological molecules in FIGS. 46-48 differ chemically from the polycyclic aromatic rings of polycyclic aromatic hydrocarbons (PAHs). In the latter case, the rings contain only carbon atoms, while for the biological molecules rings also include nitrogen atoms. Given this chemical difference between fluorescing molecules in soot particles and biological particles (like spores and pollen), the two different types of particles are expected to have distinct UV fluorescence properties. These differences can be exploited by taking advantage of the three color images of RGB camera sensors as well as the option of the devices described above to use UV illumination of one or more wavelengths.

During the course of field studies, it was observed that dusting a crop with fungicide dusting resulted in detected particles having strong fluorescence under 340 nm UV illumination as well as having sufficient sizes to be imaged by optical microscopy. In light of the above discussion, and that fact that many fungicides include aromatic rings within their molecular structures, similar observations may be for dustings or sprays of a number of fungicides. Examples of fungicides with aromatic rings of various sorts include Metalaxyl, Bupirimate, Carendazim, Boscalid, Azoxystrobin, Cyprodinil, Proquinazid, Quinoxyfen, Iprodione, Spiroxamine, Fenhexamid, Dimehtomorph, Chlorothalonil and Metrafenone. More generally, a number pesticides ("pesticides" include herbicides and insecticides as well as fungicides) may well have strong UV fluorescence signatures.

UV Fluorescence of Sub-Micron Soot Particles

Distinct color characteristics of soot particle UV fluorescence may enable detecting sub-micron soot particles that would otherwise be undetected by an optical-microscope based system. Consider, as an example, that the adhesive surface of the tape described above collects sub-micron soot particles in addition to biological particles like pollen and spores as well as inorganic dust. It may well be impossible or difficult to confidently recognize sub-micron soot particles in RGB camera sensor images under white light illumination.

However, a general fluorescent glow of the adhesive coated tape under UV illumination may provide a signature and measure of a dusting of sub-micron soot particles. In particular, a fluorescent glow might be identified as having the fluorescent color characteristics of the soot particles' polycyclic aromatic hydrocarbons (PAHs). The fact that inorganic dust does not fluoresce eliminates it as a potential background. The ability of the above-described devices to image and recognize biological particles is also an advantage here. Any camera-sensor pixels within images of pollen, spores and other biological particles can be removed before analysis of the color of any remaining fluorescent glow; this is a powerful way to minimize UV fluorescence background from biological particles.

As just noted, an ability to recognize pollen, spores and other biological particles within RBG camera sensor images enables powerful background-subtraction methods when seeking optical signals from another source of interest such as diesel particulate matter. Both morphology and color, including UV fluorescence excitation and emission wavelength characteristics, provide techniques to recognize pollen, spores and other biological particles.

The simplest morphological feature is size. Pollen and spores tend to be many microns while most diesel particulate matters are submicron in size. That is, pollen and spores tend to extend over many pixels in RGB camera sensor images while diesel particles generally do not. Furthermore, pollen grains or mold spores are typically large enough to reveal distinctive shapes in optical images.

Color is another differentiator. Soot particles tend to be opaque and black while pollen and spores tend to be more translucent. In general, any image processing and image recognition techniques that maybe used to identify pollen, spores and other biological particles when they are objects of interest may also be used to identify pollen, spores and other biological particles when they are backgrounds to be removed from analysis while pursuing other optical signals of interest.

As an analogy here, consider a stargazer looking at light from the Milky Way. The human eyes and mind are able to see past bright foreground stars and see the dim Milky Way behind it. However, if one attempted to detect the Milky Way by pointing a light meter in the general direction of the Milky Way, the dim light from the Milky Way would be lost in the background of the bright foreground stars. Likewise, UV fluorescence detection without camera-sensor imaging may leave an unusable sub-micron soot particle signal that is swamped by biological particle fluorescence. However, like a stargazer's eyes and mind can ignore foreground starts, the particle monitors described above have the ability to separate bright fluorescence from biological particles from a possibly much dimmer fluorescence signal from many small soot particles captured on the adhesive surface.

Combining Scanit & NIOSH 5040 Detectors

The methods and apparatuses described above may be combined with other particle detection methods such as those described in the NIOSH 5040 method for airborne diesel soot detection. A NIOSH 5040 method based detector may include a transparent or translucent air filter through which sampled air passes after larger particles have been removed. As soot collects on such an air filter, it darkens and becomes less transparent or translucent. A light source may be placed on one side of the air filter and a light detector placed on the other side of the air filter. A reduction in light transmission through the air filter provides a technique to estimate the micrograms of diesel soot per liter of sampled air. Such a methodology may be combined with the methods and apparatuses described above.

Figure 51:
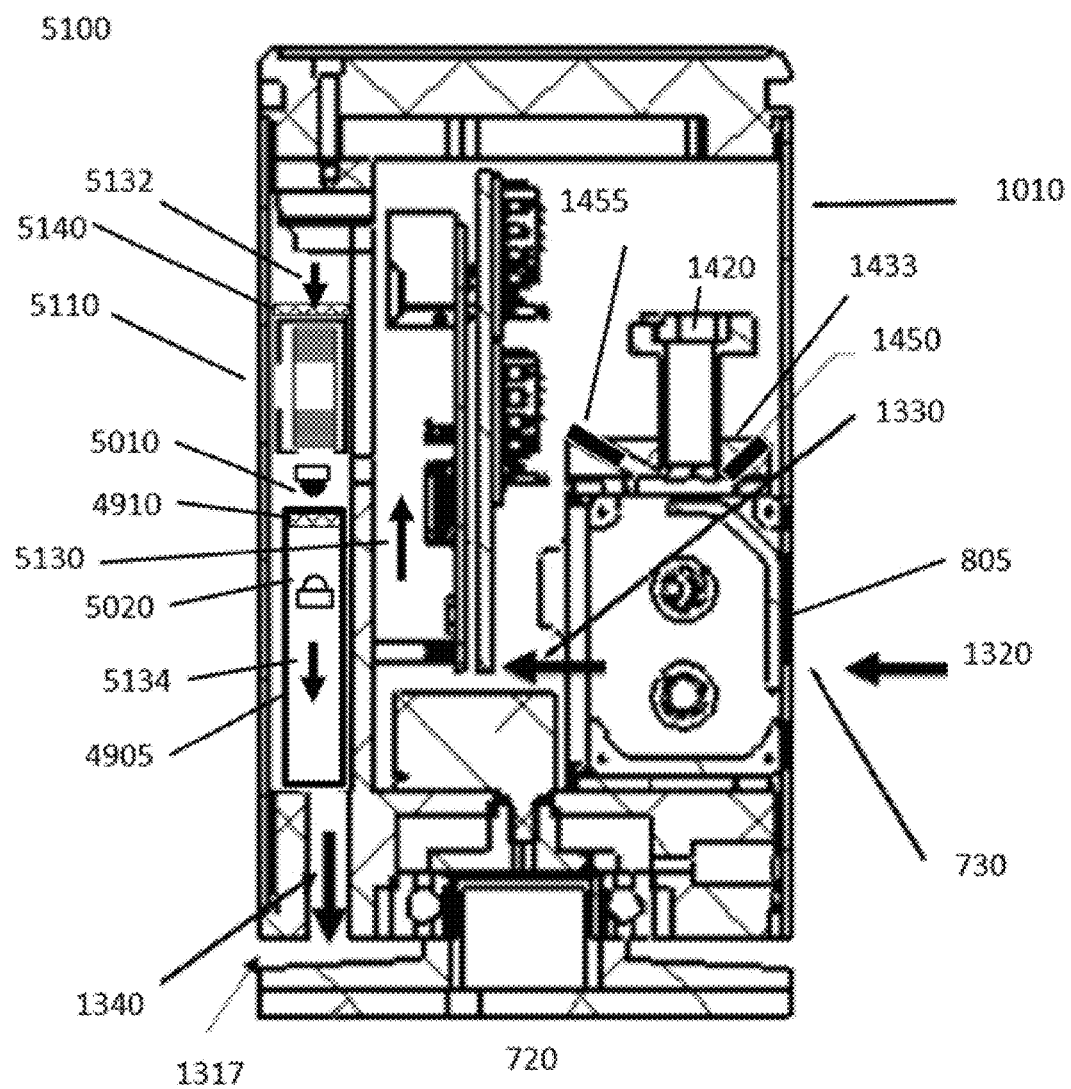
FIG. 51 shows a section of a particular monitoring device for airborne diesel soot detection according to a specific embodiment.

For example, a particle-monitoring device 5100 of FIG. 51 is such a modification of the particle-monitoring device 700 shown in the same vertical cross-sectional view as FIG. 13. Blower 5110 drives airflow through the particle-monitoring device 5100 as indicated by arrows 1320, 1330, 5130, 5132, 5134, and 1340.

Before reaching gap 1317, this airflow is intercepted by transparent or translucent air filter 4910. Translucent air filter 4910 is a sufficiently fine filter to capture any diesel particulate matter in the air. This translucent air filter 4910 is mounted within a removable air-filter cartridge 4905. (For clarity, sliding doors and other mechanics for inserting or removing air-filter cartridge 4905 are not shown. Also for clarity, not shown are various gaskets and other airflow barriers needed to avoid undesired airflow paths.)

In some embodiments, the air-filter cartridge 4905 may be removed and shipped to a lab for analysis while a replacement fresh cartridge may be inserted into the particle-monitoring device 5100.

In other embodiments, the accumulation of any diesel particulate matter on air filter 4910 is optically monitored in situ. For this purpose, particle-monitoring device 5100 may be optionally provided with filter light source 5010 and filter light detector 5020. For clarity, mounting and electrical connections of the filter light source 5010 and the filter light detector 5020 to the particle-monitoring device 5100 are not shown.

Filter light source 5010 may be a visible light LED and filter light detector may be a phototransistor. Alternatively, filter light source 5010 and/or filter light detector 5020 may be ends of optical fibers that transmit light to or from electro-optical components on a circuit board elsewhere within particle-monitoring device 5100. Reduction of the signal from the filter light detector 5020 provides a measure of the darkening of the translucent air filter 4910 due to accumulation of diesel particulate matter or other sooty material in the air. Such in situ optical measurements may be in addition to, or instead of, laboratory analysis of accumulated diesel particulate matter or other types of soot.

In yet other embodiments, air-filter cartridge 4905 and particle-media cartridge 805 are designed to be sufficiently similar in mechanical design and form factor so that particle-media cartridge 805 can be removed from its location shown in FIG. 51 and replaced with air-filter cartridge 4905, and it so doing placing translucent air filter 4910 within the field of view of the optical system of RGB camera sensor 1420. This enables two-dimensional image analysis of matter accumulated in the air filter 4910. If opaque objects unrelated to diesel particulate matter are observed in images from RGB camera sensor 1420, then appropriate corrections may be made to previous optical transmission measurements from filter light source 5010 to filter light detector 5020.

If the illumination system associated used with RGB camera sensor 1420 includes UV light sources, the fluorescence properties of material collected by the air filter 4910 may be measured. This is of interest as a probe of the presence of toxic compounds within any accumulated diesel particulate matter. For example, UV fluorescence properties of accumulated diesel particulate matter may provide a technique to detect toxic compounds such as anthracene, triphenylene, coronene, and others.

Figure 49:
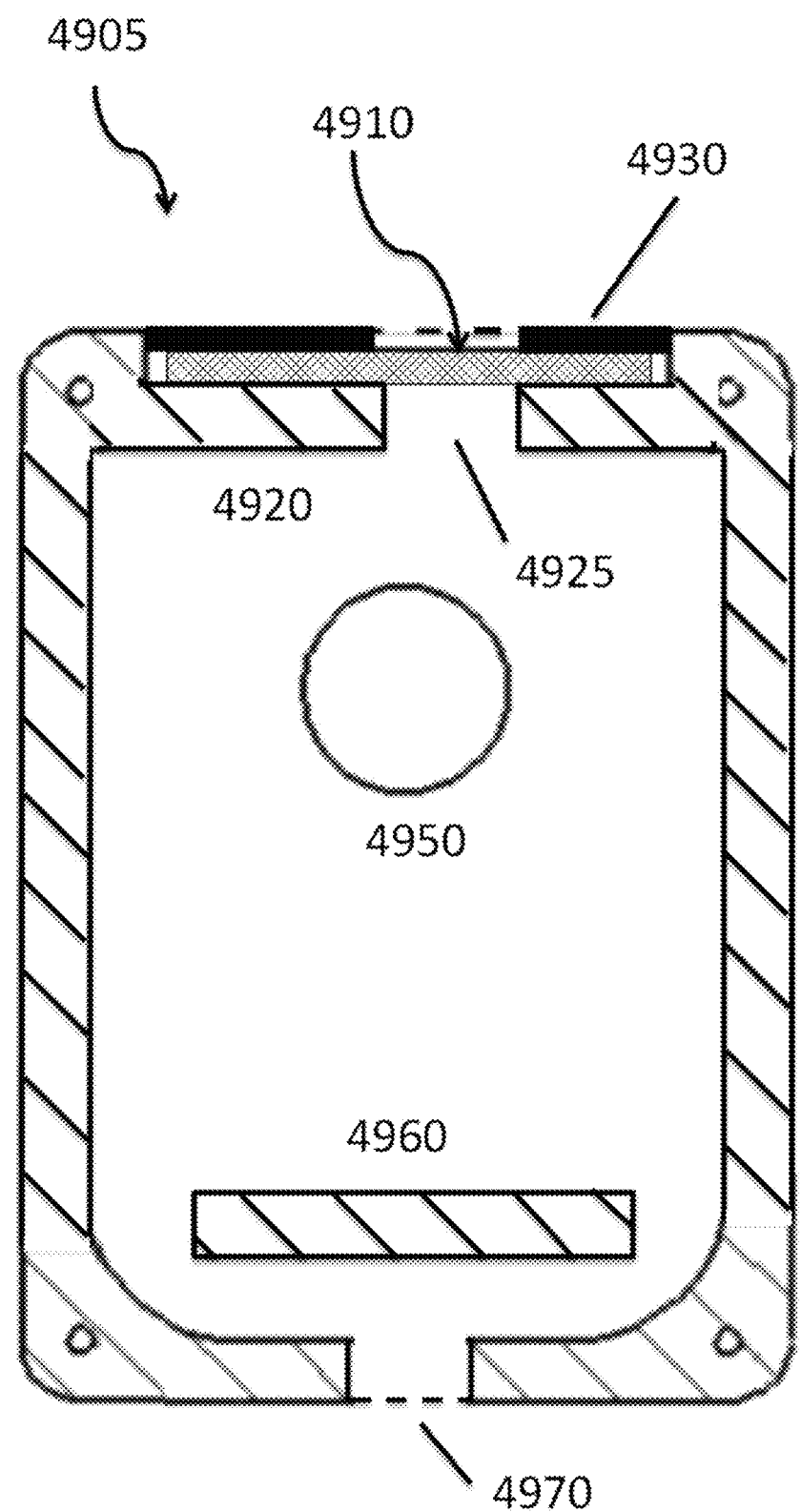
FIG. 49 shows a section of an air filter cartridge according to a specific embodiment.

FIG. 49 illustrates an air-filter cartridge 4905 designed for insertion into the slot that normally holds a particle-media cartridge 805 as well as for insertion into the air-filter cartridge 4905 location shown in FIG. 51. FIG. 49 shows a cross-sectional view similar to that of FIG. 9. Air filter support 4920 contains a hole 4925 through which air may flow after passing through translucent air filter 4910. The translucent air filter 4910 is held in place by a retaining structure 4930.

Retaining structure 4930 may be of any design that services its purpose, including a plastic piece held in place by a tight friction fit, or a slightly concave piece of thin sheet metal. Items 4950, 4960 and 4970 are explained with the aid of FIG. 50.

Figure 50:
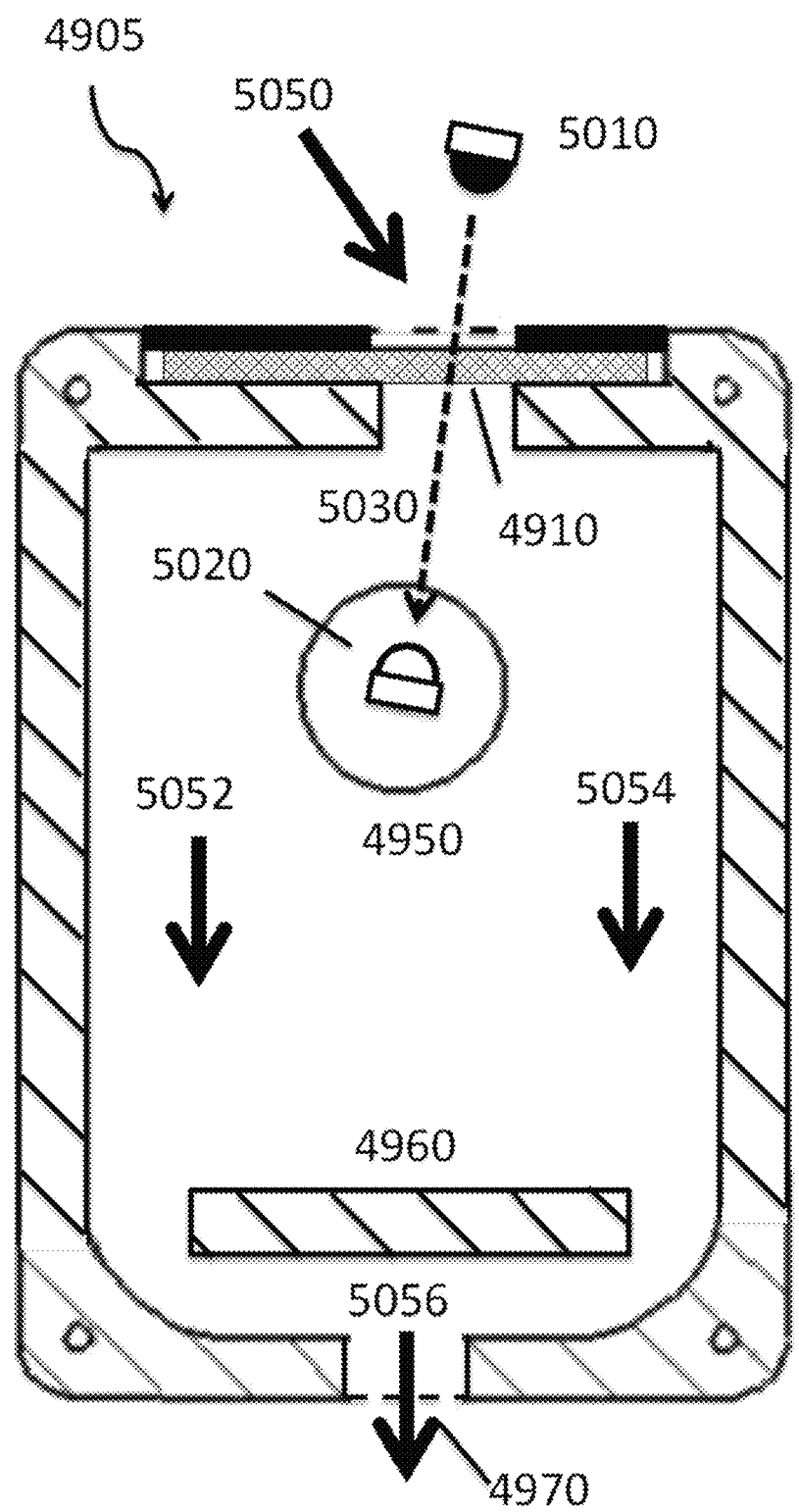
FIG. 50 shows a section of another air filter cartridge according to another specific embodiment.

FIG. 50 is a modification of FIG. 49 with additions illustrating airflow and optical components. When inserted into particle-monitoring device 5100 as shown in FIG. 51, air flows through air-filter cartridge 4905. Air leaving blower 5110 and approaching air-filter cartridge 4905 is indicated by arrow 5050. Air that flows through air-filter cartridge 4905, as illustrated by arrows 5052 and 5054, leaves the cartridge through exit hole 4970, as indicated by arrow 5056.

If it is desired to shield optical components from background light entering through exit hole 4970, an optical baffle 4960 may be included. The optical-detector hole 4950 of air-filter cartridge 4905 is similar in geometry to gear-shaft hole 850 of particle-media cartridge 805 (see FIG. 8). Optical-detector hole 4950 avoids mechanical interference with the gear shaft when air-filter cartridge 4905 is inserted into the slot normally occupied by particle-media cartridge 805. The optical-detector hole 4950 serves a second purpose. It allows filter light detector 5020 to be located below air filter 4910 within the volume of the air-filter cartridge 4905, and yet be mechanically attached and electrically connected to the particle-monitoring device 5100, and not mechanically attached to or mechanically interfering with the body of air-filter cartridge 4905.

Filter light source 5010 is also mechanically attached and electrically connected to the particle-monitoring device 5100. Dashed arrow 5030 illustrates a light path from filter light source 5010 through air filter 4910 to the filter light detector 5020. Any diesel particulate matter within air flowing along arrow 5050 will accumulate on air filter 4910 making it darker and reducing the light intensity reaching filter light detector 5020. In this manner measurements based on the NIOSH 5040 method may be performed in real time.

Returning to FIG. 51, optionally, particle-monitoring device 5100 may include a course air filter 5140 to reduce the rate that larger particles, such as those not related to diesel particular matter, reach air filter 4910. Instead, or in addition, a cyclone impactor or other type of impactor (not shown) may be inserted in the airflow upstream of the air filter 4910 to further prevent any larger particles reaching air filter 4910.

The above discussion in connection with FIGS. 49, 50 and 51 demonstrate that it is possible to combine RGB camera sensor based measurement methods and NIOSH 5040 methods in a way that combines their respective strengths.

Fungicide (Pesticide) Particle Detection

Returning to agricultural applications, it is of interest to be able to detect and recognize particles of pesticide sprays or dustings. As noted above, such pesticide particles may well be sufficiently large to be imaged in RGB camera sensor 1420 and also have strong UV fluorescence characteristics. Thus such pesticide particles fit nicely within the detection capabilities of the methods and apparatuses described above. Such pesticide particles may be distinguished from other types of particles based on morphological characteristics, color characteristics under visible light illumination as well as fluorescence color characteristics under illumination by one or more UV light sources.

Detection and recognition of particles from pesticide sprays or dustings are of interest for a number of purposes. In cases where pesticide particles are a potential background for the detection of other particles of interest, it is desirable to recognize pesticide particles so that they can be removed from the analysis of images containing other particles of interest. In other cases, the pesticide particles are themselves of interest. For example, for farm worker safety, after application of a dusting of fungicide, it may be desirable to determine when the fungicide has completely settled out of the ambient air and hence it is safe for a farm worker to re-enter the area. In another example, it may be of interest for a remote farm manager to know which field was sprayed when with which pesticide. In some cases the farm manager may appreciate receiving such information provided by a monitor in the field as well as through communications with farmworkers. In some cases the "farm workers" may be automatic robotic equipment.

Furthermore, it may be of interest to know the details of how the density of pesticide particles in ambient air decays with time. For example, it may be good to know if the amount of pesticide particles in the air drops rapidly, perhaps because a sudden breeze blew the pesticide spray away from the intended field. Finally, we note that much useful information may be provided by correlations, or instead or additionally, anti-correlations, between the detection of fungicide or pesticide particles and measured pathogenic fungal spores or other pests.

Sooty Pollen Grains

The different color signatures of polycyclic aromatic hydrocarbons (PAHs) in soot particles and fluorescing molecules in biological particles makes possible another technique. As pollen and spore particles are transported in air containing diesel exhaust pollution, their surfaces may make contact with, and adhere to, soot particles. This leads to techniques of using pollen grains being transported by the wind as probes of diesel particulate matter (DPM) in the air. Larger pollen grains may be best suited for this purpose as they are easily imaged and recognized in an optical-microscope based devices. Furthermore, large pollen grains may more efficiently collect soot from ambient air as they respond to both settling from gravity and centrifugal effects from air turbulence with larger relative velocities with respect to neighboring sub-micron soot particles.

Greater velocity with respect to small soot particles leads to more larger pollen and spore particles encountering more small soot particles. A sooty pollen grain, when captured and imaged, will have UV fluorescence with color signatures of biological molecules from its interior, but additional UV fluorescence due to diesel soot particles on its surface. The presence of surface diesel particles on the surface of a biological particle may be determined from the color signatures of diesel particulate matter (DPM). Note that the species of pollen, and the location of plants of the species within the local geography, provide clues regarding the path of the sooty pollen grain from its source to the monitor, and hence clues regarding the location(s) where the pollen grain encountered soot particles.

Smoke & First Responders

The above described methods and apparatuses for collecting useful information about diesel soot in ambient air also applies to soot and smoke encountered by first responders to fire emergencies. Again, particle size distribution information and UV fluorescence characteristics may provide useful clues regarding the risk to human health posed by smoke and soot in the ambient air. Also, on the theme of monitoring the health risks of ambient air, it may be of interest to detect of particles in exhaust from military use of ammunition and propellants.

FIG. 52 is a simplified block diagram of a distributed computer network 5200 that may be used in a specific embodiment of a system for airborne particle collection, detection and recognition. Computer network 5200 includes a number of client systems 5213, 5216, and 5219, and a server system 5222 coupled to a communication network 5224 via a plurality of communication links 5228. There may be any number of clients and servers in a system. Communication network 5224 provides a mechanism for allowing the various components of distributed network 5200 to communicate and exchange information with each other.

Communication network 5224 may itself be comprised of many interconnected computer systems and communication links. Communication links 5228 may be hardwire links, optical links, satellite or other wireless communications links, wave propagation links, or any other mechanisms for communication of information. Various communication protocols may be used to facilitate communication between the various systems shown in FIG. 52. These communication protocols may include TCP/IP, HTTP protocols, wireless application protocol (WAP), vendor-specific protocols, customized protocols, and others. While in one embodiment, communication network 5224 is the Internet, in other embodiments, communication network 5224 may be any suitable communication network including a local area network (LAN), a wide area network (WAN), a wireless network, an intranet, a private network, a public network, a switched network, and combinations of these, and the like.

Figure 52:
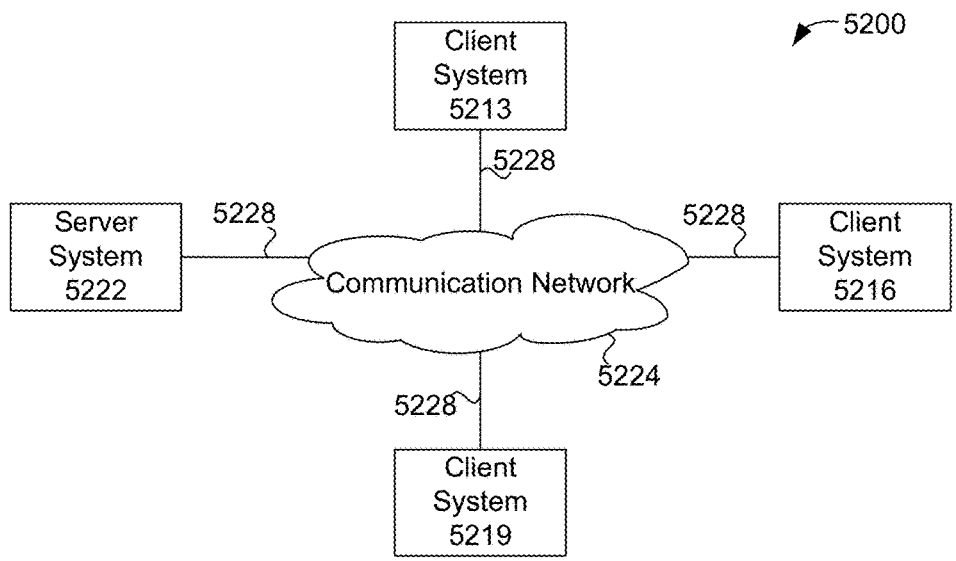
FIG. 52 shows a block diagram of a client-server system and network in which an embodiment of the system may be implemented.

Distributed computer network 5200 in FIG. 52 is merely illustrative of an embodiment and is not intended to limit the scope of the embodiment as recited in the claims. One of ordinary skill in the art would recognize other variations, modifications, and alternatives. For example, more than one server system 5222 may be connected to communication network 5224. As another example, a number of client systems 5213, 5216, and 5219 may be coupled to communication network 5224 via an access provider (not shown) or via some other server system.

Client systems 5213, 5216, and 5219 enable users to access and query information stored by server system 5222. In a specific embodiment, a "Web browser" application executing on a client system enables users to select, access, retrieve, or query information stored by server system 5222. Examples of web browsers include the Internet Explorer® and Edge® browser programs provided by Microsoft® Corporation, Chrome® browser provided by Google®, and the Firefox® browser provided by Mozilla® Foundation, and others. In another specific embodiment, an iOS App or an Android® App on a client tablet enables users to select, access, retrieve, or query information stored by server system 5222. Access to the system can be through a mobile application program or app that is separate from a browser.

A computer-implemented or computer-executable version of the system may be embodied using, stored on, or associated with computer-readable medium or non-transitory computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present system may be stored or reside in RAM or cache memory, or on a mass storage device. The source, executable code, or both of the software may also be stored or reside on a mass storage device (e.g., hard disk, magnetic disk, tape, or CD-ROM). As a further example, code may be transmitted via wires, radio waves, or through a network such as the Internet.

A client computer can be a smartphone, smartwatch, tablet computer, laptop, wearable device or computer (e.g., Google Glass), body-borne computer, or desktop.

Figure 53:
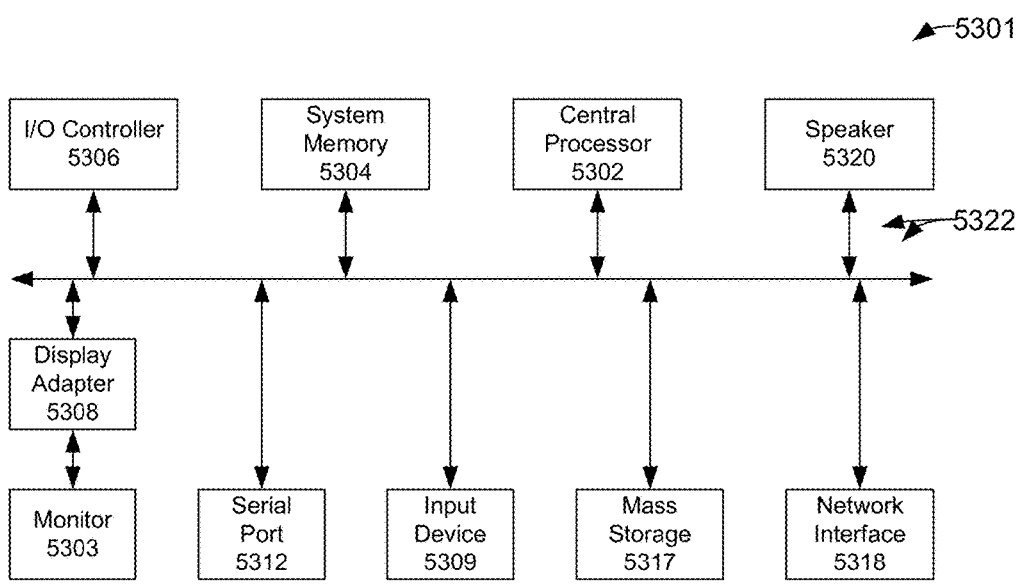
FIG. 53 shows a system block diagram of a client or server computer system shown in FIG. 52.

FIG. 53 shows a system block diagram of computer system 5301. Computer system 5301 includes monitor 5303, input device (e.g., keyboard, microphone, or camera) 5309, and mass storage devices 5317. Computer system 5301 further includes subsystems such as central processor 5302, system memory 5304, input/output (I/O) controller 5306, display adapter 5308, serial or universal serial bus (USB) port 5312, network interface 5318, and speaker 5320. In an embodiment, a computer system includes additional or fewer subsystems. For example, a computer system could include more than one processor 5302 (i.e., a multiprocessor system) or a system may include a cache memory.

Arrows such as 5322 represent the system bus architecture of computer system 5301. However, these arrows are illustrative of any interconnection scheme serving to link the subsystems. For example, speaker 5320 could be connected to the other subsystems through a port or have an internal direct connection to central processor 5302. The processor may include multiple processors or a multicore processor, which may permit parallel processing of information. Computer system 5301 shown in FIG. 53 is but an example of a suitable computer system. Other configurations of subsystems suitable for use will be readily apparent to one of ordinary skill in the art.

Computer software products may be written in any of various suitable programming languages, such as C, C++, C#, Pascal, Fortran, Perl, Matlab® (from MathWorks), SAS, SPSS, JavaScript®, AJAX, Java®, SQL, and XQuery (a query language that is designed to process data from XML files or any data source that can be viewed as XML, HTML, or both). The computer software product may be an independent application with data input and data display modules. Alternatively, the computer software products may be classes that may be instantiated as distributed objects. The computer software products may also be component software such as Java Beans® (from Oracle Corporation) or Enterprise Java Beans® (EJB from Oracle Corporation). In a specific embodiment, a computer program product is provided that stores instructions such as computer code to program a computer to perform any of the processes or techniques described.

An operating system for the system may be iOS by Apple®, Inc., Android by Google®, one of the Microsoft Windows® family of operating systems (e.g., Windows NT®, Windows 2000®, Windows XP®, Windows XP® x64 Edition, Windows Vista®, Windows 7®, Windows CE®, Windows Mobile®, Windows 8, Windows 10), Linux, HP-UX, UNIX, Sun OS®, Solaris®, Mac OS X®, Alpha OS®, AIX, IRIX32, or IRIX64. Other operating systems may be used. Microsoft Windows® is a trademark of Microsoft® Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of the system using a wireless network using a protocol such as Wi-Fi (IEEE standards 802.11, 802.11a, 802.11b, 802.11e, 802.11g, 802.11i, and 802.11n, just to name a few examples). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

In a specific embodiment, a method for determining a state of a fungal spore includes: directing a flow of air comprising the fungal spore to a collection cartridge; trapping the fungal spore within the collection cartridge; illuminating the fungal spore in the collection cartridge with light; while the fungal spore is illuminated with the light, capturing a first image of the fungal spore; analyzing the first image to identify an outline of the fungal spore; illuminating the fungal spore in the collection cartridge with ultraviolet (UV) light; while the fungal spore is illuminated with the UV light, capturing a second image of the fungal spore; measuring from the second image a degree of fluorescence within the outline of the fungal spore; and based on the degree of fluorescence, determining the state of the fungal spore.

Determining the state of the fungal spore may include determining whether the fungal spore is in a virulent state or a sterile state. Determining the state of the fungal spore may include comparing the degree of fluorescence to a predetermined threshold value; if the degree of fluorescence is above the predetermined value, determining that the fungal spore is in a first state; and if the degree of fluorescence is below the predetermined value, determining that the fungal spore is in a second state, different from the first state.

In a specific embodiment, the method further includes inferring concentrations of biomolecules of interest within the fungal spore by correlating a value of a pixel located at coordinates (x,y) on the image to a concentration of a biomolecule of interest as being at the coordinates (x,y) on the image; obtaining reference information comprising fluorescent properties of the biomolecules of interest associated with known states of the fungal spore; obtaining camera sensor information of a camera sensor used to capture the second image, the camera sensor information comprising color sensitivity characteristics of the camera sensor; and processing the inferred concentrations of the biomolecules of interest with the fluorescent properties reference information and camera sensor information to determine the state of the fungal spore.

The method may include storing in a log file a timestamp indicating when the fungal spore was trapped, and the determined state of the fungal spore, wherein the determined state comprises one of a virulent state or a sterile state.

In an embodiment, the collection cartridge includes a tape upon which the fungal spore is trapped and the method includes: after the trapping the fungal spore within the collection cartridge, advancing the tape upon which the fungal spore is trapped to a position underneath first and second light sources, wherein the first light source comprises the light, the second light source comprises the UV light, and wherein during the illuminating the fungal spore with the light and illuminating the fungal spore with UV light, the tape remains in the same position.

In an embodiment, the method includes using an integrated camera sensor chip package to capturing the first image of the fungal spore, and the second image of the fungal spore, wherein the integrated camera sensor chip package comprises a light-sensing pixel sensor array, analog drive and readout circuitry, analog-to-digital conversion circuitry, digital image processing circuitry, and digital communications circuitry.

In another specific embodiment, there is a method for determining a state of a fungal spore comprising: defining a plurality of types of fluorescent biomolecules of interest within the fungal spore; storing a first plurality of predetermined color characteristics of fluorescent light for each type of fluorescent biomolecules of interest, each predetermined color characteristic of the first plurality of predetermined color characteristics corresponding to excitement of a respective fluorescent biomolecule of interest under ultraviolet (UV) light having first spectral characteristics; storing a second plurality of predetermined color characteristics of fluorescent light for each type of fluorescent biomolecules of interest, each predetermined color characteristic of the second plurality of predetermined color characteristics corresponding to excitement of a respective fluorescent biomolecule of interest under UV light having second spectral characteristics, different from the first spectral characteristics; storing a third plurality of predetermined color characteristics of fluorescent light for each type of fluorescent biomolecules of interest, each predetermined color characteristic of the third plurality of predetermined color characteristics corresponding to excitement of a respective fluorescent biomolecule of interest under UV light having third spectral characteristics, different from the first and second spectral characteristics; directing a flow of air comprising the fungal spore to a collection cartridge; trapping the fungal spore within the collection cartridge; illuminating the fungal spore in the collection cartridge with light; while the fungal spore is illuminated with the light, capturing a first two-dimensional color image of the fungal spore; analyzing the first two-dimensional color image to identify an outline of the fungal spore, the outline of the fungal spore being defined by a set of image pixels receiving light from the fungal spore; illuminating the fungal spore in the collection cartridge with UV light of the first spectral characteristics; while the fungal spore is illuminated with the UV light of the first spectral characteristics, capturing a second color image of the fungal spore; measuring from the second color image a degree and color of fluorescence for each pixel within the outline of the fungal spore; illuminating the fungal spore in the collection cartridge with ultraviolet (UV) light of the second spectral characteristics; while the fungal spore is illuminated with the UV light of the second spectral characteristics, capturing a third color image of the fungal spore; measuring from the third color image a degree and color of fluorescence for each pixel within the outline of the fungal spore; illuminating the fungal spore in the collection cartridge with UV light of the third spectral characteristics; while the fungal spore is illuminated with the UV light of the third spectral characteristics, capturing a fourth color image of the fungal spore; measuring from the fourth color image a degree and color of fluorescence for each pixel within the outline of the fungal spore; based on the measurements from the second, third, and fourth color images of degree and color of fluorescence, estimating a concentration of each type of fluorescent biomolecule of interest for each image pixel within the outline of the fungal spore; generating two-dimensional images of concentrations of the fluorescent biomolecules of interest within the outline of the fungal spore; and determining the state of the fungal spore from the estimated concentrations of each type of fluorescent biomolecule of interest.

In an embodiment, the method includes using an integrated camera sensor chip package to capture the first two-dimensional color image of the fungal spore, and second, third, and fourth color images of the fungal spore, wherein the integrated camera sensor chip package comprises a light-sensing pixel sensor array, analog drive and readout circuitry, analog-to-digital conversion circuitry, digital image processing circuitry, and digital communications circuitry.

In another specific embodiment, a method includes directing a flow of air comprising a fungal spore to a collection cartridge; trapping the fungal spore on a tape medium of the collection cartridge; positioning the fungal spore within a field of view of a camera sensor while the fungal spore remains trapped on the tape medium of the collection cartridge; activating an ultraviolet (UV) light source to illuminate the trapped fungal spore with UV light; opening a camera shutter associated with the camera sensor for a time period; while the trapped fungal spore is illuminated with the UV light, allowing the camera sensor to collect light emitted from the trapped fungal during a first portion of the time period; after the first portion of the time period has elapsed, directing, during a second portion of the time period after the first portion of the time period, a first burst of white light, originating from a first position, towards the trapped fungal spore; directing, during the second portion of the time period, a second burst of white light, originating from a second position, different from the first position, towards the trapped fungal spore; after the second portion of the time period has elapsed, closing the camera shutter to generate an image; and analyzing the image to obtain a shape of the trapped fungal spore.

The method may further include directing, during the second portion of the time period, a third burst of white light, originating from a third position, different from the first and second positions, towards the trapped fungal spore.

In an embodiment, the first burst of white light is from a first light emitting diode (LED) providing illumination corresponding to a first corner of the field of view, the second burst of white light is from a second LED providing illumination corresponding to a second corner of the field of view, the third burst of white light is from a third LED providing illumination corresponding to a third corner of the field of view, and the UV light source provides illumination corresponding to a fourth corner of the field of view.

In an embodiment, the second portion of time period has a duration that is less than a duration of the first portion of the time period. In an embodiment, a duration of the time period is about 15 seconds, a duration of the first portion of the time period is about 14 seconds, and a duration of the second portion of the time period is about 1 second. In an embodiment, durations of each of the first and second bursts of white light during the second portion of the time period are less than 1 second.

In an embodiment, the UV light source originates from a third position, different from the first and second positions, the first, second, and third positions are arranged about the field of view of the camera sensor, and the first, second, and third positions are spaced 120-degrees apart from each other.

In an embodiment, the method includes using an integrated camera sensor chip package to generate the image, wherein the integrated camera sensor chip package comprises a light-sensing pixel sensor array, analog drive and readout circuitry, analog-to-digital conversion circuitry, digital image processing circuitry, and digital communications circuitry.

The method may include after the analyzing the image to obtain a shape of the trapped fungal spore, determining a state of the fungal spore. Determining a state of the fungal spore may include inferring concentrations of biomolecules of interest within the fungal spore by correlating a value of a pixel located at coordinates (x,y) on the image to a concentration of a biomolecule of interest as being at the coordinates (x,y) on the image; obtaining reference information comprising fluorescent properties of the biomolecules of interest associated with known states of the fungal spore; obtaining camera sensor information of the camera sensor, the camera sensor information comprising color sensitivity characteristics of the camera sensor; and processing the inferred concentrations of the biomolecules of interest with the fluorescent properties reference information and camera sensor information to determine the state of the fungal spore.

In a specific embodiment, the first and second bursts of white light are from a single light source and the method includes: after the directing a first burst of white light, moving the single light source to the second position for the second burst of white light.

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples, and are not meant to be limiting in any way. Other steps and functions may be contemplated without departing from this disclosure or the scope of an embodiment. Other embodiments include systems and non-volatile media products that execute, embody or store processes that implement the methods described above.

What is claimed is:

1. A method comprising:
    directing a flow of air comprising a fungal spore to a collection cartridge;
    trapping the fungal spore on a tape medium of the collection cartridge;
    positioning the fungal spore within a field of view of a camera sensor while the fungal spore remains trapped on the tape medium of the collection cartridge;
    activating an ultraviolet (UV) light source to illuminate the trapped fungal spore with UV light;
    opening a camera shutter associated with the camera sensor for a time period;
    while the trapped fungal spore is illuminated with the UV light, allowing the camera sensor to collect light emitted from the trapped fungal during a first portion of the time period;
    after the first portion of the time period has elapsed, directing, during a second portion of the time period after the first portion of the time period, a first burst of white light, originating from a first position, towards the trapped fungal spore;
    directing, during the second portion of the time period, a second burst of white light, originating from a second position, different from the first position, towards the trapped fungal spore;
    after the second portion of the time period has elapsed, closing the camera shutter to generate an image; and
    analyzing the image to obtain a shape of the trapped fungal spore.

2. The method of claim 1 comprising:
    directing, during the second portion of the time period, a third burst of white light, originating from a third position, different from the first and second positions, towards the trapped fungal spore.

3. The method of claim 2 wherein the first burst of white light is from a first light emitting diode (LED) providing illumination corresponding to a first corner of the field of view,
- the second burst of white light is from a second LED providing illumination corresponding to a second corner of the field of view,
- the third burst of white light is from a third LED providing illumination corresponding to a third corner of the field of view, and
- the UV light source provides illumination corresponding to a fourth corner of the field of view.

4. The method of claim 2 wherein the second portion of time period has a duration that is less than a duration of the first portion of the time period.

5. The method of claim 2 wherein a duration of the time period is about 15 seconds, a duration of the first portion of the time period is about 14 seconds, and a duration of the second portion of the time period is about 1 second.

6. The method of claim 2 wherein durations of each of the first and second bursts of white light during the second portion of the time period are less than 1 second.

7. The method of claim 1 wherein the UV light source originates from a third position, different from the first and second positions, and
- wherein the first, second, and third positions are arranged about the field of view of the camera sensor, and
- wherein the first, second, and third positions are spaced 120-degrees apart from each other.

8. The method of claim 1 comprising:
- using an integrated camera sensor chip package to generate the image, wherein the integrated camera sensor chip package comprises a light-sensing pixel sensor array, analog drive and readout circuitry, analog-to-digital conversion circuitry, digital image processing circuitry, and digital communications circuitry.

9. The method of claim 1 comprising:
- after the analyzing the image to obtain a shape of the trapped fungal spore, determining a state of the fungal spore.

10. The method of claim 9 wherein the determining a state of the fungal spore comprises inferring concentrations of biomolecules of interest within the fungal spore by correlating a value of a pixel located at coordinates (x,y) on the image to a concentration of a biomolecule of interest as being at the coordinates (x,y) on the image;
- obtaining reference information comprising fluorescent properties of the biomolecules of interest associated with known states of the fungal spore;
- obtaining camera sensor information of the camera sensor, the camera sensor information comprising color sensitivity characteristics of the camera sensor; and
- processing the inferred concentrations of the biomolecules of interest with the fluorescent properties reference information and camera sensor information to determine the state of the fungal spore.

11. The method of claim 1 wherein the first and second bursts of white light are from a single light source and the method comprises:
- after the directing a first burst of white light, moving the single light source to the second position for the second burst of white light.

* * * * *